US011541378B2

(12) United States Patent
Shannon et al.

(10) Patent No.: US 11,541,378 B2
(45) Date of Patent: Jan. 3, 2023

(54) MOLECULAR SIEVE INTERGROWTHS OF CHA AND AFT HAVING AN "SFW-GME TAIL," METHODS OF PREPARATION AND USE

(71) Applicant: JOHNSON MATTHEY PUBLIC LIMITED COMPANY, London (GB)

(72) Inventors: Mervyn Shannon, Billingham (GB); Alessandro Turrina, Billingham (GB); Sanyuan Yang, Savannah, GA (US)

(73) Assignee: Johnson Matthey Public Limited Company, London (GB)

(*) Notice: Subject to any disclaimer, the term of this patent is extended or adjusted under 35 U.S.C. 154(b) by 106 days.

(21) Appl. No.: 16/832,194

(22) Filed: Mar. 27, 2020

(65) Prior Publication Data

US 2020/0316572 A1 Oct. 8, 2020

Related U.S. Application Data

(60) Provisional application No. 62/825,474, filed on Mar. 28, 2019.

(51) Int. Cl.
*B01J 29/76* (2006.01)
*B01D 53/94* (2006.01)
(Continued)

(52) U.S. Cl.
CPC .......... *B01J 29/76* (2013.01); *B01D 53/9418* (2013.01); *B01D 53/9436* (2013.01); *B01J 29/06* (2013.01); *B01J 29/061* (2013.01); *B01J 29/064* (2013.01); *B01J 29/068* (2013.01); *B01J 29/072* (2013.01); *B01J 29/076* (2013.01); *B01J 29/70* (2013.01); *B01J 29/7015* (2013.01); *B01J 29/7049* (2013.01); *B01J 29/7065* (2013.01); *B01J 29/72* (2013.01); *B01J 29/723* (2013.01); *B01J 29/74* (2013.01); *B01J 29/763* (2013.01); *B01J 29/78* (2013.01); *B01J 29/783* (2013.01); *B01J 29/80* (2013.01); *B01J 35/04* (2013.01); *B01J 37/0018* (2013.01); *B01J 37/04* (2013.01); *B01J 37/10* (2013.01); *C01B 39/02* (2013.01); *C01B 39/04* (2013.01); *C01B 39/06* (2013.01); *C01B 39/48* (2013.01); *C07C 1/20* (2013.01); *C07C 1/24* (2013.01); *B01D 2255/50* (2013.01); *B01J 2029/062* (2013.01); *B01J 2229/18* (2013.01); *B01J 2229/183* (2013.01); *B01J 2229/186* (2013.01); *C01P 2002/72* (2013.01);
(Continued)

(58) Field of Classification Search
CPC ........ B01J 29/06; B01J 29/064; B01J 29/061; B01J 29/068; B01J 2029/062; B01J 29/072; B01J 29/076; B01J 29/70; B01J 29/7049; B01J 29/72; B01J 29/74; B01J 29/78; B01J 29/80; B01J 29/7015; B01J 29/7065; B01J 29/723; B01J 29/763; B01J 29/783; B01J 2229/18; B01J 2229/183; B01J 2229/186; B01J 35/002; B01J 35/04; B01J 37/0018; B01J 37/04; B01J 37/10; B01J 29/76; B01D 53/9418; B01D 53/9436; B01D 2255/50; C01P 2002/72; C01P 2002/77; C01P 2002/78; C07C 2529/70; C07C 2529/76; C07C 2529/72; C07C 2529/74; C07C 2529/78; C07C 1/20; C07C 1/24; C01B 39/06; C01B 39/48; C01B 39/02; C01B 39/04
USPC ........ 502/60, 61, 73, 74; 423/700, 701, 702, 423/703, 704, 705, 713, 716, 718, 235, 423/237, 239.1, 239.2; 585/638, 639, 640
See application file for complete search history.

(56) References Cited

U.S. PATENT DOCUMENTS 4,124,686 A 11/1978 Grose et al.
5,192,522 A 3/1993 Skeels et al.
(Continued)

FOREIGN PATENT DOCUMENTS

EP 1365992 A1 12/2003
EP 3 323 785 A1 * 5/2018
(Continued)

OTHER PUBLICATIONS

Rohrig et al., "Rietveld Refinement of the Crystal Structure of the Synthetic Porous Zincosilicate VPI-7" Zeolites, 1994 vol. 14, September/October, pp. 498-503.
(Continued)

*Primary Examiner* — Elizabeth D Wood

(57) ABSTRACT

Molecular sieves comprising intergrowths of cha and aft having an "sfw-GME tail", at least one structure directing agent (SDA) within the framework of the molecular sieve, an intergrowth of CHA and GME framework structures, cha cavities, and aft cavities are described. A first SDA comprising either an N,N-dimethyl-3,5-dimethylpiperidinium cation or a N,N-diethyl-2,6-dimethylpiperidinium cation is required. A second SDA, which can further be present, is a CHA or an SFW generating cation. The amount of the second SDA-2 used can change the proportion of the components in the cha-aft-"sfw-GME tail". Activated molecular sieves formed from SDA containing molecular sieves are also described. Compositions for preparing these molecular sieves are described. Methods of preparing a SDA containing JMZ-11, an activated JMZ-11, and metal containing activated JMZ-11 are described. Methods of using activated JMZ-11 and metal containing activated JMZ-11 in a variety of processes, such as treating exhaust gases and converting methanol to olefins are described.

42 Claims, 13 Drawing Sheets

(51) Int. Cl.

| | |
|---|---|
| *B01J 35/04* | (2006.01) |
| *B01J 37/00* | (2006.01) |
| *B01J 37/04* | (2006.01) |
| *B01J 37/10* | (2006.01) |
| *C01B 39/48* | (2006.01) |
| *C07C 1/24* | (2006.01) |
| *B01J 29/076* | (2006.01) |
| *B01J 29/068* | (2006.01) |
| *B01J 29/78* | (2006.01) |
| *B01J 29/06* | (2006.01) |
| *B01J 29/072* | (2006.01) |
| *B01J 29/74* | (2006.01) |
| *B01J 29/72* | (2006.01) |
| *B01J 29/70* | (2006.01) |
| *B01J 29/80* | (2006.01) |
| *B01J 29/064* | (2006.01) |
| *C07C 1/20* | (2006.01) |
| *C01B 39/02* | (2006.01) |
| *C01B 39/06* | (2006.01) |
| *C01B 39/04* | (2006.01) |

(52) U.S. Cl.
CPC ...... *C01P 2002/77* (2013.01); *C01P 2002/78* (2013.01); *C07C 2529/70* (2013.01); *C07C 2529/76* (2013.01)

(56) References Cited

U.S. PATENT DOCUMENTS

| | | | |
|---|---|---|---|
| 5,248,491 A | 9/1993 | Skeels et al. | |
| 6,379,531 B2 | 4/2002 | Lee et al. | |
| 7,906,099 B2 * | 3/2011 | Cao | B01J 29/90 423/700 |
| 9,643,853 B2 | 5/2017 | Xie | |
| 10,150,676 B2 | 12/2018 | Davis | |
| 2014/0271426 A1 | 9/2014 | Casci et al. | |
| 2015/0044133 A1 | 2/2015 | Davis | |
| 2017/0304812 A1 * | 10/2017 | Casci | B01D 53/02 |
| 2018/0093257 A1 | 4/2018 | Chen et al. | |
| 2018/0093258 A1 | 4/2018 | Chen et al. | |
| 2018/0093259 A1 | 4/2018 | Chen et al. | |
| 2018/0093897 A1 | 4/2018 | Chen et al. | |
| 2018/0244618 A1 | 8/2018 | Collier et al. | |

FOREIGN PATENT DOCUMENTS

| | | | |
|---|---|---|---|
| GB | 868649 A | | 5/1961 |
| GB | 2551622 A | * | 12/2017 |
| JP | 2017065943 A | | 4/2017 |
| WO | 2018086974 A1 | | 5/2018 |

OTHER PUBLICATIONS

Rohrig et al., "A New Zincosilicate Zeolite with Nine-Ring Channels", Angew. Chem. Int. Ed. Engl., 1995, 34. No. 1, pp. 63-65.

Lillerud et al., "Two Members of the ABC-D6R Family Zeolites: Zeolite Phi and Linde D", J. Chem. Soc. Fraaday Trans., 1994, pp. 1547-1551.

McGuire et al., "Structure Refinement, Electron Microscopy, and Solid-State Magic Angle Spinning Nuclear Magnetic Resonance Characterization of AlPO 4-52: An Aluminophosphate wtih a Large Cage", Zeolites 15, 1995, pp. 460-469.

Skeels et al., "Synthesis and Characterization of Phi-Type Zeolites LZ-276 and LZ-277: Faulted Members of the ABC-D6R Family of Zeolites", Microporous and Mesoporous Materials 30, 1999, pp. 335-346.

Szostak et al., "Babelite: the Random Member of the ABC-D6R Family of Zeolites" J. Chem. Soc., Chem. Commun., 1994, pp. 2357-2358.

http://europe.iza-structure.org/IZA-SC/intergrowth_families/ABC_6.pdf.

Slawinski et al., "Intergrowth Structure Modelling in Silicoaluminophosphate SAPO-18/34 Family", Microporous and Mesoporous Materials; 195; Apr. 2014, pp. 311-318.

Newsam et al., "The Structure of Zeolite ZSM-20: Mixed Cubic and Hexagonal Stackings of Faujasite Sheets", J Chem. Soc., Chem. Commun., Jan. 1989, pp. 493-495.

Merlino, "Lovdarite, $K_4Na_{12}(Be_8Si_{28}O_{72})$ 18 $H_2O$, a Zeolite-Like mineral: Structural Features and OD Character", Eur. J. Mineral., 1990, 2, pp. 809-817.

Rohrig et al., "A New Zincosilicate Xeolite with Nine-Ring Channels", Angew. Chem. Int. Ed. Engl., 1995, 34 No. 1 pp. 63-65.

Kuhl, "Influence of Phosphate and Other Complexing Agents on the Crystallisation of Zeolites", Molecular Sieves S.C.I., 1967, pp. 85-91.

Jagodzinski, "Eindimensionale Fehlordnung in Kristallen und ihr Einfluss auf die Rontgeninterferenzen. II. Berechnung der fehlgordneten dichtesten Kugelpackungen mit Wechselwirkungen der Reichweite 3", Mineralogisches Institut der Universitat Marburg, Deutschland, Dec. 7, 1948, pp. 208-211 (English Abstract).

Xie et al., "SSZ-52, a Zeolite with an 18-Layer Aluminosilicate Framework Structure Related to That of the DeNOx Catalyst Cu-SSZ-13", Journal of the American Chemical Society, (2013), 135, pp. 10519-10524.

Naraki et al., "ZTS-1 and Zl S-2: Novel Intergrowth Zeolites with AFX/CHA Structure", Microporous and Mesoporous Materials, 254, (2017), pp. 160-169.

Kim et al., "Synthesis of Faulted CHA-Type Zeolites with Controllable Faulting Probability" Microporous and Mesoporous Materials, 256, (2018), pp. 266-274.

Treacy et al., "A General Recursion Method for Calculating Diffracted Intensities from Crystals Containing Planar Faults", Proc. R. Soc. London Ser. A 433 (1991) pp. 499-520.

Biswa Nath Bhadra et al:—"Syntheses of SSZ-39 and mordenite zeolites with N,N-dialkyl-2, 6-dimethyl-piperidinium hydroxide/iodides: Phase-selective syntheses with anions Microporous and Mesoporous Materials" 235, 2016, 135-142.

* cited by examiner

Figure 5. Channels in CHA viewed along <010> (left), and along <111> (right).

H. van Koningsveld, Schemes for Building Zeolite Framework Models: http://www.iza-structure.org/databases/

Figure 11

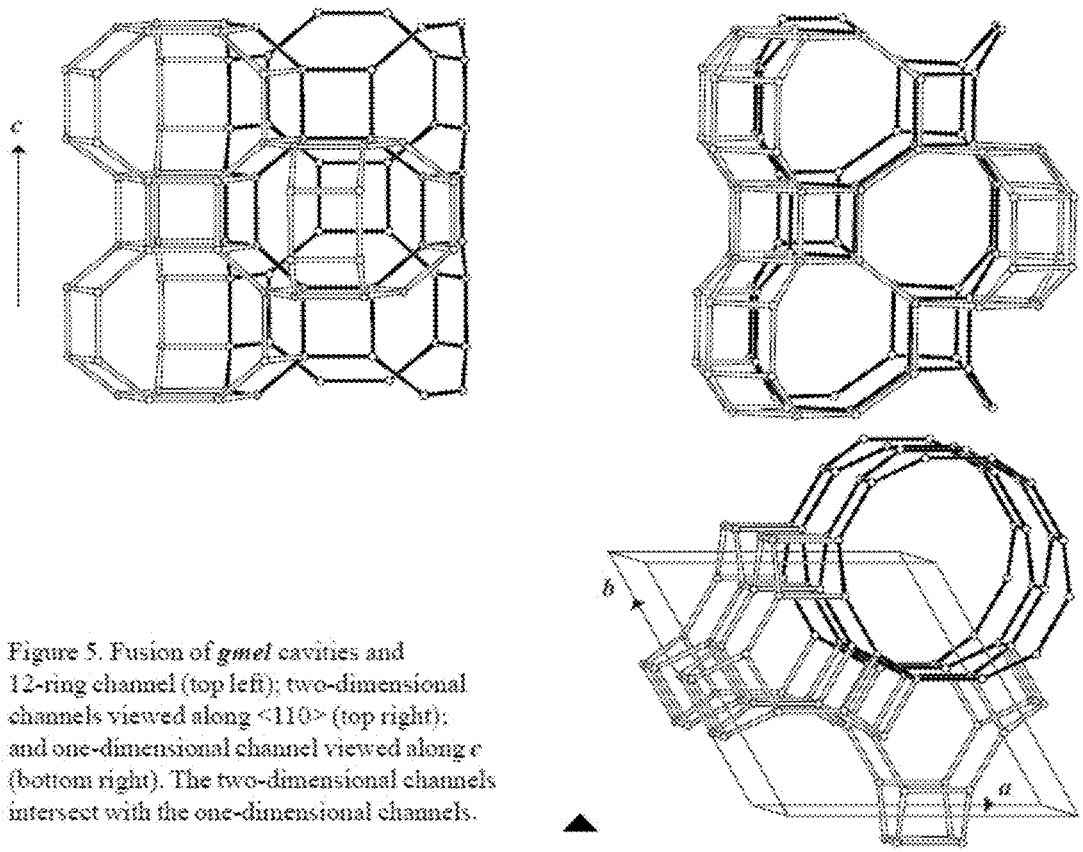

Figure 5. Fusion of *gmel* cavities and 12-ring channel (top left); two-dimensional channels viewed along <110> (top right); and one-dimensional channel viewed along *c* (bottom right). The two-dimensional channels intersect with the one-dimensional channels.

H. van Koningsveld, Schemes for Building Zeolite Framework Models: http://www.iza-structure.org/databases/

Figure 12

```
Stochastic intergrowth
     Reichweite 0
        1    2

/      \

| 1-p    p  |
     |  p    1-p |

Pure CHA = .... 1 1 1 1 1 1 ....
    or    .... 2 2 2 2 2 2 ....
Pure GME = .... 1 2 1 2 1 2 ....

<n_CHA> = 1/p layers
    <n_GME> = 1/(1-p) layers
```

Figure 13

```
Block intergrowth (simple)
       Reichweite 1
      1    2    3    4

/    /    \    \
   ( / ) ( \ ) ( / ) ( \ )

| 1-p    -    p    -  |
   |  q     -   1-q   -  |
   |  -    1-q   -    q  |
   |  -     p    -   1-p |

Pure CHA = .... 1 1 1 1 1 1 ....
    or    .... 4 4 4 4 4 4 ....
Pure GME = .... 2 3 2 3 2 3 ....

<n_CHA> = 1/p layers
    <n_GME> = 1/q layers

Stochastic, if q = 1-p
  Twinning, if p or q = 1
     AFX, if p = q = 1
```

Transition probability matrix for Reichweite 2 description
(i.e. previous two 5 Angstrom thick layers influence the stacking)

Simple stochastic CHA-GME framework intergrowth (equivalent to Reichweite 0)

Cage size distributions (r=1-p; q=1-p, s=1-r=p)

Simple "block" intergrowth of CHA and GME
p is prob CHA block faults, r is prob GME block faults (q=1-p, s=1-r)

$$f_{n+1} = (1-r)f_n \quad \text{for } n \geq 3$$

Example 1 type
for a *cha-aft-"sfw"-GME* tail intergrowth $$f_{n+1} = (1-r)f_n$$
$$\text{for } n \geq 4$$

MOLECULAR SIEVE INTERGROWTHS OF CHA AND AFT HAVING AN "SFW-GME TAIL," METHODS OF PREPARATION AND USE

FIELD OF INVENTION

The present invention relates to molecular sieves comprising intergrowths of cha and aft having an "sfw-GME tail". These molecular sieves include as-made molecular sieves containing one or more structure directing agents (SDAs), as well as activated molecular sieves, which do not contain an SDA, and can be formed from an SDA containing molecular sieve. The invention also relates to methods of preparation of the SDA containing molecular sieves and activated molecular sieves, and methods using these activated molecular sieves as a catalyst.

BACKGROUND OF THE INVENTION

Molecular sieves are a commercially important class of materials that have distinct crystal structures with defined pore structures that are shown by distinct X-ray diffraction (XRD) patterns. The crystal structure defines cavities and channels/pores that are characteristic of the specific type of molecular sieve. This is usually described as the framework type or topological type. A full listing of framework types is maintained by the IZA (International Zeolite Association) http://www.iza-structure.org/databases/. Such framework types or topological types are not defined by composition, but only by the arrangement of the T-atoms (tetrahedral atoms) that bound the channels/pores and cavities and make up a structure. A framework type or topological type is unique and is provided with a unique three letter code by the IZA.

During the formation and growth of a molecular sieve crystal, sometimes faults occur that can initiate the growth of different structures within the bulk material. This can result in the appearance of a separate phase recognized by XRD. This separate phase can be referred to as a disordered structure or an intergrowth. Disordered structures are defined as structures possessing periodic ordering in dimensions less than 3, such as 2, 1, or zero-dimensions. This phenomenon is also called stacking disorder of structurally invariant Periodic Building Units (PerBUs). In other words, disordered structures are those where the stacking sequence of the PerBU deviates from periodic ordering up to random stacking sequences. Chemical disorder (i.e. different cations on a particular site), dynamic disorder (i.e rotational disorder of template molecules) and structural disorder (i.e. disordered molecules in the cavities of zeolite frameworks) are excluded from this definition. The physical chemical properties and the catalytic behaviour of a disordered structure might be different to those of the ordered counterpart. Examples include CHA/AEI composed of layers of double six-member rings (M. Janssen, A. Verberckmoes, M. Mertens, A. Bons, W. Mortier, ExxonMobile Chemical Europe Inc. EP patent no. 1365 992 B1, 2007. W. A. Slawinski, D. S. Wragg, D. Akporiaye, H. Fjellvag, Microporous Mesoporous Mater., 2014, 195, 311-318), EMT/FAU composed of sod cages linked through double T6-rings into a hexagonal layer (J. M. Newsam, M. M. J. Treacy, D. E. W. Vaughan, K. G. Strohmaier, W. J. Mortier, Chem. Commun., 1989, 493-495), LOV/VSV/RSN composed of T9 units: two 4-rings connected through a single T atom related by pure translations along a- and b-axes (S. Merlino, Eur. J. Miner., 1990, 2, 809-817. C. Röhrig, H. Gies, B. Marler, Zeolites, 1994, 14, 498-503. C. Röhrig, H. Gies, Angew. Chem. Int. Ed. Engl., 1995, 34, 63-65) etc. Further Examples of disorder in zeolite frameworks are reported in the database of zeolite structures (http://europe.iza-structure.org/IZA-SC/intergrowth_Table.html). The synthetic conditions, the nature of the metal cations, the shape and size of the SDAs employed for the synthesis of structures belonging to a given family, may affect the ordered arrangement of the building units, resulting in the formation of intergrowth and stacking disorder structures.

The new intergrowth zeolites herein described are related to the ABC-6 family of structures, in particular those containing only double six-rings (D6Rs) (http://europe.iza-structure.org/IZA-SC/intergrowth_families/ABC_6.pdf). The ABC-6 structures are built up from 6Rs with different stacking arrangements along one axis and linked by 4Rs. The 6R units can be centred on three different positions along the hexagonal ab-plane: A (0, 0, 0), B (2/3, 1/3, 0) and C (1/3, 2/3, 0).

The molecular sieves synthesised and identified as member of the disordered ABC-6 family consisting only of double-6-rings are: ZK-14 [G. H. Kuehl. In: Molecular Sieves S. C. I., London, 1967, p 85]; Babelite [R. Szostak and K. P. Lillerud, J. Chem. Soc. Chem. Commun. 1994, (20), 2357-2358]; Linde D [K. P. Lillerud, R. Szostak and A. Long, J. Chem. Soc. Faraday Trans. 1994, 90, 1547-1551; GB Patent 868, 649]; Phi [K. P. Lillerud, R. Szostak and A. Long, J. Chem. Soc. Faraday Trans. 1994, 90, 1547-1551; U.S. Pat. No. 4,124,686]; LZ-276 [G. W. Skeels, M. Sears, C. A. Bateman, N. K. McGuire, E. M. Flanigen, M. Kumar, R. M. Kirchner, Micropor. Mesopor. Mater. 30, 335 (1999); U.S. Pat. No. 5,248,491]; LZ-277 [G. W. Skeels, M. Sears, C. A. Bateman, N. K. McGuire, E. M. Flanigen, M. Kumar, R. M. Kirchner, Micropor. Mesopor. Mater. 30, 335 (1999); U.S. Pat. No. 5,192,522]; SAPO AFX/CHA [U.S. Pat. No. 7,906,099]; SSZ-52 [D. Xie, L. B. McCusker, C. Baerlocher, S. I. Zones, W. Wan, X. Zou, J. Am. Chem. Soc. 2013, 135(28), 10519-24; U.S. Pat. No. 6,379,531]; ZTS-1 and ZTS-2 [Y. Naraki, K. Ariga, K. Nakamura, K. Okushita, T. Sano, Microporous Mesoporous Mater. (2017) 254, 160-169; JP Patent 2017065943]; faulted CHA-type zeolites [J. Kim, D. H. Kim, Microporous Mesoporous Mater. 2018, 256, 266-274]; faulted-GME [U.S. Pat. No. 9,643,853]; SSZ-52x [U.S. Pat. No. 10,150,676]; GME/CHA [WO 2018/086974].

WO 2018/086974 discloses a method of preparing a series of zeolites belonging to the ABC-6 framework family with disorder in the ABC stacking sequence and with silica to alumina ratio in the range 8-60. The diffraction peaks in claim 3 and the relative Examples reported allow to classify these zeolites as stochastic CHA-GME intergrowths.

Molecular sieves have numerous industrial applications, and molecular seizes having certain frameworks, such as CHA, are known to be effective catalyst for treating combustion exhaust gas in industrial applications including internal combustion engines, gas turbines, coal-fired power plants, and the like. In one Example, nitrogen oxides (NOx) in the exhaust gas may be controlled through a so-called selective catalytic reduction (SCR) process whereby NOx compounds in the exhaust gas are contacted with a reducing agent in the presence of a zeolite catalyst. In another Example, molecular sieves having the CHA framework type have found application in the conversion of methanol to olefins (MTO) catalysis.

There is a need to develop new molecular sieves having the basic structure of known molecular sieves, where minor changes in the structure can affect one or more of the catalytic properties of the molecular sieve. In some cases, while minor changes in the structure may not be discernible using normally used analytical techniques, the catalytic activity of the structurally modified zeolite may be improved relative to very closely related analogous zeolites. Unexpected improvements in the catalytic activity of such structurally modified molecular sieves can allow for the compositions of exhaust gases from engines to meet various regulatory requirements.

SUMMARY OF THE INVENTION

In a first aspect of the invention, provided are a family (JMZ-11) of molecular sieves comprising intergrowths of cha and aft having an "sfw-GME tail", where the molecular sieves comprise one or more structure direct agents, hereinafter called "the molecular sieves" or "these molecular sieves". The "sfw-GME tail" can be determined by analysis using a Reichweite 2 DIFFaX model.

Four subgroups of the JMZ-11 family of molecular sieves, JMZ-11A, JMZ-11B, JMZ-11C and JMZ-11D, comprising these intergrowths are described below.

JMZ-11A comprises a structure direct agent (SDA-1), where SDA-1 is a N,N-dimethyl-3,5-dimethylpiperidinium cation, cha cavities, aft cavities and an "sfw-GME" tail, wherein the cha cavities are present at about 45 to about 65%, preferably about 54%, of the cavities in the tail, the aft cavities are present at about 18 to about 28%, preferably about 23% of the cavities in the tail, and the remaining about 7 to about 37%, preferable about 23%, of larger cavities in the "sfw-GME" tail. The gme cavities associated with the aft and larger cavities are not included in these figures. The "sfw-GME" tail accounts for about 35-80% of the volume of the molecular sieve or the molecular sieve particle, preferably about 68%. JMZ-11A has a monotonically decreasing distribution of cavity sizes, but it cannot be described as a stochastic CHA-GME intergrowth.

JMZ-11B comprises a structure direct agent (SDA-1), where SDA-1 is a N,N-diethyl-2,6-dimethylpiperidinium cation, cha cavities, aft cavities and an "sfw-GME" tail, wherein the cha cavities are present at about 55 to about 75%, preferably about 65%, of the cavities in the tail, the aft cavities are present at about 0 to about 10%, preferably about 5% of the cavities in the tail, and the remaining about 15 to about 45%, preferable about 30%, of larger cavities in the "sfw-GME" tail. The gme cavities associated with the aft and larger cavities are not included in these figures. The "sfw-GME" tail accounts for about 40-80% of the volume of the molecular sieve or the molecular sieve particle, preferably about 64%. JMZ-11B has a monotonically decreasing distribution of cavity sizes, but it cannot be described as a stochastic CHA-GME intergrowth.

JMZ-11C comprises two structure direct agents, an N,N-dimethyl-3,5-dimethylpiperidinium cation and a 1,3-bis(1-adamantyl)imidazolium cation, cha cavities, aft cavities and an "sfw-GME" tail, wherein the cha cavities are present at about 30 to about 45%, preferably about 39%, of the cavities in the tail, the aft cavities are present at about 45 to about 65%, preferably about 54% of the cavities in the tail, and the remaining about 2 to about 20%, preferable about 7%, of larger cavities in the "sfw-GME" tail. The gme cavities associated with the aft and larger cavities are not included in these figures. The "sfw-GME" tail accounts for about 5-45% of the volume of the molecular sieve or the molecular sieve particle, preferably about 23%. JMZ-11C has a monotonically decreasing distribution of cavity sizes, but it cannot be described as a stochastic CHA-GME intergrowth.

JMZ-11D comprises two structure direct agents, an N,N-dimethyl-3,5-dimethylpiperidinium cation and a trimethyl-admandylammonium cation, cha cavities, aft cavities and an "sfw-GME" tail, wherein the cha cavities are present at about 55 to about 75%, preferably about 65%, of the cavities in the tail, the aft cavities are present at about 7 to about 17%, preferably about 12% of the cavities in the tail, and the remaining about 8 to about 38%, preferable about 23%, of larger cavities in the "sfw-GME" tail. The gme cavities associated with the aft and larger cavities are not included in these figures. The "sfw-GME" tail accounts for about 50-90% of the volume of the molecular sieve or the molecular sieve particle, preferably about 75%. JMZ-11D has a monotonically decreasing distribution of cavity sizes, but it cannot be described as a stochastic CHA-GME intergrowth.

The molecular sieves described herein can be an aluminosilicate or a metal-substituted aluminosilicate. Preferably, the molecular sieve is an aluminosilicate.

These molecular sieves can comprise phosphorus in the framework. These molecular sieves can be an aluminophosphate (APO), a metal-substituted aluminophosphate (MeAlPO), a silico-aluminophosphate (SAPO), or a metal substituted silico-aluminophosphate.

These molecular sieves can comprise at least one metal within the framework where the metal is from one of the groups IIIA, IB, IIB, VA, VIA, VIIA, VIIIA of the Periodic Table, and combinations thereof. Preferably the metal is one or more of cerium, chromium, cobalt, copper, iron, magnesium, manganese, molybdenum, nickel, palladium, platinum, rhodium, titanium, tungsten, vanadium and zinc. More preferably the metal is one or more of cobalt, copper, iron, manganese and zinc.

In a second aspect of the invention, an activated H-form hereinafter called "the activated molecular sieves" or "these activated molecular sieves" of the molecular sieves of the first aspect of the invention are described.

The activated H-form of these molecular sieves can be an aluminosilicate or a metal-substituted aluminosilicate. Preferably, the activated H-form of These molecular sieves is an aluminosilicate.

The activated H-form of these molecular sieves can contain a phosphorus thin the framework. These activated H-form of these molecular sieves can be an aluminophosphate (AlPO), a metal-substituted aluminophosphate (MeAlPO), a silico-aluminophosphate (SAPO), or a metal substituted silico-aluminophosphate.

The activated H-form of these molecular sieves can comprise at least one metal within the framework where the metal is selected from at least one of the metals of groups IIIA, IB, IIB, VA, VIA, VIIA, and VIIIA of the Periodic Table, and combinations thereof. Preferably the metal is cerium, chromium, cobalt, copper, iron, magnesium, manganese, molybdenum, nickel, palladium, platinum, rhodium, titanium, tungsten, vanadium or zinc. More preferably the metal is cobalt, copper, iron, manganese, or zinc.

The activated H-form of these molecular sieves can comprise at least one extra-framework metal selected from the group consisting of Ag, Au, Ce, Co, Cr, Cu, Fe, Ga, In, Ir, Mn, Mo, Ni, Os, Pd, Pt, Re, Rh, Ru, Sn and Zn, preferably Cu, Fe, Co and Ni, more preferably Cu and Fe, most preferably Cu.

In a third aspect of the invention, a catalyst comprises an activated H-form of one or more of the molecular sieves of the second aspect of the invention and at least one extra-framework metal selected from the group consisting of Ag, Au, Ce, Co, Cr, Cu, Fe, Ga, In, Ir, Mn, Mo, Ni, Os, Pd, Pt, Re, Rh, Ru, Sn and Zn, preferably Cu, Fe, Co and Ni, more preferably Cu and Fe, most preferably Cu.

The activated H-form molecular sieve in the catalyst can comprise about 0.1 to about 5 weight percent of at least one extra-framework metal.

The activated H-form of these molecular sieves can be an aluminosilicate or a metal-substituted aluminosilicate, preferably an aluminosilicate.

The activated H-form of these molecular sieves can contain phosphorus in the framework. These activated H-form of these molecular sieves can be an aluminophosphate (AlPO), a metal-substituted aluminophosphate (MeAlPO), a silico-aluminophosphate (SAPO), or a metal substituted silico-aluminophosphate.

The activated H-form of these molecular sieves can comprise at least one metal within the framework where the metal is selected from at least one of the metals of groups IIIA, IB, IIB, VA, VIA, VIIA and VIIIA of the Periodic Table, and combinations thereof. Preferably the metal is one or more of cerium, chromium, cobalt, copper, iron, magnesium, manganese, molybdenum, nickel, palladium, platinum, rhodium, titanium, tungsten, vanadium and zinc, more preferably cobalt, copper, iron, manganese and zinc.

In a fourth aspect of the invention, a catalyst article for treating exhaust gas comprises a catalyst comprising an activated H-form of one or more of the molecular sieves of the second aspect of the invention and at least one extra-framework metal selected from the group consisting of Ag, Au, Ce, Co, Cr, Cu, Fe, Ga, In, Ir, Mn, Mo, Ni, Os, Pd, Pt, Re, Rh, Ru, Sn and Zn, preferably Cu, Fe, Co and Ni, more preferably Cu and Fe, most preferably Cu.

The activated H-form of these molecular sieves in the catalyst can comprise about 0.1 to about 5 weight percent of at least one extra-framework metal.

The catalyst can be disposed on and/or within a porous substrate, preferably a flow through or wall-flow filter.

In a fifth aspect of the invention, systems for treating exhaust gas generated by combustion process, such as from an internal combustion engine (whether mobile or stationary), a gas turbine, coal or oil fired power plants, and the like, comprise a catalyst article comprising an activated H-form of one or more of the molecular sieves of the second aspect of the invention and at least one extra-framework metal. Such systems include a catalytic article comprising an activated molecular sieve, described herein, and can include at least one additional component for treating the exhaust gas, wherein the catalytic article and at least one additional component are designed to function as a coherent unit.

An exhaust system for treating exhaust gases from an engine can comprise: (a) a catalyst article comprising one or more of an activated H-form of one or more of the molecular sieves of the second aspect of the invention and at least one extra-framework metal selected from the group consisting of Ag, Au, Ce, Co, Cr, Cu, Fe, Ga, In, Ir, Mn, Mo, Ni, Os, Pd, Pt, Re, Rh, Ru, Sn and Zn, preferably Cu, Fe, Co and Ni, more preferably Cu and Fe, most preferably Cu, disposed downstream from the engine; (b) a source of a reductant, such as ammonia or urea upstream of said catalyst article; and (c) an exhaust gas conduit for carrying the exhaust gases from the engine to said catalyst article.

In some embodiments, the activated H-form of these molecular sieves can be an SCR or an ammonia oxidation component.

A system can comprise a catalytic article comprising one or more of these molecular sieves or one or more of a metal containing activated molecular sieves, a conduit for directing a flowing exhaust gas, and a source of nitrogenous reductant disposed upstream of the catalytic article. The system can include a controller for metering the nitrogenous reductant into the flowing exhaust gas only when it is determined that one or more activated molecular sieves or one or more metal containing activated molecular sieves is capable of catalyzing $NO_x$ reduction at or above a desired efficiency over a specific temperature range, such as at above 100° C., above 150° C. or above 175° C. The metering of the nitrogenous reductant can be arranged such that 60% to 200% of theoretical ammonia is present in exhaust gas entering the SCR catalyst calculated at 1:1 $NH_3/NO$ and 4:3 $NH_3/NO_2$.

The system can comprise an oxidation catalyst (e.g., a diesel oxidation catalyst (DOC)) for oxidizing nitrogen monoxide in the exhaust gas to nitrogen dioxide can be located upstream of a point of metering the nitrogenous reductant into the exhaust gas. The oxidation catalyst can be adapted to yield a gas stream entering the SCR molecular sieve catalyst having a ratio of NO to $NO_2$ of from about 4:1 to about 1:3 by volume, e.g. at an exhaust gas temperature at oxidation catalyst inlet of 250° C. to 450° C. The oxidation catalyst can include at least one platinum group metal (or some combination of these), such as platinum, palladium, or rhodium, coated on a flow-through monolith substrate. The at least one platinum group metal can be platinum, palladium or a combination of both platinum and palladium. The platinum group metal can be supported on a high surface area washcoat component such as alumina, a zeolite, silica, non-zeolite silica alumina, ceria, zirconia, titania or a mixed or composite oxide containing both ceria and zirconia.

A suitable filter substrate can be located between the oxidation catalyst and the SCR catalyst. Filter substrates can be selected from any of those mentioned above, e.g. wall flow filters. Where the filter is catalyzed, e.g. with an oxidation catalyst of the kind discussed above, preferably the point of metering nitrogenous reductant is located between the filter and the molecular sieve catalyst. Alternatively, if the filter is un-catalyzed, the means for metering nitrogenous reductant can be located between the oxidation catalyst and the filter.

In a sixth aspect of the invention, a method for synthesizing an SDA containing molecular sieve of the first aspect of the invention comprises:
 a. forming a reaction mixture comprising: (i) at least one source of aluminum, (ii) at least one source of silicon, (iii) at least one source of alkaline or alkaline-earth cations and (iv) one or more structure directing agents;
 b. heating the reaction mixture;
 c. forming molecular sieve crystals having an intergrowth and the structure directing agent as described herein, and
 d. recovering at least a portion of the molecular sieve crystals from the reaction mixture.

The SDA for JMZ-11A comprises an N,N-dimethyl-3,5-dimethylpiperidinium cation. The SDA for JMZ-11B comprises an N,N-diethyl-2,6-dimethylpiperidinium cation. The SDA for JMZ-11C comprises an N,N-dimethyl-3,5-dimethylpiperidinium cation and a 1,3-bis(1-adamantyl)imidazolium cation. The SDA for JMZ-11D comprises an N,N-dimethyl-3,5-dimethylpiperidinium cation and a trimethyladmandylammonium cation.

The at least one source of aluminum can comprise aluminum alkoxides, aluminum phosphates, aluminum hydroxide, sodium aluminate, pseudoboehmite, hydrated alumina, organo alumina, colloidal alumina, zeolite Y and mixtures thereof.

The at least one source of silicon can be an alkoxide, colloidal silica, silica gel, a silicate, a tetraalkyl orthosilicate, or an aqueous colloidal suspension of silica.

The source of alkaline or alkaline-earth cations may be any source of these elements, preferably selected from a source of Na, K and combinations thereof.

The cation of the structure directing agent can be associated with an anion selected from the group consisting of acetate, bicarbonate, bromide, carbonate, carboxylate, chloride, fluoride, hydroxide, iodide, sulfate and tetrafluoroborate. Preferably the anion is hydroxide.

The reaction mixture can have a molar compositional ratio of:

| Components | Ratio | Preferred Ratio |
| --- | --- | --- |
| $MeO_2/A_2O_3$ | 10-100 | 20-50 |
| $(SDA-1 + SDA-2 + SDA-3)/A_2O_3$ | 1-6 | 1.0-3.0 |
| SDA-2/SDA-1 | 0-100 | 0.00-15.0 |
| SDA-3/SDA-1 | 0-100 | 0.00-15.0 |
| $X_2O/A_2O_3$ | 5.0-20.0 | 7.5-15 |
| $[OH^-]/A_2O_3$ | 10.0-30.0 | 16.0-30 |
| $H_2O/A_2O_3$ | 100-2000 | 200-800 | where Me is Si, Ge, Sn, Ti or combinations thereof and is calculated as being in the oxide form ($MO_2$); A is Al, Fe, Cr, B, Ga or combinations thereof and is calculated as being in the oxide form ($A_2O_3$); X is Na, K or a combination thereof and is calculated as being in the oxide form ($X_2O$); [OH-] is calculated being as the sum of hydroxide ions brought by all components; SDA-1 is an N,N-dimethyl-3,5-dimethylpiperidinium cation or an N,N-diethyl-2,6-dimethylpiperidinium cation, SDA-2 is a CHA generating SDA, such as a trimethyladmandylammonium cation, a tetraethylammonium cation, a trimethylbenzylammonium cation, a trimethylcyclohexylammonium cation or a trimethyl(cyclohexylmethyl)ammonium or a phenyltrimethylammonium cation and SDA-3 is a AFX generating SDA, such as a 1,3-bis(1-adamantyl)imidazolium, 1,1-(butane-1,4-diyl)bis-(quinuclidin-1-ium), 1,1-(pentane-1,5-diyl)bis-(quinuclidin-1-ium), 1,1'-(1,4-butanediyl)bis(4-aza-1-azoniabicyclo[2.2.2]octane), 1,1'-(1,5-pentanediyl)bis(4-aza-1-azoniabicyclo[2.2.2]octane).

The reaction mixture can further comprise from about 0.1 to about 10% w/w of seed crystals, wherein the seed crystals comprise a crystalline molecular sieve having an AEI, AFX, AFT, CHA, GME or an SFW framework and/or an intergrowth having a JMZ-11 framework.

In a seventh aspect of the invention, methods of synthesizing an activated molecular sieve of the second aspect of the invention from a molecular sieve comprising structure directing agents (SDAs) of the first aspect of the invention, are described. An activated molecular sieve lacks the structure directing agent(s) that is present in the molecular sieve of the first aspect of the invention. Molecular sieves comprising structure directing agents (SDAs) can have the SDAs removed by calcination, treatment with compound that can react with and preferably decompose the SDA, such as a peroxide.

In an eighth aspect of the invention, a composition for manufacturing SDA containing molecular sieves of the first aspect of the invention comprises the following materials in the corresponding ratios:

The reaction mixture can have a molar compositional ratio of:

| Components | Ratio | Preferred Ratio |
| --- | --- | --- |
| $MeO_2/A_2O_3$ | 10-100 | 20-50 |
| $(SDA-1 + SDA-2 + SDA-3)/A_2O_3$ | 1-6 | 1.0-3.0 |
| SDA-2/SDA-1 | 0-100 | 0.00-15.0 |
| SDA-3/SDA-1 | 0-100 | 0.00-15.0 |
| $X_2O/A_2O_3$ | 5.0-20.0 | 7.5-15 |
| $[OH^-]/A_2O_3$ | 10.0-30.0 | 16.0-30 |
| $H_2O/A_2O_3$ | 100-2000 | 200-800 | where Me is Si, Ge, Sn, Ti or combinations thereof and is calculated as being in the oxide form ($MO_2$); A is Al, Fe, Cr, B, Ga or combinations thereof and is calculated as being in the oxide form ($A_2O_3$); X is Na, K or a combination thereof and is calculated as being in the oxide form ($X_2O$); [OH-] is calculated being as the sum of hydroxide ions brought by all components; SDA-1 is an N,N-dimethyl-3,5-dimethylpiperidinium cation or an N,N-diethyl-2,6-dimethylpiperidinium cation, SDA-2 is a CHA generating SDA, such as a trimethyladmandylammonium cation, a tetraethylammonium cation, a trimethylbenzylammonium cation, a trimethylcyclohexylammonium cation or a trimethyl(cyclohexylmethyl)ammonium or a phenyltrimethylammonium cation and SDA-3 is a AFX generating SDA, such as a 1,3-bis(1-adamantyl)imidazolium, 1,1-(butane-1,4-diyl)bis-(quinuclidin-1-ium), 1,1-(pentane-1,5-diyl)bis-(quinuclidin-1-ium), 1,1'-(1,4-butanediyl)bis(4-aza-1-azoniabicyclo[2.2.2]octane), 1,1'-(1,5-pentanediyl)bis(4-aza-1-azoniabicyclo[2.2.2]octane).

The composition can further comprise from about 0.1 to about 10% w/w of seed crystals, wherein the seed crystals comprise a crystalline molecular sieve having an AEI, AFX, AFT, CHA, GME or an SFW framework and/or an intergrowth having a JMZ-11, JMZ-11B or JMZ-11C framework.

In a ninth aspect of the invention, provided are methods of making an activated molecular sieve of the second aspect of the invention from a molecular sieve containing SDAs and alkali metal cations of the first aspect of the invention. Molecular sieves of the present invention may be a Na-form zeolite, a K-form zeolite, or a combined Na, K-form and the like, or may be an H-form zeolite, an ammonium-form zeolite, or a metal-exchanged zeolite. Methods of making an activated molecular sieve of the second aspect of the invention from a molecular sieve comprising SDAs and alkali metal cations of the first aspect of the invention can use typical ion exchange techniques what involve contacting the molecular sieve with a solution containing a salt of the desired replacing cation or cations. Ion exchange occurs post-synthesis and can take place either before or after the molecular sieve is calcined.

In a tenth aspect of the invention, provided are methods for treating an exhaust gas from an engine by contacting the exhaust gas with an activated molecular sieve of the second aspect of the invention as herein described.

A method for treating an exhaust gas comprises contacting a combustion exhaust gas containing $NO_x$ and/or $NH_3$ with an activated H-form of a molecular sieve of the second aspect of the invention as described herein to selectively reduce at least a portion of the $NO_x$ into $N_2$ and $H_2O$ and/or oxidize at least a portion of the $NH_3$.

A method for treating an exhaust gas comprising contacting a combustion exhaust gas containing $NO_x$ with a passive $NO_x$ absorber comprising an activated H-form of a molecular sieve of the second aspect of the invention, as described herein.

In an eleventh aspect of the invention, provided is a method of converting methanol to an olefin (MTO) by contacting methanol with an activated H-form of a molecular sieve of the second aspect of the invention as herein described.

BRIEF DESCRIPTION OF THE DRAWINGS

FIG. 11 is a representation of the GME building scheme from IZA.

FIG. 12 is a transition probability matrix for a Reichweite 0 where the stacking probability of a layer is independent of the previous stacking.

FIG. 13 is a transition probability matrix for a Reichweite 1 where the previous one 5 Angstrom thick layer influence the stacking probability.

DETAILED DESCRIPTION OF THE INVENTION

Figure 1:
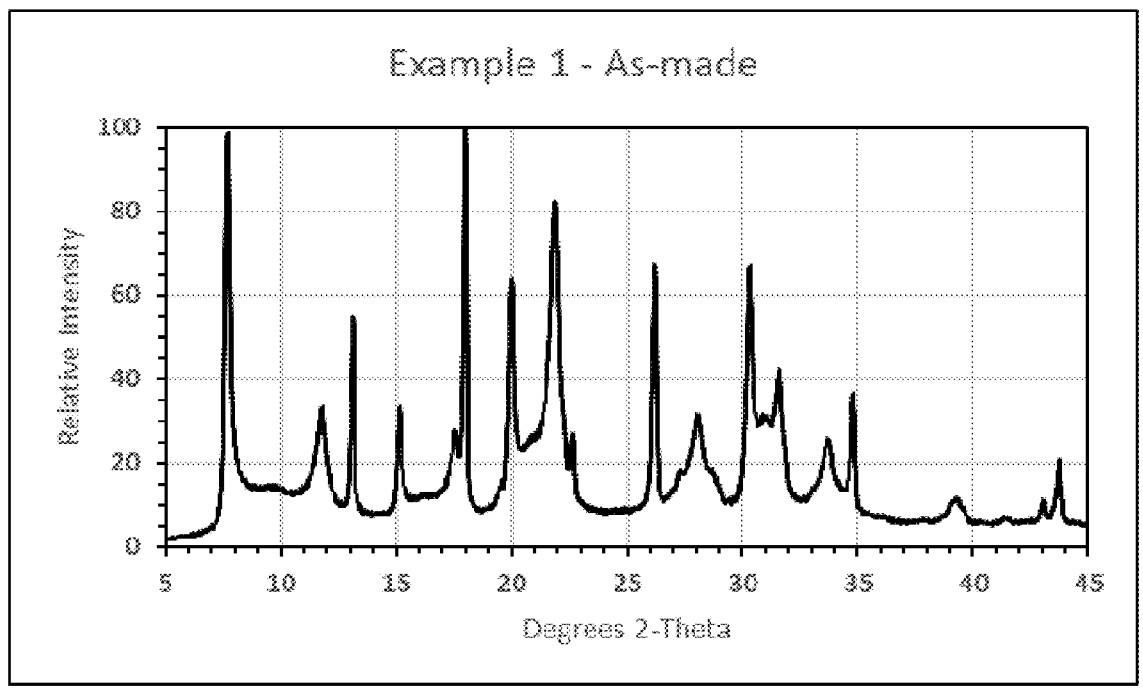
FIG. 1 is a powder XRD pattern of SDA containing (as-made) JMZ-11A with normalized intensities.

The following terms will be used throughout the specification and will have the following meanings unless otherwise indicated.

As used in this specification and the appended claims, the singular forms "a", "an" and "the" include plural referents unless the context clearly indicates otherwise. Thus, for example, reference to "a catalyst" includes a mixture of two or more catalysts, and the like.

The term "about" means approximately and refers to a range that is optionally ±25%, preferably ±10%, more preferably, ±5%, or most preferably ±1% of the value with which the term is associated.

The term "substantially similar", when used to describe a comparison of a diffraction pattern, means that the locations of one or more peaks, in degrees 2-theta, and the intensity of these peaks can vary based on experimental variability due to the instrumentation used, the conditions under which the diffraction pattern was obtained, and impurities that may be present in a sample.

When a range, or ranges, for various numerical elements are provided, the range, or ranges, can include the values, unless otherwise specified.

The term "stochastic" refers to a property that is randomly determined. It can have a random probability distribution or a pattern that may be analyzed statistically but may not be predicted precisely.

A "molecular sieve" is a crystalline substance with pores of molecular dimensions that permit the passage of molecules below a certain size. The term "molecular sieve" encompasses both zeolites and zeotypes. Zeolites are microporous crystalline aluminosilicates, composed of $TO_4$ tetrahedra (T=Si, Al) with O atoms connecting neighboring tetrahedra. Zeolites are materials having an alumina and silicate framework and include both aluminosilicates and metal-substituted aluminosilicates. Zeotypes are aluminophosphates (AlPO), metal-substituted aluminophosphates (MeAlPO), silico-aluminophosphates (SAPO), and metal substituted silico-aluminophosphates. The term "molecular sieve" can also include mixture of two or more of the above materials.

The term "framework type" is used in the sense described in the "Atlas of Zeolite Framework Types," Sixth Revised Edition, Elsevier, 2007.

The fundamental or primary building unit (PBU) in a zeolite structure is the $TO_4$ tetrahedron. Zeolite structure types can be described according to the structural building units within the framework, the pore openings and dimensionality of the channel system, and in the stacking of different polyhedral cage units. Structural building units, also known as secondary building units (SBUs), consist of tetrahedral units bound together into rings or cages by sharing a vertex for each pair of tetrahedra, via non-linear oxygen bridges. These SBUs are named in terms of the number of T-atoms they contain, for example a six-membered ring, 6R, or as pairs of rings denoted as double n-rings, (for example, double six-rings, D6R). A three-dimensional framework can be built by assembling only one kind of SBU. However, the structure of some zeolites is better described by using finite structural subunits (SSUs) which are polyhedral forms characterized by a quite complex symmetry, i.e. sodalite or gmelinite cages. The SSUs represent a structural feature. Therefore, they are not SBUs because very often the framework cannot be constructed from SSUs alone. Frequently, SSUs need to share corners, faces or edges to complete the framework. Another way to describe cages in the framework structure is to write them in terms of the rings that make up the faces of the cage, so that a D6R is expressed as [$4^6\ 6^2$]. Moreover, many structures can be described in terms of layers stacked upon each other, so-called infinite layers. SBUs and SSUs as such, are not meant to describe precursors from which the zeolite grows but may give clues to choose specific cations or structure-directing agents suitable to favor the formation of specific units and consequently of the desired framework structure.

The structural aspect of great importance in zeolites is the presence of cavities and channels connected to each other by means of windows to form a porous network within the structure. A pore is an opening that goes from one side of a crystal to another side of the crystal but is not straight. A pore contains section where the direction of the pore changes, generally multiple times, but still connects two sides of the crystal. A cavity is a polyhedral pore, which has at least one face defined by a ring large enough to be penetrated by compounds having a size that is less than the size of the ring, but which is not infinitely extended (i.e. not a channel). A channel is a pore that is infinitely extended in one dimension and is large enough to allow guest species to diffuse along its length. Channels can intersect to form 2- or 3-dimensional channel systems. The windows have molecular size and can adsorb chemical species small enough to pass through them. One factor that controls the ability to adsorb molecules into the zeolite is the size of the window or opening of the pore. A cage is a polyhedral pore whose windows are too narrow to be penetrated by guest species larger than $H_2O$. This mean that the window of a cage has a maximum size of a 6-member ring.

The term "framework" means a corner-sharing network of tetrahedrally coordinated atoms. The term "structure" means both the framework and extra-framework constituents.

There are three different volumes associated with a framework: the total volume of the framework, the volume of the channels and the volume of the cavities.

The term "extra-framework" refers to a material, preferably a metal, that is not located within the framework of a molecular sieve. The term "extra-framework metal" refers to a metal located on extra-framework site. The metal is from one of the groups VB, VIIB, VIIB, VIIIB, IB, or IIB of the Periodic Table and has been deposited onto extra-framework sites on the external surface or within the channels, cavities, or cages of the molecular sieves. Metals may be in one of several forms, including, but not limited to, zerovalent metal atoms or clusters, isolated cations, mononuclear or polynuclear oxycations, or as extended metal oxides.

The new intergrowth zeolites herein described are related to the ABC-6 family of structures, in particular those containing only double six-rings (D6Rs) (http://europe.iza-structure.org/IZA-SC/intergrowth_families/ABC_6.pdf). The ABC-6 structures are built up from 6Rs with different stacking arrangements along one axis and linked by 4Rs. The 6R units can be centred on three different positions along the hexagonal ab-plane: A (0, 0, 0), B (2/3, 1/3, 0) and C (1/3, 2/3, 0).

The molecular sieves described herein comprise intergrowths having a cha-aft-"sfw-GME tail".

An activated molecular sieve refers to a molecular sieve comprising an intergrowth having a cha-aft-"sfw-GME tail, as described herein, where there are no structure directing agents in the molecular sieve.

Intergrown molecular sieve phases are disordered planar intergrowths of molecular sieve frameworks. Reference is directed to the "Catalog of Disordered Zeolite Structures," 2000 Edition, published by the Structure Commission of the International Zeolite Association and to the "Collection of Simulated XRD Powder Patterns for Zeolites," Fifth Revised Edition, Elsevier, 2007, published on behalf of the Structure Commission of the International Zeolite Association for a detailed explanation on intergrown molecular sieve phases.

In a first aspect of the invention, provided are molecular sieves having intergrowths comprising a cha-aft-"sfw-GME tail" and one or more structure directing agents. These molecular sieves can be described as being "as-made". All 6-rings are present as double 6-rings in these molecular sieves. The use of italics indicates that the gme cavity (gme) associated with each aft cavity (aft) and the 2 gme cavities associated with each sfw cavity (sfw) are included. Cavities of cha and aft are referenced in lower case to include local AFX and AFT regions in the intergrowths. The term "sfw-GME" covers all cavities, including associated gme cavities, of the size of sfw and larger. Intergrowths of CHA-GME are described in the literature, however this does not mean that there is a GME phase present, but rather a range of cavity sizes up to the size of the particle of the molecular sieve. These molecular sieves containing this intergrowth is referred to herein as JMZ-11A, JMZ-11B, JMZ-11C and JMZ-11D.

The molecular sieve can be an aluminosilicate or a metal-substituted aluminosilicate, preferably an aluminosilicate. When the molecular sieve is an aluminosilicate, it can have a silica to alumina ratio (SAR) of 20 or less, preferably 15 or less, more preferably 10 or less.

The molecular sieve can comprise phosphorus in the framework, and can be an aluminophosphate (AlPO), a metal-substituted aluminophosphate (MeAlPO), a silico-aluminophosphate (SAPO), or a metal substituted silico-aluminophosphate, The molecular sieve can comprise one or more SDAs. The first SDA (SDA-1), which is required, can be an N,N-dimethyl-3,5-dimethylpiperidinium cation or an N,N-diethyl-2,6-dimethylpiperidinium cation. The second SDA (SDA-2), which can be present, is a CHA generating SDA, such as such as a trimethyladmandylammonium cation, a tetraethylammonium cation, a trimethylbenzylammonium cation, a trimethylcyclohexylammonium cation or a trimethyl(cyclohexylmethyl)ammonium or a phenyltrimethylammonium cation. The third SDA (SDA-3), which can be present, is a AFX generating SDA, such as a 1,3-bis(1-adamantyl)imidazolium, 1,1-(butane-1,4-diyl)bis-(quinuclidin-1-ium), 1,1-(pentane-1,5-diyl)bis-(quinuclidin-1-ium), 1,1'-(1,4-butanediyl)bis(4-aza-1-azoniabicyclo[2.2.2]octane), 1,1'-(1,5-pentanediyl)bis(4-aza-1-azoniabicyclo[2.2.2]octane). The amount of SDA-2 and or SDA-3 cations used can change the proportion of the cha-aft-"sfw-GME tail".

A molecular sieve of the first aspect of the invention can comprise at least one metal within the framework where the metal is selected from at least one of the metals of Groups IIIA, IB, IIB, VA, VIA, VIIA, VIIIA of the Periodic Table, and combinations thereof. Preferably the metal is one or more of cerium, chromium, cobalt, copper, iron, magnesium, manganese, molybdenum, nickel, palladium, platinum, rhodium, titanium, tungsten, vanadium and zinc. More preferably the metal is one or more of cobalt, copper, iron, manganese and zinc.

XRD Analysis

One of the characteristics of molecular sieves is their XRD pattern. The XRD pattern of SDA containing molecular sieves of the first aspect of the invention and activated molecular sieves of the second aspect of the invention were obtained using a Bruker D8 Advance fitted with a copper anode (x-ray wavelength 1.5406 A) and a LynxEye detector. The primary beam was fitted with a Goebels mirror and had a measurement circle of 280 mm, a slit of 0.22 mm and an axial soller of 2.5°. The secondary beam also had a measurement circle of 280 mm and axial soller of 2.5°. No slit was present. Step scanned data were collected between 3 and 100° two-theta with a step size of 0.022 at 1.5 steps/second. The sample was rotated at 15 rpm. The collected data were analysed with DIFFRAC.SUITE EVA Bruker software.

The relative intensities, $100 \times I/I_0$, where $I_0$ is the intensity of the strongest line or peak, and d, the interplanar spacing in Angstroms corresponding to the recorded lines, were calculated. Minor variations in the diffraction patterns of an SDA containing intergrowth and an activated molecular sieve in the tables or figures can also result from variations in the organic compound used in the preparation, the presence of water in the sample and from variations in the Si and Al mole ratios from sample to sample. Notwithstanding these minor perturbations, the basic crystal structures for the SDA containing intergrowth remain substantially unchanged. Similar variations can also be found in the X-ray diffraction patterns of activated molecular sieve samples.

As will be understood by those of skill in the art, the determination of the parameter 2θ is subject to both human and mechanical error, which in combination can impose an uncertainty of about ±0.2° on each reported value of 2θ. This uncertainty is, of course, also manifested in the reported values of the d-spacings, which are calculated from the 2θ. values. This imprecision is general throughout the art and is not sufficient to preclude the differentiation of the present crystalline materials from each other and from the compositions of the prior art. In some of the x-ray patterns reported, the relative intensities of the d-spacings are indicated by the notations vs, s, m, and w which represent very strong, strong, medium, and weak, respectively. In terms of relative intensity ($100 \times I/I_0$), the above designations are defined as: w (weak)<20; m (medium) is ≥20 and <40; s (strong) is ≥40 and <60; and vs (very strong) is ≥60. When the intensity is near the endpoint for a range, the intensity may be characterized was being in either of the ranges. For example, intensities of 18-22 may be listed as w-m. However, due to variations in intensity of the lines, as known in the art, one or more of the lines may have an intensity that is in an adjacent range.

In a second aspect of the invention, JMZ-11 and the four subgroups of the JMZ-11 family of molecular sieves, JMZ-11A, JMZ-11B, JMZ-11C and JMZ-11D, described herein, are present in an activated form. The term "activated" refers to a molecular sieve that has had two or more structure directing agents (SDAs) removed from the framework structure or to one or more processes that can remove a structure directing agent from a molecular sieve. A material containing two or more SDAs can become activated by a number of process known to one skilled in the art, such a calcination or treatment with peroxide.

The term "calcine", or "calcination", means heating the material in air, oxygen or an oxygen containing gas atmosphere. This definition is consistent with the IUPAC definition of calcination. (IUPAC. Compendium of Chemical Terminology, 2nd ed. (the "Gold Book"). Compiled by A. D. McNaught and A. Wilkinson. Blackwell Scientific Publications, Oxford (1997). XML on-line corrected version: http://goldbook.iupac.org (2006-) created by M. Nic, J. Jirat, B. Kosata; updates compiled by A. Jenkins. ISBN 0-9678550-9-8. doi:10.1351/goldbook.) Calcination is performed to decompose a metal salt and promote the exchange of metal ions within the catalyst and also to adhere the catalyst to a substrate. The temperatures used in calcination depend upon the components in the material to be calcined and generally are between about 400° C. to about 900° C. for approximately 1 to 24 hours. In some cases, calcination can be performed up to a temperature of about 1200° C. In applications involving the processes described herein, calcinations are generally performed at temperatures from about 400° C. to about 700° C. for approximately 1 to 8 hours, preferably at temperatures from about 400° C. to about 650° C. for approximately 1 to 4 hours.

In addition to removal of the structure directing agent, it is preferred that any alkaline or alkaline earth cations present be removed. Preferably, alkaline or alkaline earth cations can be removed with treatment with an acid or ammonia solution. This ion-exchange can be performed on an SDA containing intergrowth or a structure directing agent free intergrowth. The crystallinity of the material is better preserved when the alkaline or alkaline earth cations are removed in the SDA containing form.

One or more activated molecular sieves can be useful as a catalyst in certain applications. Activated intergrowth crystals are preferably calcined, but can also be used without calcination once the SDAs are removed. An activated molecular sieve can be used either without a post-synthesis metal exchange or with a post-synthesis metal exchange, preferably with a post-synthesis metal exchange. Thus, in certain aspects of the invention, provided is a catalyst comprising an activated molecular sieve that is free, or essentially free, of any exchanged metal, particularly post-synthesis exchanged or impregnated metals. The term "essentially free" of exchanged metals means that the metals are present at <0.1 wt. %. Activated intergrowths preferably comprise one or more catalytic metal ions exchanged or otherwise impregnated into the channels and/or cavities of the molecular sieve. Examples of metals that can be post-zeolite synthesis exchanged or impregnated include transition metals, including copper, nickel, zinc, iron, tungsten, molybdenum, cobalt, titanium, zirconium, manganese, chromium, vanadium, niobium, tin, bismuth, antimony, noble metals including platinum group metals (PGMs), such as ruthenium, rhodium, palladium, indium, platinum, and precious metals such as gold and silver; alkaline earth metals such as beryllium, magnesium, calcium, strontium, and barium; and rare earth metals such as lanthanum, cerium, praseodymium, neodymium, europium, terbium, erbium, ytterbium, and yttrium. Preferred transition metals for post-synthesis exchange are base metals, and preferred base metals include those selected from the group consisting of manganese, iron, cobalt, nickel, copper, noble metals including platinum group metals (PGMs) and mixtures thereof.

The transition metal can be present in an amount of about 0.1 to about 10 weight percent, for example about 0.1 to about 5 weigh percent, about 0.1 to about 1.0 weight percent, about 2.5 to about 3.5 weight percent, and about 4.5 to about 5.5 weight percent, wherein the weight percent is relative to the total weight of the molecular sieve material, and the endpoints can be included.

Particularly preferred exchanged metals include copper and iron, particularly when combined with calcium and/or cerium and particularly when the transition metals ($T_M$) and the alkaline metals ($A_M$) are present in a $T_M:A_M$ molar ratio of about 15:1 to about 1:1, for example about 10:1 to about 2:1, about 10:1 to about 3:1, or about 6:1 to about 4:1, where the endpoints can be included Metals incorporated post-synthesis can be added to the molecular sieve via any known technique such as ion exchange, impregnation, isomorphous substitution, etc.

These exchanged metal cations are distinct from metals constituting the molecular framework of the molecular sieve, and thus metal exchanged molecular sieves are distinct from metal-substituted molecular sieves.

JMZ-11A

The XRD pattern of SDA containing JMZ-11A was determined from a sample of Example 1. The X-ray diffraction pattern is shown in FIG. 1 and the peak values are summarized in Table 1. FIG. 1 shows the intensities normalized to a maximum peak height of 100%. This pattern and the peak values are characteristic of species of SDA containing JMZ-11.

When the molecular sieve is an aluminosilicate and the structure directing agent comprises a N,N-dimethyl-3,5-dimethylpiperidinium cation, a powder XRD pattern of hydrated aluminosilicate JMZ-11A can have the characteristic lines with the corresponding intensities as shown in Table 1.

TABLE 1

| 2-Theta [°] (a) | d-spacing [Å] | Rel. Int. [%] (b) |
|---|---|---|
| 7.7 | 11.47 | vs |
| 9.6 | 9.17 | w |
| 11.8 | 7.51 | m |
| 13.1 | 6.74 | s |
| 15.2 | 5.84 | m |
| 17.6 | 5.04 | m |
| 18.0 | 4.92 | vs |
| 20.0 | 4.44 | s |
| 21.0 | 4.23 | w |
| 21.9 | 4.06 | vs |
| 22.6 | 3.93 | w |
| 26.2 | 3.40 | s |
| 27.3 | 3.27 | w |
| 28.1 | 3.18 | m |
| 28.7 | 3.11 | w |
| 30.3 | 2.95 | s |
| 31.0 | 2.89 | m |
| 31.6 | 2.83 | m |
| 33.7 | 2.66 | w |
| 34.8 | 2.58 | m |
| 43.7 | 2.07 | w |
| 48.0 | 1.89 | w |

(a) = ±0.2;
(b) Peaks with Rel. Int. <5% are not listed

The term "Rel. Int." (Relative Intensity" refers to designations based on the relative intensity ($100 \times I/I_0$), where the labels are defined as: w (weak)<20; m (medium) is ≥20 and <40; s (strong) is ≥40 and <60; and vs (very strong) is ≥60.

Figure 2:
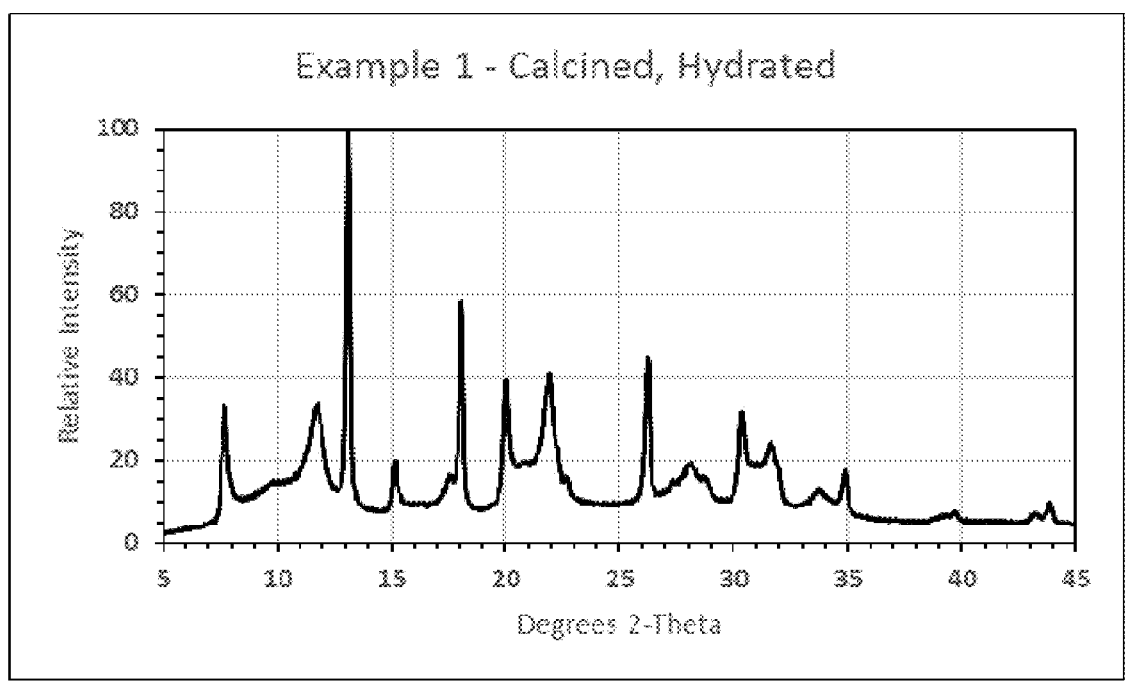
FIG. 2 is a powder XRD pattern of activated (calcined) H-JMZ-11A with normalized intensities.

In a second aspect of the invention, JMZ-11A is present in an activated form. The XRD pattern of activated JMZ-11A was determined from a sample of Example 1. The X-ray diffraction pattern is shown in FIG. 2 and the peak values are summarized in Table 2. FIG. 2 shows intensities normalized to a maximum peak height of 100%. This pattern and the peak values are characteristic of species of activated JMZ-11.

TABLE 2

| 2θ [°] (a) | d-spacing [Å] | Rel. Int. [%] (b) |
|---|---|---|
| 7.7 | 11.49 | m |
| 9.6 | 9.20 | w |
| 11.7 | 7.53 | m |
| 13.1 | 6.74 | vs |
| 15.2 | 5.84 | w |
| 17.6 | 5.03 | w |
| 18.1 | 4.91 | s |
| 20.0 | 4.43 | m |
| 20.8 | 4.26 | w |
| 21.9 | 4.05 | m |

TABLE 2-continued

| 2θ [°] (a) | d-spacing [Å] | Rel. Int. [%] (b) |
|---|---|---|
| 22.7 | 3.92 | w |
| 26.2 | 3.39 | m |
| 27.4 | 3.25 | w |
| 28.1 | 3.17 | w |
| 28.7 | 3.11 | w |
| 30.4 | 2.94 | m |
| 31.0 | 2.88 | w |
| 31.6 | 2.83 | w |
| 33.8 | 2.65 | w |
| 34.9 | 2.57 | w |
| 43.9 | 2.06 | w |
| 48.1 | 1.89 | w |

(a) = ±0.2;
(b) Peaks with Rel. Int. <5% are not listed

JMZ-11B

Figure 3:
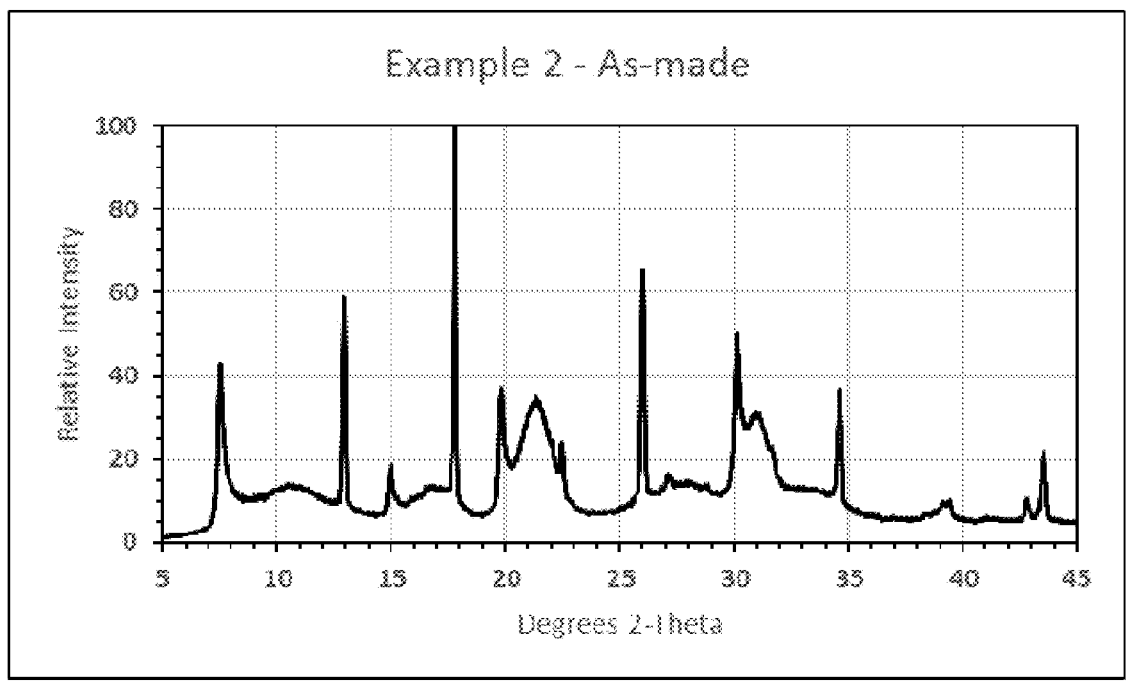
FIG. 3 is a powder XRD pattern of SDA containing (as-made) JMZ-11B with normalized intensities.

The XRD pattern of SDA containing JMZ-11B was determined from a sample of Example 2. The X-ray diffraction pattern is shown in FIG. 3 and the peak values are summarized in Table 3. FIG. 3 shows the intensities normalized to a maximum peak height of 100%. This pattern and the peak values are characteristic of species of SDA containing JMZ-11B.

When the molecular sieve is an aluminosilicate and the structure directing agent comprises a N,N-diethyl-2,6-dimethylpiperidinium cation, a powder XRD pattern of hydrated aluminosilicate JMZ-11B can have the characteristic lines with the corresponding intensities as shown in Table 3.

TABLE 3

| 2-Theta [°] (a) | d-spacing [Å] | Rel. Int. [%] |
|---|---|---|
| 7.5 | 11.71 | m-s |
| 10.5 | 8.43 | w |
| 12.9 | 6.84 | s-vs |
| 15.0 | 5.90 | w |
| 17.8 | 4.98 | vs |
| 19.8 | 4.47 | m |
| 21.3 | 4.17 | m |
| 21.9 | 4.05 | w-m |
| 22.5 | 3.96 | w-m |
| 26.0 | 3.42 | s-vs |
| 27.1 | 3.28 | w |
| 28.0 | 3.18 | w |
| 30.2 | 2.96 | m-s |
| 31.0 | 2.88 | m |
| 31.6 | 2.83 | w |
| 34.6 | 2.59 | m |
| 43.5 | 2.08 | w-m |
| 47.8 | 1.90 | w |

(a) = ±0.2;
(b) Peaks with Rel. Int. <5% are not listed

Figure 4:
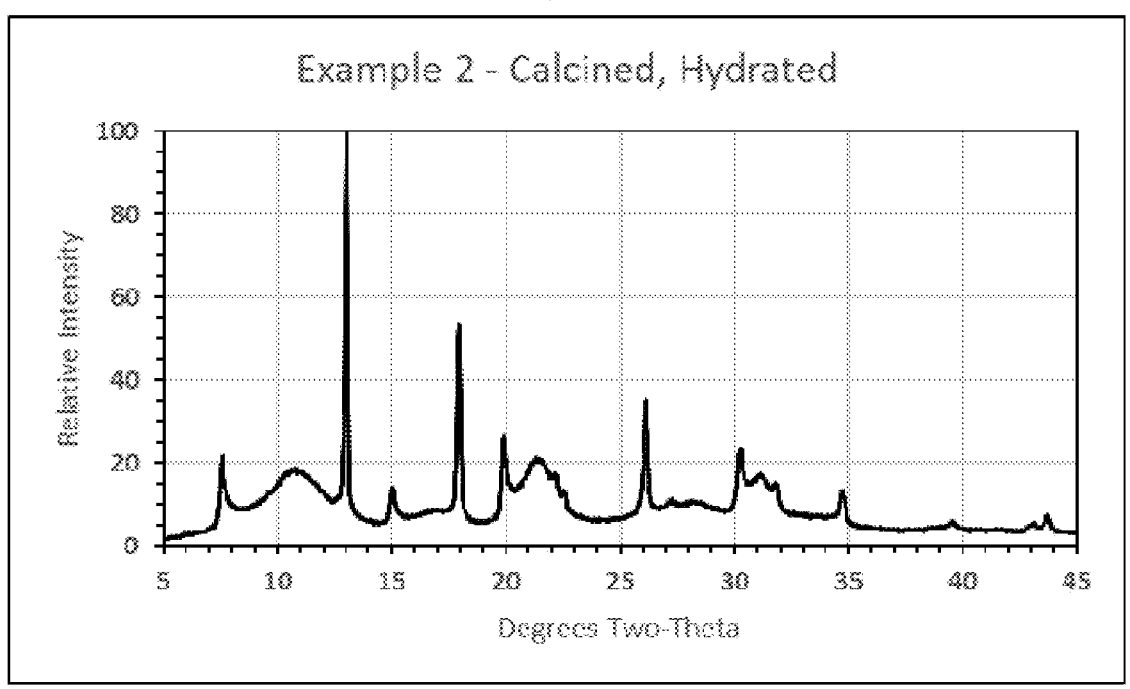
FIG. 4 is a powder XRD pattern of activated (calcined) H-JMZ-11B with normalized intensities.

In a second aspect of the invent, JMZ-11B is present in an activated form. The XRD pattern of activated JMZ-11B was determined from a sample of Example 2. The X-ray diffraction pattern is shown in FIG. 4 and the peak values are summarized in Table 4. FIG. 4 shows the intensities normalized to a maximum peak height of 100%. This pattern and the peak values are characteristic of species of activated JMZ-11B.

TABLE 4

| 2-Theta [°] (a) | d-spacing [Å] | Rel. Int. [%] (b) |
|---|---|---|
| 7.6 | 11.65 | w-m |
| 10.8 | 8.22 | w |
| 13.0 | 6.80 | vs |

TABLE 4-continued

| 2-Theta [°] (a) | d-spacing [Å] | Rel. Int. [%] (b) |
|---|---|---|
| 15.1 | 5.88 | w |
| 17.9 | 4.94 | s |
| 19.9 | 4.45 | w-m |
| 21.4 | 4.15 | w-m |
| 22.1 | 4.02 | w |
| 22.5 | 3.94 | w |
| 26.1 | 3.41 | m |
| 27.2 | 3.27 | w |
| 28.1 | 3.17 | w |
| 30.3 | 2.95 | w-m |
| 31.1 | 2.87 | w |
| 31.8 | 2.81 | w |
| 34.7 | 2.58 | w |
| 43.7 | 2.07 | w |
| 48.0 | 1.90 | w |

(a) = ±0.2;
(b) Peaks with Rel. Int. <5% are not listed

JMZ-11C

Figure 5:
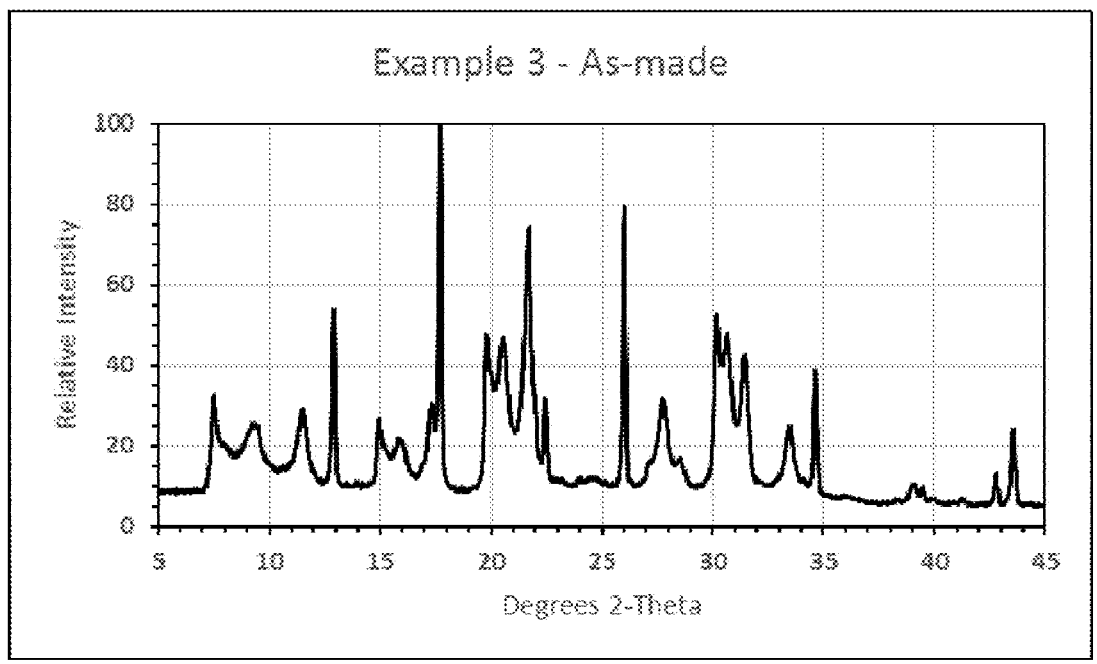
FIG. 5 is a powder XRD pattern of SDA containing (as-made) JMZ-11C with normalized intensities.

The XRD pattern of SDA containing JMZ-11C was determined from a sample of Example 3. The X-ray diffraction pattern is shown in FIG. 5 and the peak values are summarized in Table 5. FIG. 5 shows the intensities normalized to a maximum peak height of 100%. This pattern and the peak values are characteristic of species of SDA containing JMZ-11C.

When the molecular sieve is an aluminosilicate and the structure directing agent comprises N,N-dimethyl-3,5-dimethylpiperidinium cations and 1,3-bis(1-adamantyl) imidazolium cations, a powder XRD pattern of hydrated aluminosilicate JMZ-11C can have the characteristic lines with the corresponding intensities as shown in Table 5.

TABLE 5

| 2-Theta [°] (a) | d-spacing [Å] | Rel. Int. [%] (b) |
|---|---|---|
| 7.5 | 11.86 | w |
| 8.1 | 10.92 | w |
| 9.2 | 9.61 | w |
| 11.6 | 7.62 | m |
| 12.9 | 6.85 | vs |
| 17.4 | 5.08 | w |
| 17.9 | 4.95 | s |
| 19.8 | 4.47 | w |
| 20.5 | 4.32 | w |
| 21.8 | 4.08 | m |
| 22.2 | 4.01 | w |
| 26.0 | 3.42 | m |
| 28.1 | 3.18 | w |
| 30.2 | 2.95 | w |
| 30.6 | 2.92 | w |
| 31.5 | 2.84 | w |
| 31.8 | 2.81 | w |
| 34.7 | 2.58 | w |

(a) = ± 0.2;
(b) Peaks with Rel. Int. < 5% are not listed

Figure 6:
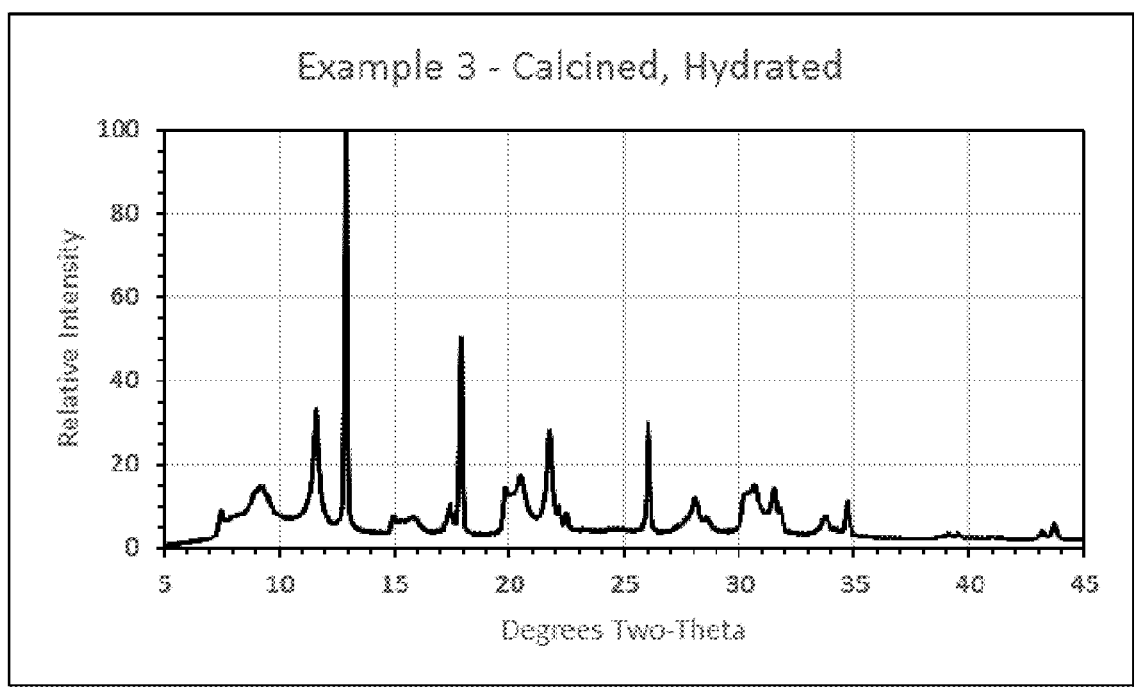
FIG. 6 is a powder XRD pattern of activated (calcined) H-JMZ-11C with normalized intensities.

In a second aspect of the invent, JMZ-11C is present in an activated form. The XRD pattern of activated JMZ-11C was determined from a sample of Example 3. The X-ray diffraction pattern is shown in FIG. 6 and the peak values are summarized in Table 6. FIG. 6 shows the intensities normalized to a maximum peak height of 100%. This pattern and the peak values are characteristic of species of activated JMZ-11C.

TABLE 6

| 2-Theta [°] (a) | d-spacing [Å] | Rel. Int. [%] (b) |
|---|---|---|
| 7.5 | 11.75 | m |
| 8.0 | 11.03 | w |
| 9.4 | 9.41 | w |
| 11.5 | 7.68 | w-m |
| 12.9 | 6.86 | s |
| 15.0 | 5.91 | w-m |
| 15.9 | 5.57 | w |
| 17.4 | 5.11 | m |
| 17.7 | 5.00 | vs |
| 19.8 | 4.48 | s |
| 20.6 | 4.32 | m-s |
| 21.7 | 4.09 | vs |
| 22.5 | 3.96 | w-m |
| 26.0 | 3.41 | m |
| 27.2 | 3.27 | w |
| 27.8 | 3.21 | m |
| 28.5 | 3.13 | w |
| 30.2 | 2.96 | s |
| 30.6 | 2.92 | s |
| 31.4 | 2.85 | m-s |
| 33.5 | 2.68 | w |
| 34.6 | 2.59 | m |
| 42.8 | 2.11 | w |
| 43.6 | 2.08 | w-m |

(a) = ±0.2;
(b) Peaks with Rel. Int. <5% are not listed

JMZ-11D

Figure 7:
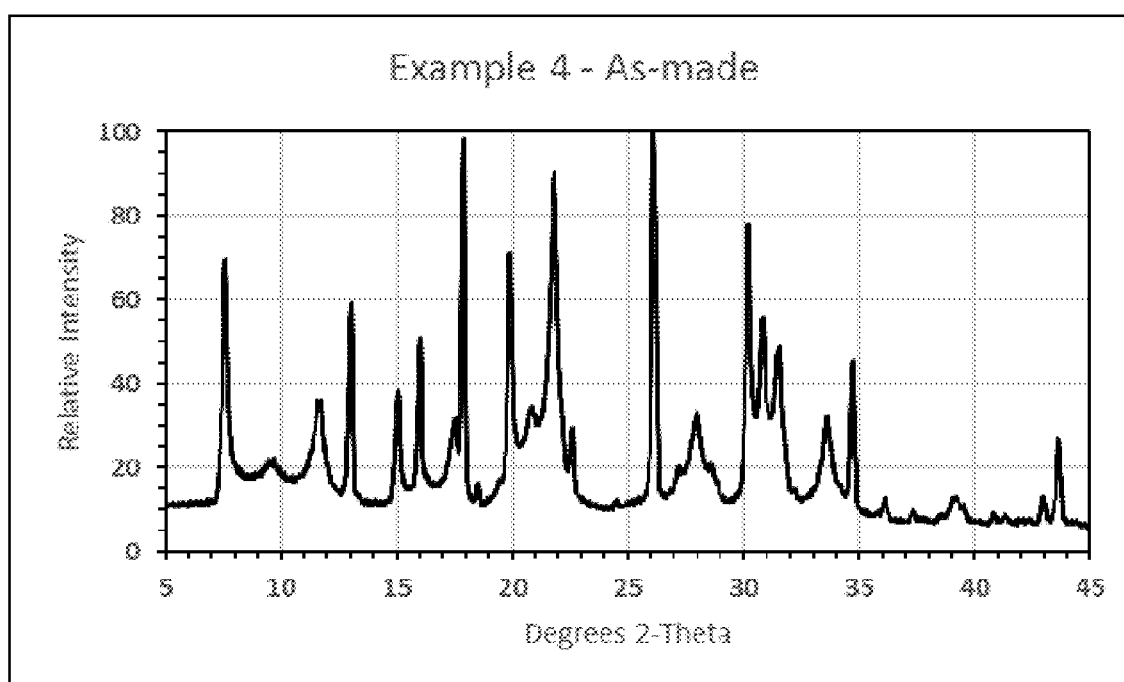
FIG. 7 is a powder XRD pattern of SDA containing (as-made) JMZ-11D with normalized intensities.

The XRD pattern of SDA containing JMZ-11D was determined from a sample of Example 4. The X-ray diffraction pattern is shown in FIG. 7 and the peak values are summarized in Table 7. FIG. 7 shows the intensities normalized to a maximum peak height of 100%. This pattern and the peak values are characteristic of species of SDA containing JMZ-11B.

When the molecular sieve is an aluminosilicate and the structure directing agent comprises a N,N-dimethyl-3,5-dimethylpiperidinium and trimethyladmandylammonium cations, a powder XRD pattern of hydrated aluminosilicate JMZ-11D can have the characteristic lines with the corresponding intensities as shown in Table 7.

TABLE 7

| 2-Theta [°] (a) | d-spacing [Å] | Rel. Int. [%] (b) |
|---|---|---|
| 7.6 | 11.66 | m |
| 9.7 | 9.1 | w |
| 11.6 | 7.59 | m |
| 13 | 6.79 | vs |
| 15.1 | 5.88 | w |
| 17.5 | 5.06 | w |
| 17.9 | 4.95 | s |
| 19.9 | 4.45 | m |
| 20.8 | 4.26 | w |
| 21.8 | 4.07 | m |
| 22.6 | 3.93 | w |
| 26.1 | 3.41 | m |
| 28 | 3.19 | w |
| 30.3 | 2.95 | w-m |
| 30.9 | 2.89 | w |
| 31.6 | 2.83 | w |
| 34.8 | 2.58 | w |

(a) = ±0.2;
(b) Peaks with Rel. Int. <5% are not listed

Figure 8:
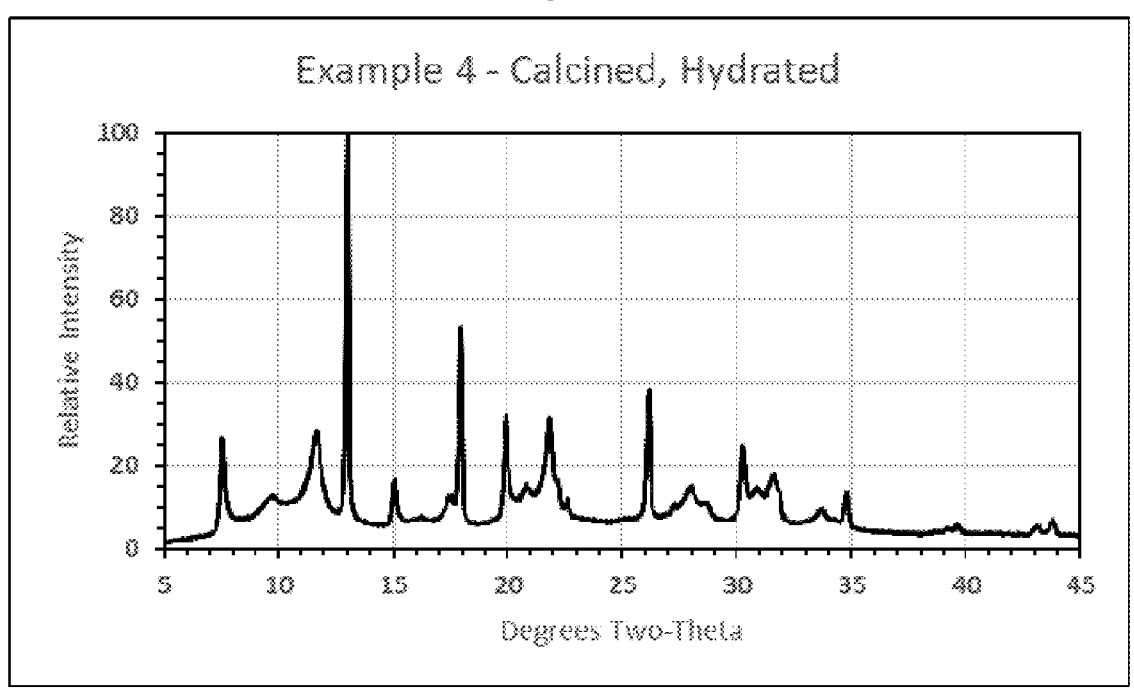
FIG. 8 is a powder XRD pattern of activated (calcined) H-JMZ-11D with normalized intensities.

In a second aspect of the invent, JMZ-11D is present in an activated form. The XRD pattern of activated JMZ-11D was determined from a sample of Example 4. The X-ray diffraction pattern is shown in FIG. 8 and the peak values are summarized in Table 8. FIG. 8 shows the intensities normalized to a maximum peak height of 100%. This pattern and the peak values are characteristic of species of activated JMZ-11D.

TABLE 8

| 2-Theta [°] [a] | d-spacing [Å] | Rel. Int. [%] [b] |
|---|---|---|
| 7.6 | 11.66 | m |
| 9.7 | 9.10 | w |
| 11.6 | 7.59 | m |
| 13.0 | 6.79 | vs |
| 15.1 | 5.88 | w |
| 17.5 | 5.06 | w |
| 17.9 | 4.95 | s |
| 19.9 | 4.45 | m |
| 20.8 | 4.26 | w |
| 21.8 | 4.07 | m |
| 22.2 | 4.00 | w |
| 26.1 | 3.40 | m |
| 28.0 | 3.19 | w |
| 30.3 | 2.95 | w-m |
| 30.9 | 2.89 | w |
| 31.6 | 2.83 | w |
| 31.8 | 2.80 | w |
| 34.8 | 2.58 | w |

[a] = ±0.2;
[b] Peaks with Rel. Int. <5% are not listed

Methods of Analyzing Intergrowth

The molecular sieves described herein represent a family of molecular sieves comprising intergrowths of cha and aft having an "sfw-GME tail". This will be defined fully below but these differ from stochastic intergrowths of CHA and GME such as babelite. They also differ from stochastic intergrowths of CHA and AFX or CHA and AFT which have no cavities larger that aft. The intergrowths described herein belong to the ABC-6 family of zeolites, specifically only those with a stacking sequence consisting of only double-6 rings (D6R).

The intergrowth can form different structures within the bulk molecular sieve. This can result in the appearance of a separate phase recognized by XRD. The relative proportions of each of the intergrowth phases can be analyzed by x-ray diffraction and, in particular, by comparing the observed patterns with calculated patterns generated using algorithms to simulate the effects of stacking disorder.

DIFFaX is a fortran computer program based on a mathematical model for calculating intensities from crystals containing planar faults (Treacy, M. M. J.; Newsam, J. M.; Deem, M. W.: A general recursion method for calculating diffracted intensities from crystals containing planar faults. Proc. R. Soc. London Ser. A 433 (1991) 499-520).

DIFFaX is the simulation program selected by, and available from, the International Zeolite Association to simulate the powder XRD patterns for randomly intergrown phases (see "Collection of Simulated XRD Powder Patterns for Zeolites," Fifth Revised Edition, Elsevier, 2007, published on behalf of the Structure Commission of the International Zeolite Association). DIFFaX has been used to theoretically study zeolite beta (Treacy et al 1991), AEI-CHA intergrowths in numerous patents and many other intergrowths in zeolites and other materials.

Figure 10:
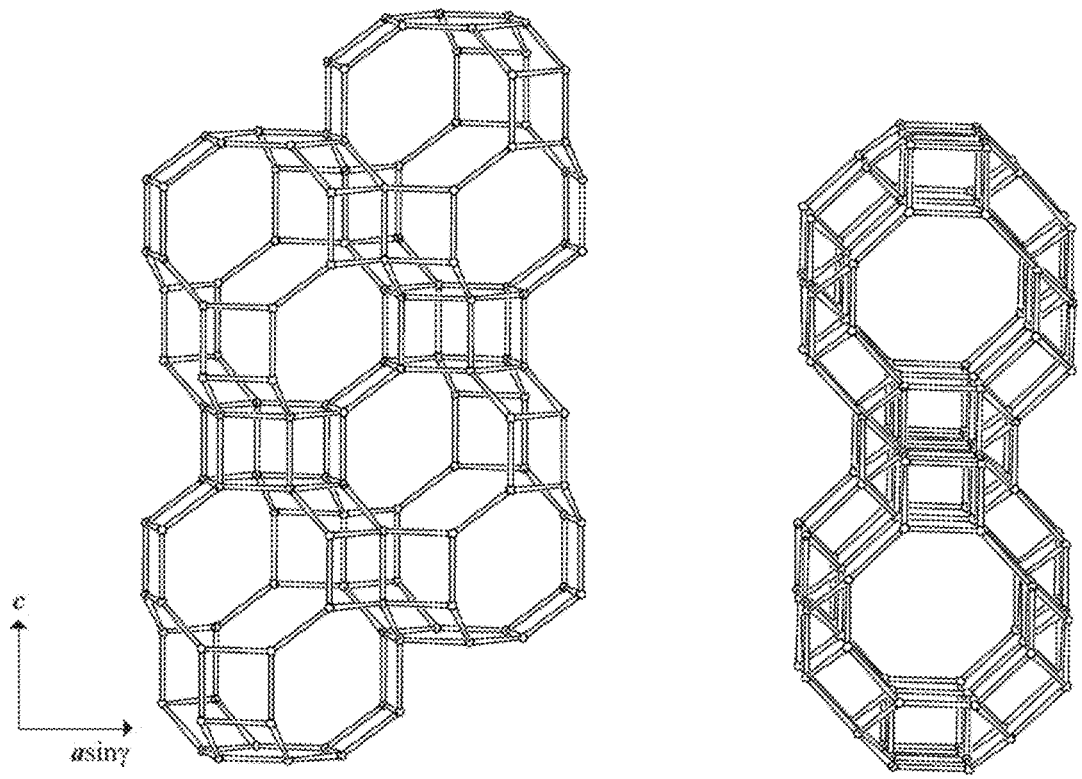
FIG. 10 is a representation of the CHA building scheme from IZA.

Pure CHA has a 3-dimensional pore system with cha cavities linked by 8-rings windows forming 8-ring channels. (FIG. 10)

Pure GME has a 3-dimensional pore system with gme cavities linked by 8-rings to 12-ring channels that runs through the entire length of a crystallite in the c-axis direction. (FIG. 11)

Intergrowths of CHA and GME are well known. In a CHA-GME intergrowth, the CHA units block off the ends of the 12-ring channels and the resulting GME units can have cavities from as small as aft to almost the crystal length in the direction of the c-axis (as well as associated gme cavities). The cavities in this system can be described using an integer that is proportional to its length in the c-direction: 1=gme, 2=cha, 3=aft, 4=sfw, 5="5", 6="6", etc. Hereafter, the gme cavities are ignored as they are implicitly present in respect to the larger cavities (1 per aft, 2 per sfw, 3 per "5", etc or (n−2) per "n" cavity for n>2). The gme cavities provide the framework that links the aft and larger cavities to one another in the basal plane directions. CHA units have cavities of size 2 and what is called GME in the intergrowth has cavity sizes that can range from 3 to "infinity" depending on how soon another fault closes off the 12-ring channel.

The stochastic intergrowth model for DIFFaX input is shown in FIG. 12 has individual layers 5 Angstrom thick, as enumerated in the CHA-GME file in the Examples folder on Mike Treacy's DIFFaX website. (http://www.public.as-u.edu/%7Emtreacy/DIFFaX.html). The basis of each layer is the top 6-ring of a double 6-ring linked to the bottom 6-ring of an adjacent double 6-ring. The forward slash and backslash lines in the schematic of the stacking in FIG. 13 represent the direction of this linkage. The 6-rings are omitted for simplicity. Forward slash indicates AB, BC or CA stacking whilst backslash indicates AC, CB or BA stacking in theses ABC double 6-ring materials.

CHA-GME intergrowths that have been described in the literature have essentially a stochastic intergrowth wherein one fault probability, p, describes the distribution of cavity sizes in the material. Analysis of this model leads to a monotonically decreasing fractional population, f, of cavities with size, n; one in which $$f_{n+1} = pf_n \text{ for } n \geq 2 \text{ and } f_2 = (1-p).$$

Figures 14, 15:
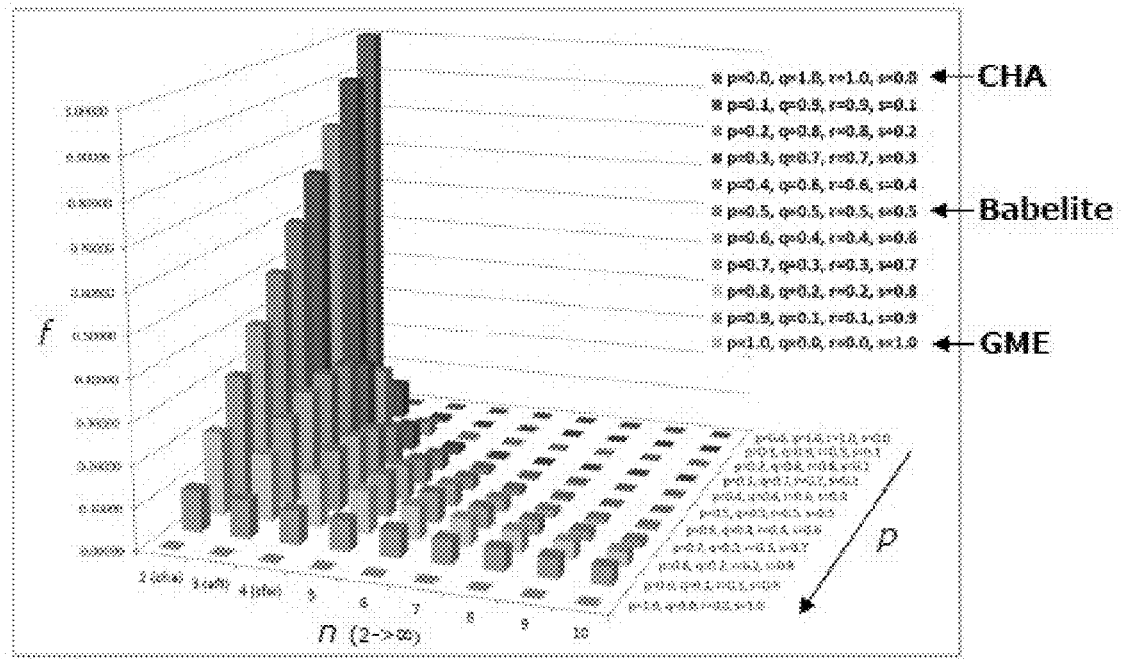
FIG. 14 is a transition probability matrix for a Reichweite 2 description where previous two 5 Angstrom thick layers influence the stacking probability.
FIG. 15 is a diagram showing the cage distribution for a simple stochastic CHA-GME framework intergrowth (equivalent to Reichweite 0).

An example of this is given by Babelite which has p=0.5. (R. Szostak, K. P. Lillerud, J. Chem. Soc., Chem. Commun. 1994, 2357). The range of distributions as a function of p is shown in FIG. 14.

In stochastic intergrowths, only the identity of the current layer determines the stacking probability of the next layer; there is no memory effect of the previous layer. The Treacy et al paper includes the memory or Reichweite concept to describe clustering of faults (or block intergrowths) by including the influence of the previous layer on the stacking probability of the next (known as Reichweite 1). This is also shown in FIG. 13. For example, if p is small large blocks of CHA would alternate with GME like large cavities.

The extension to Reichweite n wherein the current layer and previous n layers influence the next layer is straightforward and has been described by H. Jagodzinski, Acta Cryst. 2 208-14 (1949). The essential features of the intergrowths in this application can be described by a Reichweite 2 DIFFaX model (FIG. 15). In the case of Reichweite 2, the stacking probability of a new layer in the crystallographic c-axis depends on the stacking of the previous 2 layers. The forward-slashes and back-slashes in parenthesis in FIG. 15 indicate the stacking of the 2 previous layers. Layer type 1 followed by Layer 1 is a CHA stacking sequence and Layer 3 followed by Layer 6 is part of a GME sequence. Although this model considers only the framework directly and not the structure directing agent molecules, it nevertheless is a reasonable descriptor.

This is because the Reichweite 2 DIFFaX model explicitly generates cha, aft and sfw cavities with the associated gme cavities for aft and sfw. All of the known, ordered ABC-6, double 6-ring frameworks are included in the description—CHA, AFT, AFX and SFW. The stacking probabilities p, q, r, and s are defined in the 8×8 matrix below and all have values in the range 0 to 1. The entries in the row, m, of the matrix are the probabilities that Layer m will be followed by Layer in column n. The sequence of Layers and the corresponding values of the stacking probabilities p, q, r, s for the known ordered phases are listed.

Figure 16:
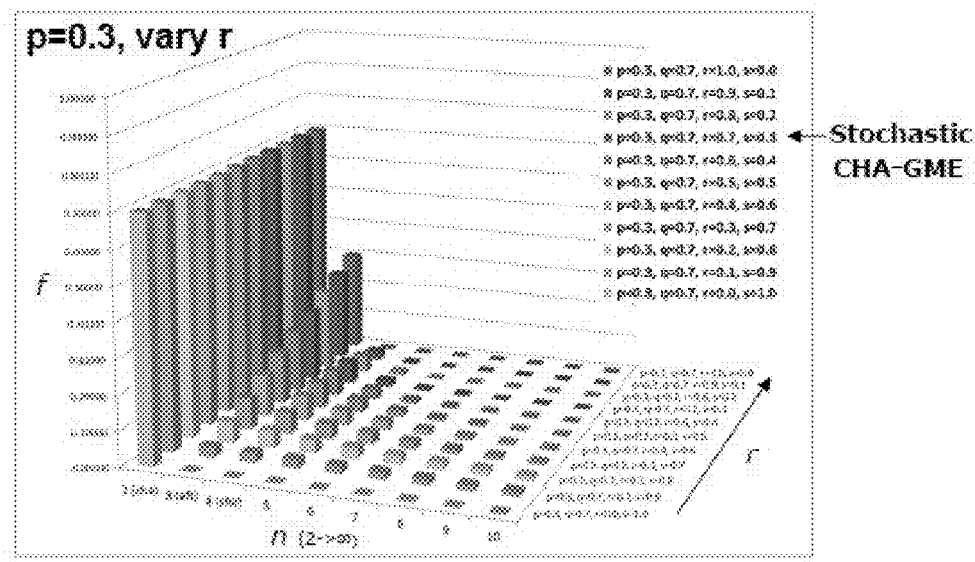
FIG. 16 is a diagram showing the cage distribution for a simple "block" intergrowth of CHA and GME.

In the general case it is straightforward to calculate from the stacking probabilities the distribution of cavity sizes, $f_n$, ignoring the gme cavities as they are in strict relation to the larger cavities. (FIG. 16)

If r=1, there are no cavities larger than sfw. If s=0 there are no sfw cavities and there is no "sfw-GME" tail. So, if r=1 and s=0, there is either a stochastic CHA-AFX intergrowth if q=(1−p) or a stochastic CHA-AFT intergrowth if q=1. But, in terms of the model, q need not be so constrained. Hence the concept of cha-aft intergrowths containing local regions of CHA, AFT and AFX.

If s>0 there is an "sfw-GME" tail such that:

$$f_{n+1} = pf_n \text{ but only for } n >= 4$$

similar to the distribution for stochastic CHA-GME but with sfw rather than cha as the smallest cavity (ignoring the associated gme cavities). The probability r controls the length of the tail, that is how quickly the distribution drops off with increasing cavity size. As r approaches zero the "sfw-GME" tail extends to larger cavities. The number fraction of cha cavities is q/(p+q), of aft cavities is p(1−s)/(p+q) and of cavities in the "sfw-GME" tail ps/(p+q). Note these fractions are independent of the probability r that controls the length of the tail. But the diffraction pattern is dependent on these and r.

Figure 17:
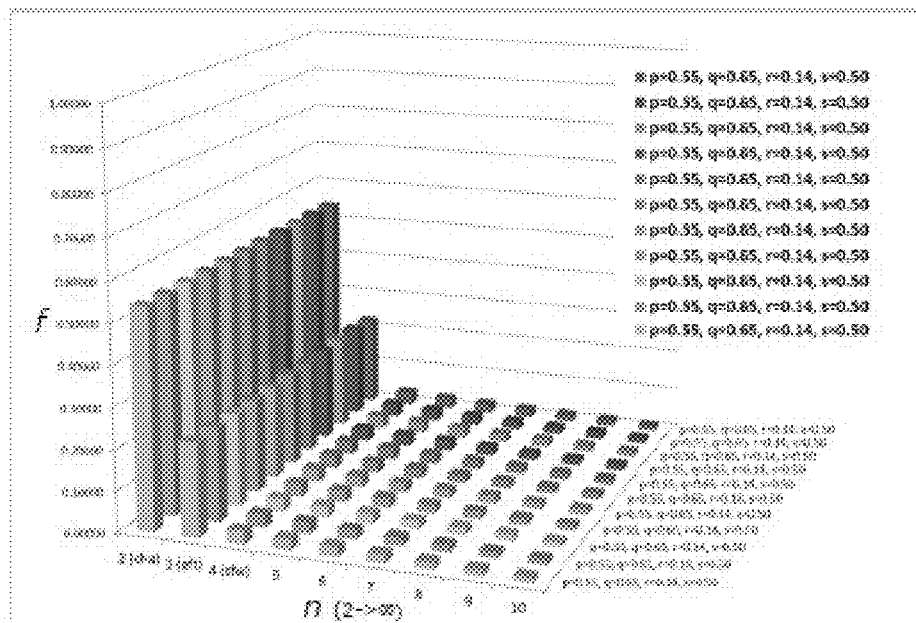
FIG. 17 is a diagram showing the cage distribution for a cha-aft-"sfw-GME" tail intergrowths in Example 1 (JMZ-11A).
Figure 18:
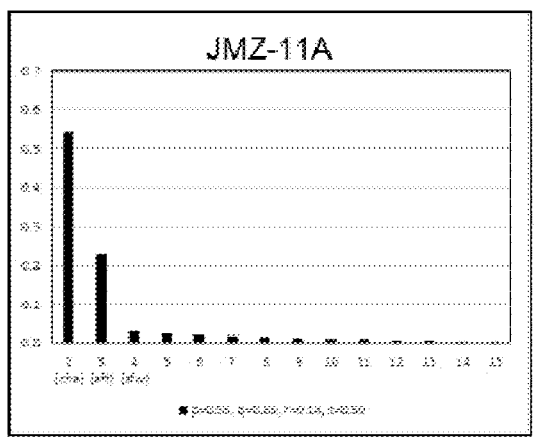
FIG. 18 to 21 show the cage distribution within JMZ-11A, JMZ-11B, JMZ-11C and JMZ-11D.
Figure 19:
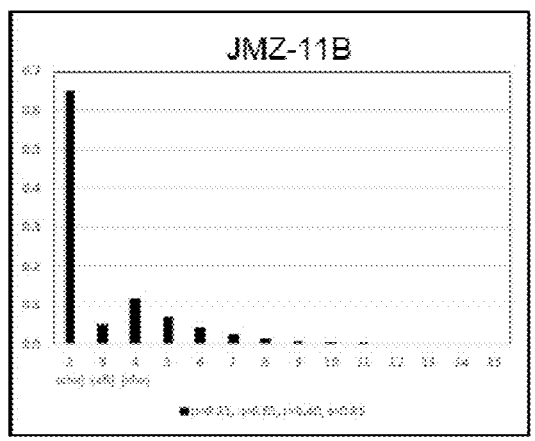
Figure 20:
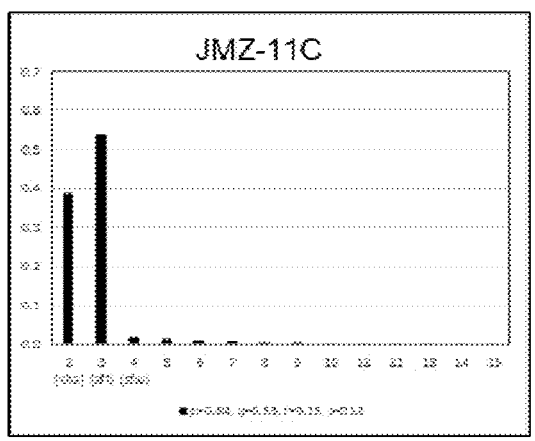
Figure 21:
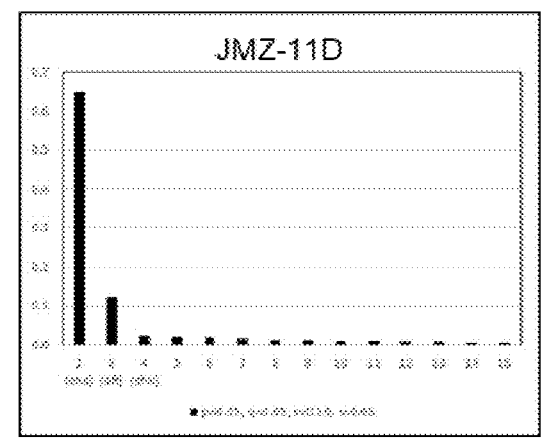
Figure 22:
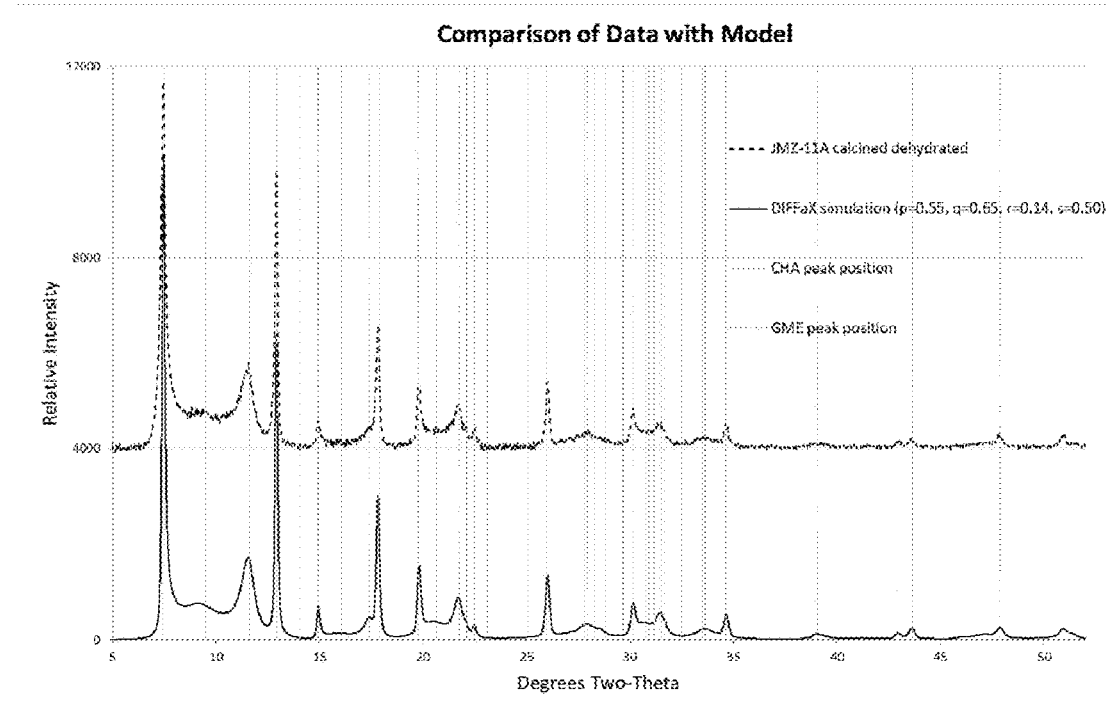
FIGS. 22-25 show the comparison between the experimental XRD patterns of activated JMZ-11A, JMZ-11B, JMZ-11C, and JMZ-11D and the DIFFaX simulations carried out using the Reichweite 2 description.
Figure 23:
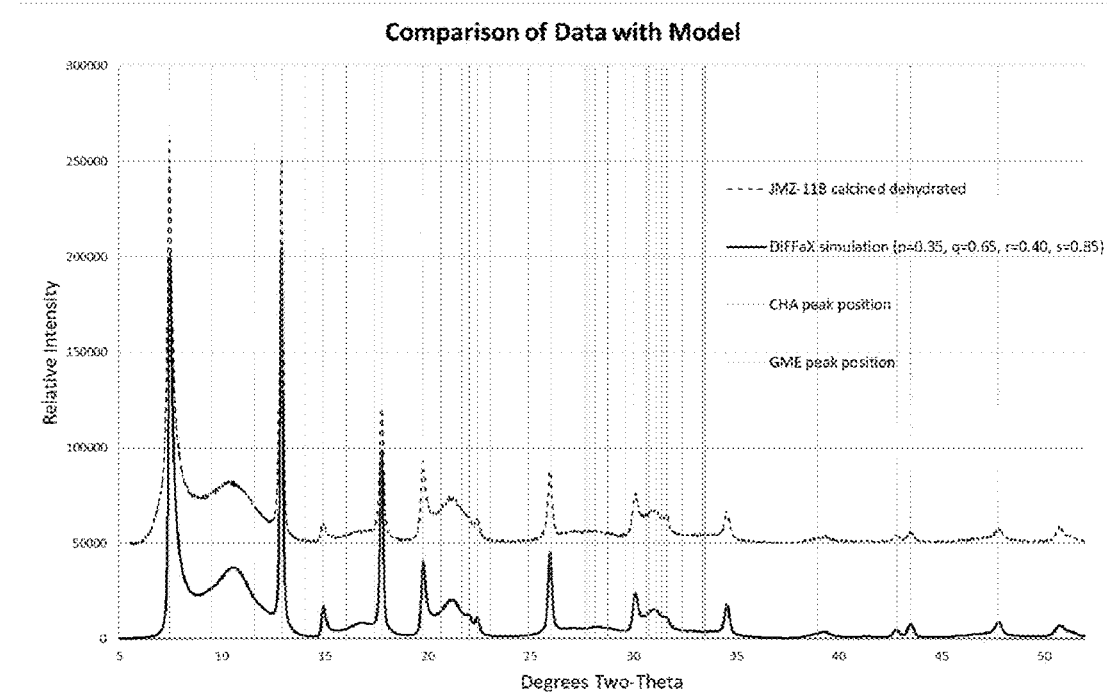
Figure 24:
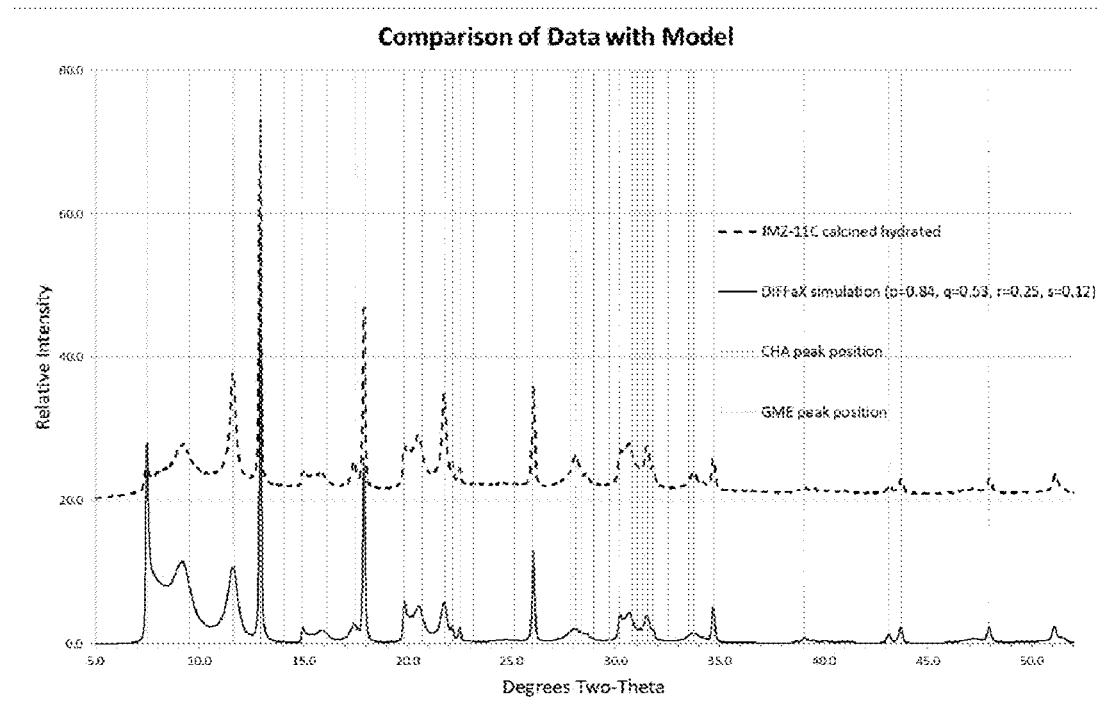
Figure 25:
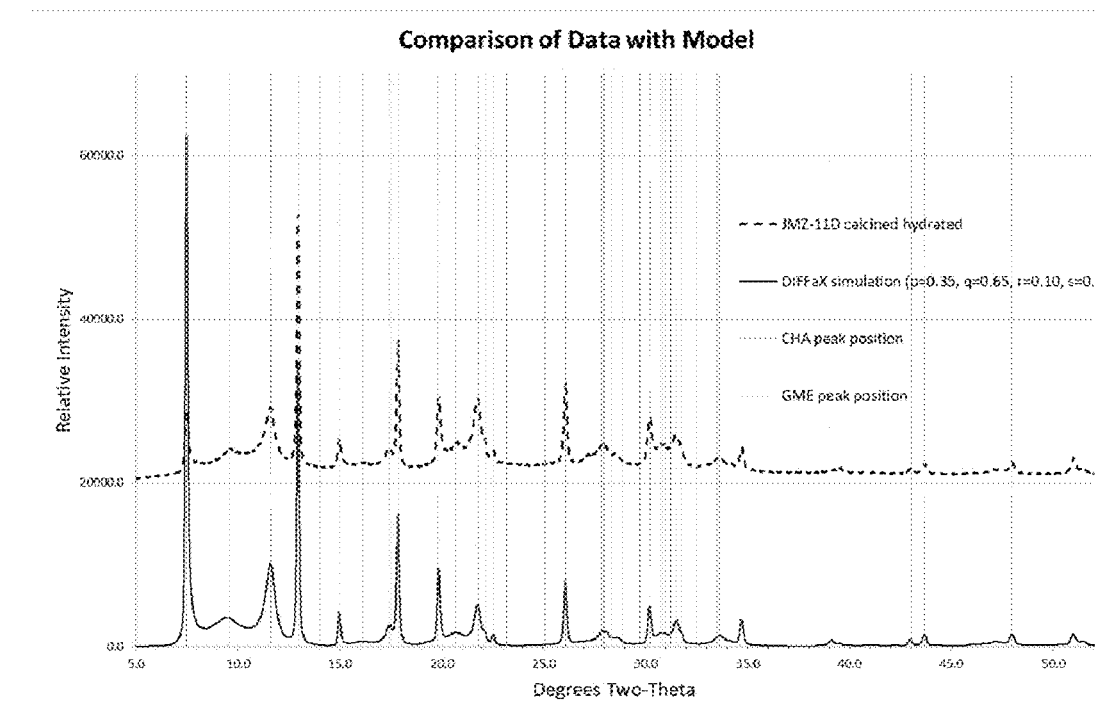

However, if s=(1−r)=p and q=(1−p), these equations reduce to $f_{n+1}=pf_n$ for n>=2, with $f_2=(1-p)$. In this situation there is no memory effect (Reichweite 0) and this results in a stochastic CHA-GME intergrowth (FIG. 17) in which the stacking probability of a layer is independent of the previous stacking. The larger the value of p, the smaller the percentage of cha cavities and the larger the average non-gme cavity size as demonstrated in FIG. 17. Note that if gme cavities are included the average cavity size for all ABC-6 d6R materials (ordered or disordered) is precisely 2.

JMZ-11A, JMZ-11B, JMZ-11C and JMZ-11D are not stochastic intergrowths of CHA-GME. They are best described as cha-aft-"sfw-GME" intergrowths, which can be described by the Reichweite 2 model. The three materials comprise a monotonically decreasing sfw-GME tail encompassing the range from sfw cages to "infinity", while the cha and aft cages are in very different proportions relative to this tail than those in stochastic CHA-GME intergrowths. The cage distributions within JMZ-11A, JMZ-11B, JMZ-11C and JMZ-11D as determined by the above analysis are shown in FIG. 18 to 21, respectively.

The use of lower case cha and aft here is to include local AFX and AFT regions in the intergrowths. Stochastic CHA-AFX intergrowths will inevitably have local regions of AFT; with more AFT than AFX when the probability of CHA faulting is small. However, a CHA-AFT stochastic intergrowth would have no local AFX regions, and simulated x-ray diffraction (using DIFFaX) patterns are different. Stochastic CHA-AFX and CHA-AFT intergrowths are subsets of more general cha-aft intergrowths.

The "sfw-GME" tail is a significant fraction of the volume in these cha-aft-"sfw-GME" intergrowths that cannot be ignored. CHA-AFT and CHA-AFX (or more generally cha-aft) intergrowths do not have such a tail—there are no cavities larger than aft. The X-ray diffraction patterns of these cha-aft-"sfw-GME" materials cannot be approximated without the "sfw-GME" tail. Annular dark-field images recorded by aberration-corrected Scanning Transmission Electron Microscopy confirms this model.

FIGS. 22-25 show comparisons between the experimental XRD patterns of activated JMZ-11A, JMZ-11B, JMZ-11C, and JMZ-11D and the DIFFaX simulations carried out using the Reichweite 2 description. This figures show that the DIFFaX simulations carried out using the Reichweite 2 description provide a good description of the composition of the intergrowths.

Figure 9:
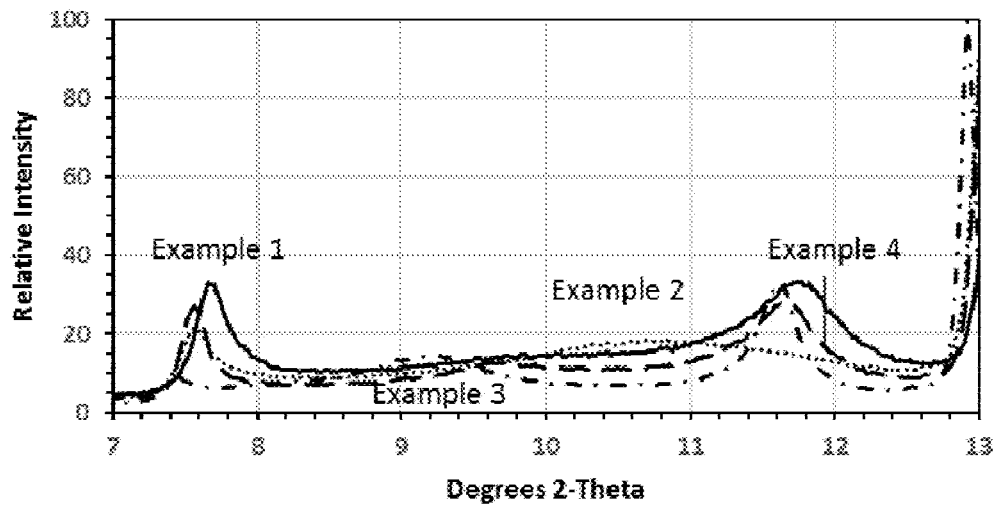
FIG. 9 shows the powder XRD patterns of calcined H-JMZ-11A to H-JMZ11D with normalized intensities shown at from 7 to 13 degrees 2-theta.

In powder XRD patterns from stochastic CHA-GME intergrowths the peak at 9.5 degrees broadens but does not shift. In the JMZ-11 family, which comprises JMZ-11A, JMZ-11B, JMZ-11C and JMZ-11D, this peak shift substantially from 9.5 degrees but the broadening of it and the raised background between 7.7 and 13.1 degrees are much greater than in stochastic CHA-GME intergrowths (FIG. 9). The sfw-GME tail must be included to simulate this correctly for dehydrated, activated samples.

JMZ-11A comprises a structure direct agent (SDA-1), where SDA-1 is a N,N-dimethyl-3,5-dimethylpiperidinium cation, cha cavities, aft cavities and an "sfw-GME" tail, wherein the cha cavities are present at about 45 to about 65%, preferably about 54%, of the cavities in the tail, the aft cavities are present at about 18 to about 28%, preferably about 23% of the cavities in the tail, and the remaining about 7 to about 37%, preferable about 23%, of larger cavities in the "sfw-GME" tail. The gme cavities associated with the aft and larger cavities are not included in these figures. The "sfw-GME" tail accounts for about 35-80% of the volume of the molecular sieve or the molecular sieve particle, preferably about 68%. JMZ-11A has a monotonically decreasing distribution of cavity sizes, but it cannot be described as a stochastic CHA-GME intergrowth.

JMZ-11B comprises a structure direct agent (SDA-1), where SDA-1 is a N,N-diethyl-2,6-dimethylpiperidinium cation, cha cavities, aft cavities and an "sfw-GME" tail, wherein the cha cavities are present at about 55 to about 75%, preferably about 65%, of the cavities in the tail, the aft cavities are present at about 0 to about 10%, preferably about 5% of the cavities in the tail, and the remaining about 15 to about 45%, preferable about 30%, of larger cavities in the "sfw-GME" tail. The gme cavities associated with the aft and larger cavities are not included in these figures. The "sfw-GME" tail accounts for about 40-80% of the volume of the molecular sieve or the molecular sieve particle, preferably about 64%. JMZ-11B has a monotonically decreasing distribution of cavity sizes, but it cannot be described as a stochastic CHA-GME intergrowth.

JMZ-11C comprises two structure direct agents, an N,N-dimethyl-3,5-dimethylpiperidinium cation and a 1,3-bis(1-adamantyl)imidazolium cation, cha cavities, aft cavities and an "sfw-GME" tail, wherein the cha cavities are present at about 30 to about 45%, preferably about 39%, of the cavities in the tail, the aft cavities are present at about 45 to about 65%, preferably about 54% of the cavities in the tail, and the remaining about 2 to about 20%, preferable about 7%, of larger cavities in the "sfw-GME" tail. The gme cavities associated with the aft and larger cavities are not included in these figures. The "sfw-GME" tail accounts for about 5-45% of the volume of the molecular sieve or the molecular sieve particle, preferably about 23%. JMZ-11C has a monotonically decreasing distribution of cavity sizes, but it cannot be described as a stochastic CHA-GME intergrowth.

JMZ-11D comprises two structure direct agents, an N,N-dimethyl-3,5-dimethylpiperidinium cation and a trimethyladmandylammonium cation, cha cavities, aft cavities and an "sfw-GME" tail, wherein the cha cavities are present at about 55 to about 75%, preferably about 65%, of the cavities in the tail, the aft cavities are present at about 7 to about 17%, preferably about 12% of the cavities in the tail, and the remaining about 8 to about 38%, preferable about 23%, of larger cavities in the "sfw-GME" tail. The gme cavities associated with the aft and larger cavities are not included in these figures. The "sfw-GME" tail accounts for about 50-90% of the volume of the molecular sieve or the molecular sieve particle, preferably about 75%. JMZ-11D has a monotonically decreasing distribution of cavity sizes, but it cannot be described as a stochastic CHA-GME intergrowth.

In a third aspect of the invention, a catalyst comprises an activated H-form of one or more molecular sieves of the second aspect of the invention, described herein, and can further comprise at least one extra-framework metal selected from the group consisting of Ag, Au, Ce, Co, Cr, Cu, Fe, Ga, In, Ir, Mn, Mo, Ni, Os, Pd, Pt, Re, Rh, Ru, Sn and Zn, preferably Cu, Fe, Co and Ni, more preferably Cu and Fe, most preferably Cu.

The activated H-form of the intergrowth in the catalyst can comprise about 0.1 to about 5 weight percent of at least one extra-framework metal.

In a fourth aspect of the invention, a catalyst article for treating exhaust gas comprises a catalyst comprising an activated H-form of a molecular sieve of the second aspect of the invention and can further comprise at least one extra-framework metal selected from the group consisting of Ag, Au, Ce, Co, Cr, Cu, Fe, Ga, In, Ir, Mn, Mo, Ni, Os, Pd, Pt, Re, Rh, Ru, Sn and Zn, preferably Co, Cu, Fe, and Ni, more preferably Cu and Fe, most preferably Cu.

The activated H-form of a molecular sieve in the catalyst can comprise about 0.1 to about 5 weight percent of at least one extra-framework metal.

The catalyst can be disposed on and/or within a porous substrate, preferably a flow through or wall-flow filter.

Catalysts of the present invention are particularly applicable for heterogeneous catalytic reaction systems (i.e., solid catalyst in contact with a gas reactant). To improve contact surface area, mechanical stability, and/or fluid flow characteristics, the catalysts can be disposed on and/or within a substrate, preferably a porous substrate. A washcoat containing the catalyst can be applied to an inert substrate, such as corrugated metal plate or a honeycomb cordierite brick. Alternatively, the catalyst is kneaded along with other components such as fillers, binders, and reinforcing agents, into an extrudable paste which then can be extruded through a die to form a honeycomb brick or extruded body such as a cylinder, trilobe or quadralobe. The catalyst may also be in the form of a micro-spherical particle (10-150 microns in diameter) containing an activated molecular sieve of the present invention together with fillers, binders and/or reinforcing agents. The micro-spherical particle can be prepared by spray drying or other suitable techniques. Accordingly, a catalyst article can comprise an activated molecular sieve described herein coated on and/or incorporated into a substrate.

The catalytic article can comprise a washcoat comprising an activated molecular sieve as described in the second aspect of the invention. The washcoat is preferably a solution, suspension, or slurry. Suitable coatings include surface coatings, coatings that penetrate a portion of the substrate, coatings that permeate the substrate, or some combination thereof.

A washcoat can also include non-catalytic components, such as fillers, binders, stabilizers, rheology modifiers, and other additives, including one or more of alumina, silica, non-zeolite silica alumina, titania, zirconia, ceria. Where the catalyst is part of a washcoat composition, the washcoat can further comprise a binder containing Ce or ceria. When the binder contains Ce or ceria, the Ce containing particles in the binder are significantly larger than the Ce containing particles in the catalyst. The catalyst composition can comprise pore-forming agents such as graphite, cellulose, starch, polyacrylate, and polyethylene, and the like. These additional components do not necessarily catalyze the desired reaction, but instead improve the catalytic material's effectiveness, for example, by increasing its operating temperature range, increasing contact surface area of the catalyst, increasing adherence of the catalyst to a substrate, etc. The washcoat loading on, or in, the substrate can be between about 0.3 $g/in^3$ to about 3.5 $g/in^3$, where the endpoints can be included. The loading can be a function of the type of substrate used and the backpressure that results from the loading on a specific type of substrate. The lower limit for the washcoat loading can be 0.5 $g/in^3$, 0.8 $g/in^3$, 1.0 $g/in^3$, 1.25 $g/in^3$, or 1.5 $g/in^3$. The upper limit for the washcoat loading can be 3.5 $g/in^3$, 3.25 $g/in^3$, 3.0 $g/in^3$, 2.75 $g/in^3$, 2.5 $g/in^3$, 2.25 $g/in^3$, 2.0 $g/in^3$, 1.75 $g/in^3$ or 1.5 $g/in^3$.

Two of the most common substrate designs to which catalyst can be applied are plate and honeycomb. Preferred substrates, particularly for mobile applications, include flow-through monoliths having a so-called honeycomb geometry that comprise multiple adjacent, parallel channels that are open on both ends and generally extend from the inlet face to the outlet face of the substrate and result in a high-surface area-to-volume ratio. For certain applications, the honeycomb flow-through monolith preferably has a high cell density, for example about 600 to 800 cells per square inch, and/or an average internal wall thickness of about 0.18-0.35 mm, preferably about 0.20-0.25 mm. For certain other applications, the honeycomb flow-through monolith preferably has a low cell density of about 150-600 cells per square inch, more preferably about 200-400 cells per square inch. Preferably, the honeycomb monoliths are porous. In addition to cordierite, silicon carbide, silicon nitride, ceramic, and metal, other materials that can be used for the substrate include aluminum nitride, silicon nitride, aluminum titanate, α-alumina, mullite, e.g., acicular mullite, pollucite, a thermet such as $Al_2OsZFe$, $Al_2O_3/Ni$ or $B_4CZFe$, or composites comprising segments of any two or more thereof. Preferred materials include cordierite, silicon carbide, and alumina titanate.

Plate-type catalysts have lower pressure drops and are less susceptible to plugging and fouling than the honeycomb types, which is advantageous in high efficiency stationary applications, but plate configurations can be much larger and more expensive. A honeycomb configuration is typically smaller than a plate type, which is an advantage in mobile applications, but has higher pressure drops and plug more easily. The plate substrate can be constructed of metal, preferably corrugated metal.

A catalyst article can be made by a process as herein described. The catalyst article can be produced by a process that includes the steps of applying preferably as a washcoat, of an activated molecular sieve, preferably an extra-framework metal containing activated molecular sieve, to a substrate as a layer either before or after at least one additional layer of another composition for treating exhaust gas has been applied to the substrate. The one or more catalyst layers on the substrate, including the layer comprising an activated molecular sieve, are arranged in consecutive layers. As used herein, the term "consecutive" with respect to catalyst layers on a substrate means that each layer is contact with its adjacent layer(s) and that the catalyst layers as a whole are arranged one on top of another on the substrate.

An activated molecular sieve catalyst can be disposed on the substrate as a first layer or zone and another composition, such as an oxidation catalyst, reduction catalyst, scavenging component, or $NO_x$ storage component, can be disposed on the substrate as a second layer or zone. As used herein, the terms "first layer" and "second layer" are used to describe the relative positions of catalyst layers in the catalyst article with respect to the normal direction of exhaust gas flow-through, past, and/or over the catalyst article. Under normal exhaust gas flow conditions, exhaust gas contacts the first layer prior to contacting the second layer. The second layer can be applied to an inert substrate as a bottom layer and the first layer is a top layer that is applied over the second layer as a consecutive series of sub-layers.

The exhaust gas can penetrate (and hence contact) the first layer, before contacting the second layer, and subsequently returns through the first layer to exit the catalyst component.

The first layer can be a first zone disposed on an upstream portion of the substrate and the second layer is disposed on the substrate as a second zone, wherein the second zone is downstream of the first.

The catalyst article can be produced by a process that includes the steps of applying an activated molecular sieve, preferably as a washcoat, to a substrate as a first zone, and subsequently applying at least one additional composition for treating an exhaust gas to the substrate as a second zone, wherein at least a portion of the first zone is downstream of the second zone. Alternatively, a composition comprising an activated molecular sieve can be applied to the substrate in a second zone that is downstream of a first zone containing the additional composition. Examples of additional compositions include oxidation catalysts, reduction catalysts, scavenging components (e.g., for sulfur, water, etc.), or $NO_x$ storage components.

To reduce the amount of space required for an exhaust system, individual exhaust components can be designed to perform more than one function. For example, applying an SCR catalyst to a wall-flow filter substrate instead of a flow-through substrate serves to reduce the overall size of an exhaust treatment system by allowing one substrate to serve two functions, namely catalytically reducing $NO_x$ concentration in the exhaust gas and mechanically removing soot from the exhaust gas. The substrate can be a honeycomb wall-flow filter or partial filter. Wall-flow filters are similar to flow-through honeycomb substrates in that they contain a plurality of adjacent, parallel channels. However, the channels of flow-through honeycomb substrates are open at both ends, whereas the channels of wall-flow substrates have one end capped, wherein the capping occurs on opposite ends of adjacent channels in an alternating pattern. Capping alternating ends of channels prevents the gas entering the inlet face of the substrate from flowing straight through the channel and existing. Instead, the exhaust gas enters the front of the substrate and travels into about half of the channels where it is forced through the channel walls prior to entering the second half of the channels and exiting the back face of the substrate.

The substrate wall has a porosity and pore size that is gas permeable, but traps a major portion of the particulate matter, such as soot, from the gas as the gas passes through the wall. Preferred wall-flow substrates are high efficiency filters. Wall flow filters for use with the present invention preferably have an efficiency of ≥70%, ≥about 75%, ≥about 80%, or ≥about 90%. The efficiency can be from about 75 to about 99%, about 75 to about 90%, about 80 to about 90%, or about 85 to about 95%. Here, efficiency is relative to soot and other similarly sized particles and to particulate concentrations typically found in conventional diesel exhaust gas. For example, particulates in diesel exhaust can range in size from 0.05 microns to 2.5 microns. Thus, the efficiency can be based on this range or a sub-range, such as 0.1 to 0.25 microns, 0.25 to 1.25 microns, or 1.25 to 2.5 microns.

Porosity is a measure of the percentage of void space in a porous substrate and is related to backpressure in an exhaust system: generally, the lower the porosity, the higher the backpressure. Preferably, the porous substrate has a porosity of about 30 to about 80%, for example about 40 to about 75%, about 40 to about 65%, or from about 50 to about 60%, where the endpoints can be included.

The pore interconnectivity, measured as a percentage of the substrate's total void volume, is the degree to which pores, void, and/or channels, are joined to form continuous paths through a porous substrate, i.e., from the inlet face to the outlet face. In contrast to pore interconnectivity is the sum of closed pore volume and the volume of pores that have a conduit to only one of the surfaces of the substrate. Preferably, the porous substrate has a pore interconnectivity volume of ≥about 30%, more preferably ≥about 40%.

The mean pore size of the porous substrate is also important for filtration. Mean pore size can be determined by any acceptable means, including by mercury porosimetry. The mean pore size of the porous substrate should be of a high enough value to promote low backpressure, while providing an adequate efficiency by either the substrate per se, by promotion of a soot cake layer on the surface of the substrate, or combination of both. Preferred porous substrates have a mean pore size of about 10 to about 40 µm, for example about 20 to about 30 µm, about 10 to about 25 µm, about 10 to about 20 m, about 20 to about 25 µm, about 10 to about 15 µm, and about 15 to about 20 µm.

In general, the production of an extruded solid body, such as honeycomb flow-through or wall-flow filter, containing an activated molecular sieve, described herein, as a catalyst involves blending ab activated molecular sieve, a binder, an optional organic viscosity-enhancing compound into an homogeneous paste which is then added to a binder/matrix component or a precursor thereof and optionally one or more of stabilized ceria, and inorganic fibers. The blend is compacted in a mixing or kneading apparatus or an extruder. The mixtures have organic additives such as binders, pore formers, plasticizers, surfactants, lubricants, dispersants as processing aids to enhance wetting and therefore produce a uniform batch. The resulting plastic material is then molded, in particular using an extrusion press or an extruder including an extrusion die, and the resulting moldings are dried and calcined. The organic additives are "burnt out" during calcinations of the extruded solid body. An activated molecular sieve, the catalytically active calcined product, can also be washcoated or otherwise applied to the extruded solid body as one or more sub-layers that reside on the surface or penetrate wholly or partly into the extruded solid body.

The binder/matrix component is preferably selected from the group consisting of cordierite, nitrides, carbides, borides, intermetallics, lithium aluminosilicate, a spinel, an optionally doped alumina, a silica source, titania, zirconia, titania-zirconia, zircon and mixtures of any two or more thereof. The paste can optionally contain reinforcing inorganic fibers selected from the group consisting of carbon fibers, glass fibers, metal fibers, boron fibers, alumina fibers, silica fibers, silica-alumina fibers, silicon carbide fibers, potassium titanate fibers, aluminum borate fibers and ceramic fibers.

The alumina binder/matrix component is preferably gamma alumina, but can be any other transition alumina, i.e., alpha alumina, beta alumina, chi alumina, eta alumina, rho alumina, kappa alumina, theta alumina, delta alumina, lanthanum beta alumina and mixtures of any two or more such transition aluminas. It is preferred that the alumina is doped with at least one non-aluminum element to increase the thermal stability of the alumina. Suitable alumina dopants include silicon, zirconium, barium, lanthanides and mixtures of any two or more thereof. Suitable lanthanide dopants include La, Ce, Nd, Pr, Gd and mixtures of any two or more thereof.

Preferably, an activated molecular sieve, is dispersed throughout, and preferably evenly throughout, the entire extruded catalyst body.

Where any of the above extruded solid bodies are made into a wall-flow filter, the porosity of the wall-flow filter can be from 30-80%, such as from 40-70%. Porosity and pore volume and pore radius can be measured e.g. using mercury intrusion porosimetry.

In a fifth aspect of the invention, an exhaust system for treating exhaust gases from an engine can comprise: (a) a catalyst article comprising an activated H-form of a molecular sieve of the second aspect of the invention and at least one extra-framework metal selected from the group consisting of Ag, Au, Ce, Co, Cr, Cu, Fe, Ga, In, Ir, Mn, Mo, Ni, Os, Pd, Pt, Re, Rh, Ru, Sn and Zn, preferably Cu, Fe, Co and Ni, more preferably Cu and Fe, most preferably Cu, disposed downstream from the engine; (b) a source of a reductant, such as ammonia or urea upstream of said catalyst article; and (c) an exhaust gas conduit for carrying the exhaust gases from the engine to said catalyst article.

In some embodiments, the activated H-form of molecular sieve of the second aspect of the invention can be an SCR or an ammonia oxidation component.

The system can include a controller for metering of nitrogenous reductant into the flowing exhaust gas only when it is determined that the catalyst is capable of catalyzing $NO_x$ reduction at or above a desired efficiency, such as at temperatures above 100° C., above 150° C. or above 175° C. This determination can be assisted by one or more suitable sensor inputs indicative of a condition of the engine selected from the group consisting of: exhaust gas temperature, catalyst bed temperature, accelerator position, mass flow of exhaust gas in the system, manifold vacuum, ignition timing, engine speed, lambda value of the exhaust gas, the quantity of fuel injected in the engine, the position of the exhaust gas recirculation (EGR) valve and thereby the amount of EGR and boost pressure.

In a particular embodiment, metering can be controlled in response to the quantity of nitrogen oxides in the exhaust gas determined either directly (using a suitable $NO_x$ sensor) or indirectly, such as using pre-correlated look-up tables or maps—stored in the control means—correlating any one or more of the abovementioned inputs indicative of a condition of the engine with predicted $NO_x$ content of the exhaust gas. The metering of the nitrogenous reductant can be arranged such that 60% to 200% of theoretical ammonia is present in exhaust gas entering the SCR catalyst calculated at 1:1 $NH_3/NO$ and 4:3 $NH_3/NO_2$. The control means can comprise a pre-programmed processor such as an electronic control unit (ECU).

An exhaust system for internal combustion engines can comprise a passive $NO_x$ adsorber. The exhaust system preferably comprises one or more additional after-treatment devices capable of removing pollutants from internal combustion engine exhaust gases at normal operating temperatures. Preferably, the exhaust system comprises the passive $NO_x$ adsorber and one or more other catalyst components selected from: (1) a selective catalytic reduction (SCR) catalyst, (2) a particulate filter, (3) a SCR filter, (4) a $NO_x$ adsorber catalyst, (5) a three-way catalyst, (6) an oxidation catalyst, or any combination thereof. The passive $NO_x$ adsorber is preferably a separate component from any of the above after-treatment devices. Alternatively, the passive $NO_x$ adsorber can be incorporated as a component into any of the above after-treatment devices.

These after-treatment devices are well known in the art. Selective catalytic reduction (SCR) catalysts are catalysts that reduce $NO_x$ to $N_2$ by reaction with nitrogen compounds (such as ammonia or urea) or hydrocarbons (lean $NO_x$ reduction). A typical SCR catalyst is comprised of a vanadia-titania catalyst, a vanadia-tungsta-titania catalyst, or a metal/zeolite catalyst such as iron/beta zeolite, copper/beta zeolite, copper/SSZ-13, copper/SAPO-34, Fe/ZSM-5, or copper/ZSM-5.

Particulate filters are devices that reduce particulates from the exhaust of internal combustion engines. Particulate filters include catalyzed particulate filters and bare (non-catalyzed) particulate filters. Catalyzed particulate filters (for diesel and gasoline applications) include metal and metal oxide components (such as Pt, Pd, Fe, Mn, Cu, and Ce) to oxidize hydrocarbons and carbon monoxide in addition to destroying soot trapped by the filter.

Selective catalytic reduction filters (SCRF) are single-substrate devices that combine the functionality of an SCR and a particulate filter. They are used to reduce $NO_x$ and particulate emissions from internal combustion engines. In addition to the SCR catalyst coating, the particulate filter can also include other metal and metal oxide components (such as Pt, Pd, Fe, Mn, Cu, and ceria) to oxidize hydrocarbons and carbon monoxide in addition to destroying soot trapped by the filter. $NO_x$ adsorber catalysts (NACs) are designed to adsorb $NO_x$ under lean exhaust conditions, release the adsorbed $NO_x$ under rich conditions, and reduce the released $NO_x$ to form $N_2$. NACs typically include a $NO_x$-storage component (e.g., Ba, Ca, Sr, Mg, K, Na, Li, Cs, La, Y, Pr, and Nd), an oxidation component (preferably Pt) and a reduction component (preferably Rh). These components are contained on one or more supports.

Three-way catalysts (TWCs) are typically used in gasoline engines under stoichiometric conditions in order to convert $NO_x$ to $N_2$, carbon monoxide to $CO_2$, and hydrocarbons to $CO_2$ and $H_2O$ on a single device.

Oxidation catalysts, and in particular diesel oxidation catalysts (DOCS), are well-known in the art. Oxidation catalysts are designed to oxidize CO to $CO_2$ and gas phase hydrocarbons (HC) and an organic fraction of diesel particulates (soluble organic fraction) to $CO_2$ and $H_2O$. Typical oxidation catalysts include platinum and optionally also palladium on a high surface area inorganic oxide support, such as alumina, silica-alumina and a zeolite.

The exhaust system can be configured so that the passive $NO_x$ adsorber is located close to the engine and the additional after-treatment device(s) are located downstream of the passive $NO_x$ adsorber. Thus, under normal operating conditions, engine exhaust gas first flows through the passive $NO_x$ adsorber prior to contacting the after-treatment device(s). Alternatively, the exhaust system can contain valves or other gas-directing means such that during the low temperature period (below a temperature ranging from about 150 to 220° C., preferably 200° C., about as measured at the after-treatment device(s)), the exhaust gas is directed to contact the after-treatment device(s) before flowing to the passive $NO_x$ adsorber. Once the after-treatment device(s) reaches the operating temperature (about 150 to 220° C., preferably 200° C., as measured at the after-treatment device(s)), the exhaust gas flow is then redirected to contact the passive $NO_x$ adsorber prior to contacting the after-treatment device(s). This ensures that the temperature of the passive $NO_x$ adsorber remains low for a longer period of time, and thus improves efficiency of the passive $NO_x$ adsorber, while simultaneously allowing the after-treatment device(s) to more quickly reach operating temperature. U.S. Pat. No. 5,656,244, the teachings of which are incorporated herein by reference, for example, teaches means for controlling the flow of the exhaust gas during cold-start and normal operating conditions.

In a sixth aspect of the invention, a method for synthesizing an SDA containing molecular sieve of the first aspect of the invention comprises:
a. forming a reaction mixture comprising: (i) at least one source of aluminum, (ii) at least one source of silicon, (iii) at least one source of alkaline or alkaline-earth cations and (iv) one or more structure directing agents;
b. heating the reaction mixture;
c. forming molecular sieve crystals having an intergrowth and the structure directing agent as described herein, and
d. recovering at least a portion of the molecular sieve crystals from the reaction mixture.

Many aluminum compounds and their mixtures are suitable for use as the at least one source of alumina in the present invention. The aluminum compounds include, but are not necessarily limited to aluminum oxide, boehmite, pseudo boehmite, aluminum hydroxy chloride, aluminum alkoxides such as aluminum tri-isopropoxide, aluminum tri-ethoxide, aluminum tri-n-butoxide and aluminum tri-isobutoxide, and mixtures thereof. A preferred aluminum component is selected from the group consisting of aluminum hydroxide, boehmite and pseudo boehmite.

The at least one source of alumina can comprise aluminum alkoxides, aluminum phosphates, aluminum hydroxide, sodium aluminate, pseudoboehmite, hydrated alumina, organoalumina, colloidal alumina, zeolite Y and mixtures thereof.

A number of silicon compounds and their mixtures may be used as the silicon component for the method of the present invention. The silicon compounds include, but are not limited to silica sol silica gel, colloidal silica, fumed silica, silicic acid, tetraethyl silicate, tetramethyl silicate, an alkoxide, a silicate, a tetraalkyl orthosilicate, an aqueous colloidal suspension of silica and mixtures thereof. A preferred silicon component comprises a material selected from the group consisting of silica sol, silica gel, colloidal silica, fumed silica, silicic acid, and mixtures thereof.

The source of alkaline or alkaline-earth cations may be any source of these elements, preferably selected from a source of Na, K and combinations thereof.

SDA-1 is an N,N-dimethyl-3,5-dimethylpiperidinium cation or an N,N-diethyl-2,6-dimethylpiperidinium cation. SDA-2 is a CHA generating SDA, such as a trimethyladmandylammonium cation. SDA-3 is a AFX generating SDA, such as 1,3-bis(1-adamantyl)imidazolium cation. SDA-2 and or SDA-3 can be added to control the proportion of cha and aft and consequently the "sfw-GME tail".

The cation of the structure directing agent can be associated with an anion selected from the group consisting of acetate, bicarbonate, bromide, carbonate, carboxylate, chloride, fluoride, hydroxide, iodide, sulfate and tetrafluoroborate or combinations thereof. Preferably the anion is hydroxide.

The reaction mixture can have a molar compositional ratio of:

| Components | Ratio | Preferred Ratio |
| --- | --- | --- |
| $MeO_2/A_2O_3$ | 10-100 | 20-50 |
| (SDA-1 + SDA-2 + SDA-3)/$A_2O_3$ | 1-6 | 1.0-3.0 |
| SDA-2/SDA-1 | 0-100 | 0.00-15.0 |
| SDA-3/SDA-1 | 0-100 | 0.00-15.0 |
| $X_2O/A_2O_3$ | 5.0-20.0 | 7.5-15 |
| $[OH^-]/A_2O_3$ | 10.0-30.0 | 16.0-30 |
| $H_2O/A_2O_3$ | 100-2000 | 200-800 | where Me is Si, Ge, Sn, Ti or combinations thereof and is calculated as being in the oxide form ($MO_2$); A is Al, Fe, Cr, B, Ga or combinations thereof and is calculated as being in the oxide form ($A_2O_3$); X is Na, K or a combination thereof and is calculated as being in the oxide form ($X_2O$); [OH$^-$] is calculated being as the sum of hydroxide ions brought by all components; SDA-1 is an N,N-dimethyl-3,5-dimethylpiperidinium cation or an N,N-diethyl-2,6-dimethylpiperidinium cation, SDA-2 is a CHA generating SDA, such as a trimethyladmandylammonium cation, a tetraethylammonium cation, a trimethylbenzylammonium cation, a trimethylcyclohexylammonium cation or a trimethyl(cyclohexylmethyl)ammonium or a phenyltrimethylammonium cation and SDA-3 is a AFX generating SDA, such as a 1,3-bis(1-adamantyl)imidazolium, 1,1-(butane-1,4-diyl)bis-(quinuclidin-1-ium), 1,1-(pentane-1,5-diyl)bis-(quinuclidin-1-ium), 1,1'-(1,4-butanediyl)bis(4-aza-1-azoniabicyclo[2.2.2]octane), 1,1'-(1,5-pentanediyl)bis(4-aza-1-azoniabicyclo[2.2.2]octane).

The reaction mixture can further comprise from about 0.1 to about 10% w/w of seed crystals, wherein the seed crystals comprise a crystalline molecular sieve having an AEI, AFX, AFT, CHA, GME or an SFW framework and/or an intergrowth having a JMZ-11, JMZ-11B or JMZ-11C framework.

A solvent can be mixed with the structure directing agent before the structure directing agent is added to the reaction mixture. Preferably, the structure directing agent is completely mixable with, or soluble in, the solvent. Suitable solvents include but are not necessarily limited to water, methanol, ethanol, n-propanol, iso-propanol, $C_4$ alcohols, ethylene glycol, 1,2-propylene glycol, 1,3-propylene glycol and mixtures thereof. A preferred solvent comprises water.

The silica component can be mixed in a suitable solvent to form a first mixture of uniform composition and texture. Adequate mixing, stirring, or agitation usually can be used. The aluminum component can be added to this mixture, followed by the structure directing agent.

In order to make an SDA containing intergrowth, the molar ratios of the components in the mixture must be controlled and maintained. Before being subjected to conditions effective to produce the molecular sieve product, the final reaction mixture, excluding any other organic or inorganic moieties or species which may be present, has a molar compositional ratio of:

| Components | Ratio | Preferred Ratio |
|---|---|---|
| MeO$_2$/A$_2$O$_3$ | 10-100 | 20-50 |
| (SDA-1 + SDA-2 + SDA-3)/A$_2$O$_3$ | 1-6 | 1.0-3.0 |
| SDA-2/SDA-1 | 0-100 | 0.00-15.0 |
| SDA-3/SDA-1 | 0-100 | 0.00-15.0 |
| X$_2$O/A$_2$O$_3$ | 5.0-20.0 | 7.5-15 |
| [OH$^-$]/A$_2$O$_3$ | 10.0-30.0 | 16.0-30 |
| H$_2$O/A$_2$O$_3$ | 100-2000 | 200-800 | where Me is Si, Ge, Sn, Ti or combinations thereof and is calculated as being in the oxide form (MO$_2$); A is Al, Fe, Cr, B, Ga or combinations thereof and is calculated as being in the oxide form (A$_2$O$_3$); X is Na, K or a combination thereof and is calculated as being in the oxide form (X$_2$O); [OH$^-$] is calculated being as the sum of hydroxide ions brought by all components; SDA-1 is an N,N-dimethyl-3,5-dimethylpiperidinium cation or an N,N-diethyl-2,6-dimethylpiperidinium cation, SDA-2 is a CHA generating SDA, such as a trimethyladmandylammonium cation, a tetraethylammonium cation, a trimethylbenzylammonium cation, a trimethylcyclohexylammonium cation or a trimethyl(cyclohexylmethyl)ammonium or a phenyltrimethylammonium cation and SDA-3 is a AFX generating SDA, such as a 1,3-bis(1-adamantyl)imidazolium, 1,1-(butane-1,4-diyl)bis-(quinuclidin-1-ium), 1,1-(pentane-1,5-diyl)bis-(quinuclidin-1-ium), 1,1'-(1,4-butanediyl)bis(4-aza-1-azoniabicyclo[2.2.2]octane), 1,1'-(1,5-pentanediyl)bis(4-aza-1-azoniabicyclo[2.2.2]octane).

It is preferable to use adequate mixing, blending, stirring, or agitation to provide a uniform composition throughout the mixture. The use of a concentration or composition gradient should be minimized because such a gradient could result in the formation of different molecular sieve products.

Preferably, a constant temperature can be maintained during the preparation of the mixture. Cooling or heating may be required to provide a constant temperature environment. A suitable temperature for preparation of a mixture can be in the range of from about 15° C. to about 80° C., preferably from about 20° C. to about 50° C. Pressure is usually not critical for preparing a mixture unless one or more gases are used to control other reaction parameters, such as pH, temperature, or concentration.

Preferably, the overall process will have an overall yield on silica of at least about 60%, for Example at least about 70%, at least about 80%.

The reaction mixture can be in the form of a solution, a colloidal dispersion (colloidal sol), gel, or paste, with a gel being preferred.

Generally, the reaction mixture can be maintained at an elevated temperature until the SDA containing intergrowth crystals are formed. The hydrothermal crystallization is usually conducted under autogenous pressure, at a temperature between about 100-220° C., for example between about 150 and 200° C., for duration of several hours, for example, about 0.1-10 days, and preferably from about 1-7 days.

During the hydrothermal crystallization step, crystals of the intergrowth can be allowed to nucleate spontaneously from the reaction mixture. The use of intergrowth crystals as seed material can be advantageous in decreasing the time necessary for complete crystallization to occur. When used as seeds, intergrowth crystals can be added in an amount between 0.1 and 10% of the weight of silica used in the reaction mixture.

Once the SDA containing intergrowth crystals have formed, the solid product can be separated from the reaction mixture by standard separation techniques such as filtration. The SDA containing intergrowth crystals can be water-washed and then dried, for several second to a few minutes (e.g., 5 second to 10 minutes for flash drying) or several hours (e.g., about 4-24 hours for oven drying at 75-150° C.), to obtain SDA containing intergrowth crystals. The drying step can be performed at atmospheric pressure or under vacuum.

It will be appreciated that the foregoing sequence of steps, as well as each of the above-mentioned periods of time and temperature values are merely exemplary and may be varied.

The intergrowth crystals produced in accordance with the methods described herein can have a mean crystalline size of about 0.01 to about 20 μm, for example about 0.01 to about 5 μm, about 0.2 to about 1 μm, and about 0.25 to about 0.5 μm, where the endpoints can be included. Large crystals can be milled using a jet mill or other particle-on-particle milling technique to an average size of about 1.0 to about 1.5 micron to facilitate washcoating a slurry containing the catalyst to a substrate, such as a flow-through monolith.

The reaction mixture for intergrowth synthesis process typically contains at least one source of aluminum, at least one structure directing agent (SDA-1), where in (SDA-1) comprises an N,N-dimethyl-3,5-dimethylpiperidinium cation or an N,N-diethyl-2,6-dimethylpiperidinium cation, at least one source of silicon, and at least one source of an alkaline metal or an alkaline earth metal. The composition can further comprise a second SDA (SDA-2) and or a third SDA (SDA-3). SDA-2 is a CHA generating SDA, such as a trimethyladmandylammonium cation, a tetraethylammonium cation, a trimethylbenzylammonium cation, a trimethylcyclohexylammonium cation or a trimethyl(cyclohexylmethyl)ammonium or a phenyltrimethylammonium cation. SDA-3 is a AFX generating SDA, such as a 1,3-bis(1-adamantyl)imidazolium, 1,1-(butane-1,4-diyl)bis-(quinuclidin-1-ium), 1,1-(pentane-1,5-diyl)bis-(quinuclidin-1-ium), 1,1'-(1,4-butanediyl)bis(4-aza-1-azoniabicyclo[2.2.2]octane), 1,1'-(1,5-pentanediyl)bis(4-aza-1-azoniabicyclo[2.2.2]octane).

The synthesis methods described herein are not necessarily limited to forming metaloaluminosilicates, but can also be applied to synthesize other compositions of JMZ-11 such as molecular sieves comprising phosphorus in the framework, such as aluminophosphates (AlPO), a metal-substituted aluminophosphates (MeAlPO), a silico-aluminophosphates (SAPO), or a metal substituted silico-aluminophosphates.

In a seventh aspect of the invention, methods of synthesizing an activated molecular sieve from an activated molecular sieve which comprises an SDA, are described. An activated molecular sieve is lacking the structure directing agent that is present in an activated molecular sieve of the first aspect of the invention. An activated molecular sieve can have the SDA removed by calcination or treatment with a peroxide.

An activated molecular sieve can be produced by calcining an intergrowth comprising two or more SDAs at a temperature and for a period of time sufficient to remove the structure directing agent and form an activated molecular sieve. An activated molecular sieve can be calcined at 300-700° C., preferably at 400 to 650° C. in the presence of an oxygen-containing gas (such as air) when it is desirable to oxidize the SDAs. In some case, where a reducing environment is preferred, calcination is performed using an inert gas. The inert gas can be any gas that is substantially free of oxygen (less than 1 vol. % oxygen, preferably less than 0.1 vol. % oxygen), most preferably oxygen-free.

Preferably, the inert gas is nitrogen, argon, neon, helium, carbon dioxide, or the like, and mixture thereof. The calcination is preferably performed for greater than 1 hour.

The production of an activated molecular sieve of the second aspect of the convention can comprise first forming SDA containing intergrowth of the first aspect of the invention and then converting the SDA containing intergrowth to an activated molecular sieve.

In an eighth aspect of the invention, a composition for manufacturing an SDA containing intergrowth comprises the following materials in the corresponding ratios:

| Components | Ratio | Preferred Ratio |
|---|---|---|
| $MeO_2/A_2O_3$ | 10-100 | 20-50 |
| (SDA-1 + SDA-2 + SDA-3)/$A_2O_3$ | 1-6 | 1.0-3.0 |
| SDA-2/SDA-1 | 0-100 | 0.00-15.0 |
| SDA-3/SDA-1 | 0-100 | 0.00-15.0 |
| $X_2O/A_2O_3$ | 5.0-20.0 | 7.5-15 |
| $[OH^-]/A_2O_3$ | 10.0-30.0 | 16.0-30 |
| $H_2O/A_2O_3$ | 100-2000 | 200-800 | where Me is Si, Ge, Sn, Ti or combinations thereof and is calculated as being in the oxide form ($MO_2$); A is Al, Fe, Cr, B, Ga or combinations thereof and is calculated as being in the oxide form ($A_2O_3$); X is Na, K or a combination thereof and is calculated as being in the oxide form ($X_2O$); [$OH^-$] is calculated being as the sum of hydroxide ions brought by all components; SDA-1 is an N,N-dimethyl-3,5-dimethylpiperidinium cation or an N,N-diethyl-2,6-dimethylpiperidinium cation, SDA-2 is a CHA generating SDA, such as a trimethyladmandylammonium cation, a tetraethylammonium cation, a trimethylbenzylammonium cation, a trimethylcyclohexylammonium cation or a trimethyl(cyclohexylmethyl)ammonium or a phenyltrimethylammonium cation and SDA-3 is a AFX generating SDA, such as a 1,3-bis(1-adamantyl)imidazolium, 1,1-(butane-1,4-diyl)bis-(quinuclidin-1-ium), 1,1-(pentane-1,5-diyl)bis-(quinuclidin-1-ium), 1,1'-(1,4-butanediyl)bis(4-aza-1-azoniabicyclo[2.2.2]octane), 1,1'-(1,5-pentanediyl)bis(4-aza-1-azoniabicyclo[2.2.2]octane).

A number of silicon compounds and their mixtures can be used as the silicon component for the composition of the present invention. The silicon compounds include, but are not limited to silica sol silica gel, colloidal silica, fumed silica, silicic acid, tetraethyl silicate, tetramethyl silicate, and mixtures thereof. A preferred silicon component comprises a material selected from the group consisting of silica sol, silica gel, colloidal silica, fumed silica, silicic acid, and mixtures thereof.

Many aluminum compounds and their mixtures are suitable for use as the aluminum component in the present invention. The aluminum compounds include, but are not necessarily limited to aluminum oxide, boehmite, pseudo boehmite, aluminum hydroxy chloride, aluminum alkoxides such as aluminum tri-isopropoxide, aluminum tri-ethoxide, aluminum tri-n-butoxide and aluminum tri-isobutoxide, and mixtures thereof. A preferred aluminum component is selected from the group consisting of aluminum hydroxide, boehmite and pseudo boehmite.

The composition comprises a first SDA (SDA-1) and can further comprise a second SDA (SDA-2) and or a third SDA (SDA-3). SDA-1 is a N,N-dimethyl-3,5-dimethylpiperidinium cation or an N,N-diethyl-2,6-dimethylpiperidinium cation. SDA-2 is a CHA generating SDA, such as a trimethyladmandylammonium cation, a tetraethylammonium cation, a trimethylbenzylammonium cation, a trimethylcyclohexylammonium cation or a trimethyl(cyclohexylmethyl)ammonium or a phenyltrimethylammonium cation and SDA-3 is a AFX generating SDA, such as a 1,3-bis(1-adamantyl)imidazolium, 1,1-(butane-1,4-diyl)bis-(quinuclidin-1-ium), 1,1-(pentane-1,5-diyl)bis-(quinuclidin-1-ium), 1,1'-(1,4-butanediyl)bis(4-aza-1-azoniabicyclo[2.2.2]octane), 1,1'-(1,5-pentanediyl)bis(4-aza-1-azoniabicyclo[2.2.2]octane).

The anion associated with the cation can be an acetate, bicarbonate, bromide, carbonate, carboxylate, chloride, fluoride, hydroxide, iodide, sulfate and tetrafluoroborate, or a combination thereof. Preferably the anion is hydroxide.

The composition can further comprise from about 0.1 to about 10% w/w of seed crystals, wherein the seed crystals comprise a crystalline molecular sieve having an AEI, AFX, AFT, CHA, GME or an SFW framework and/or an intergrowth having a JMZ-11, JMZ-11B or JMZ-11C framework.

In a ninth aspect of the invention, provided are methods of making an activated molecular sieve from a molecular sieve comprising an intergrowth containing an SDA and alkali metal cations of the first aspect of the invention. Usually it is desirable to remove the alkali metal cation by ion exchange and replace it with hydrogen, ammonium, or any desired metal ion. Accordingly, zeolites of the present invention may be a Na-form zeolite, a K-form zeolite, or a combined Na, K-form and the like, or may be an H-form zeolite, an ammonium-form zeolite, or a metal-exchanged zeolite. Typical ion exchange techniques involve contacting the synthetic zeolite with a solution containing a salt of the desired replacing cation or cations. Although a wide variety of salts can be employed, chlorides and other halides, nitrates, sulfates and carbonates are particularly preferred. Representative ion exchange techniques are widely known in the art. Ion exchange occurs post-synthesis and can take place either before or after the zeolite is calcined. Following contact with the salt solution of the desired replacing cation, the zeolite is typically washed with water and dried at temperatures ranging from 65° C. to about 315° C., usually between 80° C. and 150° C. After washing, the zeolite can be calcined in an inert gas and/or air at temperature ranging from about 315° C. to 850° C. for periods of time ranging from 1 to 48 hours, or more, to produce a catalytically active and stable product.

In a tenth aspect of the invention, provided are methods for treating an exhaust gas from an engine by contacting the exhaust gas with an activated molecular sieve of the second aspect of the invention as herein before described. The methods can be used for the reduction of $NO_x$ compounds and/or oxidation of $NH_3$ in a gas, which comprises contacting the gas with an activated molecular sieve or a metal containing activated molecular sieve for a time sufficient to reduce the level of $NO_x$ compounds in the gas.

A method for treating an exhaust gas comprises contacting a combustion exhaust gas containing $NO_x$ and/or $NH_3$ with an activated H-form of a molecular sieve as described herein to selectively reduce at least a portion of the $NO_x$ into $N_2$ and $H_2O$ and/or oxidize at least a portion of the $NH_3$.

A method for treating an exhaust gas comprising contacting a combustion exhaust gas containing $NO_x$ with a passive $NO_x$ absorber comprising an activated H-form of a molecular sieve as described herein.

A method for treating an exhaust gas comprising contacting a combustion exhaust gas containing $NH_3$ with a passive $NO_x$ absorber comprising an activated H-form of a molecular sieve as described herein.

An activated molecular sieve or a metal containing activated molecular sieve can promote the reaction of a reductant, preferably ammonia, with nitrogen oxides to selectively form elemental nitrogen ($N_2$) and water ($H_2O$). Thus, the catalyst can be formulated to favor the reduction of nitrogen oxides with a reductant (i.e., an SCR catalyst). Examples of such reductants include hydrocarbons (e.g., C3-C6 hydrocarbons) and nitrogenous reductants such as ammonia and ammonia hydrazine or any suitable ammonia precursor, such as urea (($NH_2)_2CO$), ammonium carbonate, ammonium carbamate, ammonium hydrogen carbonate or ammonium formate.

An activated molecular sieve, or a metal containing activated molecular sieve, can also promote the oxidation of ammonia. Preferably, an activated molecular sieve contains one or more metal ions, such as copper or iron, that are impregnated into an activated molecular sieve. The catalyst can be formulated to favor the oxidation of ammonia with oxygen, particularly a concentration of ammonia typically encountered downstream of an SCR catalyst (e.g., ammonia oxidation (AMOX) catalyst, such as an ammonia slip catalyst (ASC)). An activated molecular sieve, or a metal containing an activated molecular sieve, can be disposed as a top layer over an oxidative under-layer, wherein the under-layer comprises a platinum group metal (PGM) catalyst or a non-PGM catalyst. Preferably, the catalyst component in the underlayer is disposed on a high surface area support, including but not limited to alumina.

SCR and AMOX operations can be performed in series, wherein both processes utilize a catalyst comprising an activated molecular sieve, or a metal containing activated molecular sieve, as described herein, and wherein the SCR process occurs upstream of the AMOX process. For example, an SCR formulation of the catalyst can be disposed on the inlet side of a filter and an AMOX formulation of the catalyst can be disposed on the outlet side of the filter.

Accordingly, provided is a method for the reduction of $NO_x$ compounds or oxidation of $NH_3$ in a gas, which comprises contacting the gas with a catalyst composition described herein for the catalytic reduction of $NO_x$ compounds for a time sufficient to reduce the level of $NO_x$ compounds and/or $NH_3$ in the gas. A catalyst article can have an ammonia slip catalyst disposed downstream of a selective catalytic reduction (SCR) catalyst. The ammonia slip catalyst can oxidize at least a portion of any nitrogenous reductant that is not consumed by the selective catalytic reduction process. The ammonia slip catalyst can be disposed on the outlet side of a wall flow filter and an SCR catalyst can be disposed on the upstream side of a filter. The ammonia slip catalyst can be disposed on the downstream end of a flow-through substrate and an SCR catalyst can be disposed on the upstream end of the flow-through substrate. The ammonia slip catalyst and SCR catalyst can be disposed on separate bricks within the exhaust system. These separate bricks can be adjacent to, and in contact with, each other or separated by a specific distance, provided that they are in fluid communication with each other and provided that the SCR catalyst brick is disposed upstream of the ammonia slip catalyst brick.

The SCR and/or AMOX process can be performed at a temperature of ≥100° C., preferably at a temperature from about 150° C. to about 750° C., more preferably from about 175 to about 550° C., even more preferably from 175 to 400° C.

In some conditions, the temperature range can be from 450 to 900° C., preferably 500 to 750° C., more preferably 500 to 650° C., even more preferably 450 to 550° C. Temperatures greater than 450° C. are particularly useful for treating exhaust gases from a heavy and light duty diesel engine that is equipped with an exhaust system comprising (optionally catalyzed) diesel particulate filters which are regenerated actively, e.g. by injecting hydrocarbon into the exhaust system upstream of the filter, wherein the molecular sieve catalyst for use in the present invention is located downstream of the filter.

Methods of the present invention can comprise contacting the exhaust gas with one or more flow-through SCR catalyst device(s) in the presence of a reducing agent to reduce the $NO_x$ concentration in the exhaust gas and one or more of the following steps: (a) accumulating and/or combusting soot that is in contact with the inlet of a catalytic filter; (b) introducing a nitrogenous reducing agent into the exhaust gas stream prior to contacting the catalytic filter, preferably with no intervening catalytic steps involving the treatment of $NO_x$ and the reductant; (c) generating $NH_3$ over a $NO_x$ adsorber catalyst or lean $NO_x$ trap, and preferably using such $NH_3$ as a reductant in a downstream SCR reaction; (d) contacting the exhaust gas stream with a DOC to oxidize hydrocarbon based soluble organic fraction (SOF) and/or carbon monoxide into $CO_2$, and/or oxidize NO into $NO_2$, which in turn, can be used to oxidize particulate matter in particulate filter; and/or reduce the particulate matter (PM) in the exhaust gas; and (e) contacting the exhaust gas with an ammonia slip catalyst, preferably downstream of the SCR catalyst to oxidize most, if not all, of the ammonia prior to emitting the exhaust gas into the atmosphere or passing the exhaust gas through a recirculation loop prior to exhaust gas entering/re-entering the engine.

All, or at least a portion of, the nitrogen-based reductant, particularly $NH_3$, for consumption in the SCR process can be supplied by a $NO_x$ adsorber catalyst (NAC), a lean $NO_x$ trap (LNT), or a $NO_x$ storage/reduction catalyst (NSRC), disposed upstream of the SCR catalyst, e.g., a SCR catalyst of the present invention disposed on a wall-flow filter. NAC components useful in the present invention include a catalyst combination of a basic material (such as alkali metal, alkaline earth metal or a rare earth metal, including oxides of alkali metals, oxides of alkaline earth metals, and combinations thereof), and a precious metal (such as platinum), and optionally a reduction catalyst component, such as rhodium. Specific types of basic material useful in the NAC include cesium oxide, potassium oxide, magnesium oxide, sodium oxide, calcium oxide, strontium oxide, barium oxide, and combinations thereof. The precious metal is preferably present at about 10 to about 200 g/ft$^3$, such as 20 to 60 g/ft$^3$. Alternatively, the precious metal of the catalyst is characterized by the average concentration which can be from about 40 to about 100 grams/ft$^3$.

During periodically rich regeneration events, $NH_3$ can be generated over a $NO_x$ adsorber catalyst. The SCR catalyst downstream of the $NO_x$ adsorber catalyst can improve the overall system $NO_x$ reduction efficiency. In the combined system, the SCR catalyst is capable of storing the released $NH_3$ from the NAC catalyst during rich regeneration events and utilizes the stored $NH_3$ to selectively reduce some or all of the $NO_x$ that slips through the NAC catalyst during the normal lean operation conditions.

The method for treating exhaust gas as described herein can be performed on an exhaust gas derived from a combustion process, such as from an internal combustion engine (whether mobile or stationary), a gas turbine and coal or oil fired power plants. The method can also be used to treat gas from industrial processes such as refining, from refinery heaters and boilers, furnaces, the chemical processing industry, coke ovens, municipal waste plants and incinerators, etc. The method can be used for treating exhaust gas from a vehicular lean burn internal combustion engine, such as a diesel engine, a lean-burn gasoline engine or an engine powered by liquid petroleum gas or natural gas.

A method for treating an exhaust gas can comprise contacting a combustion exhaust gas containing $NO_x$ with a passive $NO_x$ absorber comprising an activated molecular sieve of the second aspect of the invention, as herein before described. A passive $NO_x$ adsorber effective to adsorb $NO_x$ at or below a low temperature and release the adsorbed $NO_x$ at temperatures above the low temperature can comprise a noble metal and an activated molecular sieve. The noble metal can be selected from the group consisting of platinum, palladium, rhodium, gold, silver, iridium, ruthenium, osmium, and mixtures thereof, and is preferably palladium.

The passive $NO_x$ adsorber can be effective to adsorb $NO_x$ at, or below, a low temperature (preferably less than 250° C., more preferably about 200° C.) and release the adsorbed $NO_x$ at temperatures above the low temperature. The passive $NO_x$ adsorber comprises a noble metal and an activated molecular sieve. The noble metal is selected from the group consisting of palladium, platinum, rhodium, gold, silver, iridium, ruthenium, osmium, or mixtures thereof; more preferably, palladium, platinum, rhodium, or mixtures thereof. Palladium is particularly preferred.

The passive $NO_x$ adsorber can be prepared by any known means. For instance, the noble metal can be added to an activated molecular sieve to form the passive $NO_x$ adsorber by any known means, the manner of addition is not considered to be particularly critical. For Example, a noble metal compound (such as palladium nitrate) can be supported on an activated molecular sieve by impregnation, adsorption, ion-exchange, incipient wetness, precipitation, or the like. Other metals can also be added to the passive $NO_x$ adsorber. Preferably, some of the noble metal (more than 1 percent of the total noble metal added) in the passive $NO_x$ adsorber is located inside the pores of an activated molecular sieve. More preferably, more than 5 percent of the total amount of noble metal is located inside the pores of an activated molecular sieve; and even more preferably can be greater than 10 percent or greater than 25% or greater than 50 percent of the total amount of noble metal that is located inside the pores of an activated molecular sieve.

Preferably, the passive $NO_x$ adsorber further comprises a flow-through substrate or filter substrate. The passive $NO_x$ adsorber can be coated onto the flow-through or filter substrate, and preferably deposited on the flow-through or filter substrate using a washcoat procedure to produce a passive $NO_x$ adsorber system.

The flow-through or filter substrate can be a substrate that is capable of containing catalyst components. The substrate is preferably a ceramic substrate or a metallic substrate. The ceramic substrate can be made of any suitable refractory material, e.g., alumina, silica, titania, ceria, zirconia, magnesia, molecular sieves, preferably a zeolite, more preferable an aluminosilicate, silicon nitride, silicon carbide, zirconium silicates, magnesium silicates, aluminosilicates, metallo aluminosilicates (such as cordierite and spudomene), or a mixture or mixed oxide of any two or more thereof. Cordierite, a magnesium aluminosilicate, and silicon carbide are particularly preferred.

The metallic substrates can be made of any suitable metal, and in particular heat-resistant metals and metal alloys such as titanium and stainless steel as well as ferritic alloys containing iron, nickel, chromium, and/or aluminum in addition to other trace metals.

The flow-through substrate is preferably a flow-through monolith having a honeycomb structure with many small, parallel thin-walled channels running axially through the substrate and extending throughout from an inlet or an outlet of the substrate. The channel cross-section of the substrate can be any shape, but is preferably square, sinusoidal, triangular, rectangular, hexagonal, trapezoidal, circular, or oval.

The filter substrate is preferably a wall-flow monolith filter. The channels of a wall-flow filter are alternately blocked, which allow the exhaust gas stream to enter a channel from the inlet, then flow through the channel walls, and exit the filter from a different channel leading to the outlet. Particulates in the exhaust gas stream are thus trapped in the filter.

The passive $NO_x$ adsorber can be added to the flow-through or filter substrate by any known means. A representative process for preparing the passive $NO_x$ adsorber using a washcoat procedure is set forth below. It will be understood that the process below can be varied according to different embodiments of the invention.

The pre-formed passive $NO_x$ adsorber can be added to the flow-through or filter substrate by a washcoating step. Alternatively, the passive $NO_x$ adsorber can be formed on the flow-through or filter substrate by first washcoating unmodified small pore molecular sieve onto the substrate to produce a molecular sieve-coated substrate. Noble metal can then be added to the activated molecular sieve-coated substrate, which can be accomplished by an impregnation procedure, or the like.

The washcoating procedure is preferably performed by first slurrying finely divided particles of the passive $NO_x$ adsorber (or unmodified small pore molecular sieve) in an appropriate solvent, preferably water, to form the slurry. Additional components, such as transition metal oxides, binders, stabilizers, or promoters can also be incorporated in the slurry as a mixture of water soluble or water-dispersible compounds. The slurry preferably contains between 10 to 70 weight percent solids, more preferably between 20 to 50 weight percent. Prior to forming the slurry, the passive $NO_x$ adsorber (or unmodified small pore molecular sieve) particles are preferably subject to a size reduction treatment (e.g., milling) such that the average particle size of the solid particles is less than 20 microns in diameter.

The flow-through or filter substrate can then be dipped one or more times into the slurry or the slurry can be coated on the substrate such that there will be deposited on the substrate the desired loading of catalytic materials. If noble metal is not incorporated into an activated molecular sieve prior to washcoating the flow-through or filter substrate, the activated molecular sieve-coated substrate is typically dried and calcined and then, the noble metal can be added to the molecular sieve-coated substrate by any known means, including impregnation, adsorption, or ion-exchange, for example, with a noble metal compound (such as palladium nitrate). Preferably, the entire length of the flow-through or filter substrate is coated with the slurry so that a washcoat of the passive $NO_x$ adsorber covers the entire surface of the substrate.

After the flow-through or filter substrate has been coated with the passive $NO_x$ adsorber, and impregnated with noble metal if necessary, the coated substrate is preferably dried and then calcined by heating at an elevated temperature to form the passive $NO_x$ adsorber-coated substrate. Preferably, the calcination occurs at 400 to 600° C. for approximately 1 to 8 hours.

The flow-through or filter substrate can be comprised of the passive $NO_x$ adsorber. In this case, the passive $NO_x$ adsorber can be extruded to form the flow-through or filter substrate. The passive $NO_x$ adsorber extruded substrate is preferably a honeycomb flow-through monolith.

Extruded molecular sieve substrates and honeycomb bodies, and processes for making them, are known in the art. See, for example, U.S. Pat. Nos. 5,492,883, 5,565,394, and 5,633,217 and U.S. Pat. No. Re. 34,804. Typically, the molecular sieve material is mixed with a permanent binder such as silicone resin and a temporary binder such as methylcellulose, and the mixture is extruded to form a green honeycomb body, which is then calcined and sintered to form the final small pore molecular sieve flow-through monolith. The molecular sieve can contain the noble metal prior to extruding such that a passive $NO_x$ adsorber monolith is produced by the extrusion procedure. Alternatively, the noble metal can be added to a pre-formed molecular sieve monolith in order to produce the passive $NO_x$ adsorber monolith.

The invention also includes a method for treating exhaust gas from an internal combustion engine using a passive $NO_x$ adsorber comprising an activated molecular sieve as herein before described. The method comprises adsorbing $NO_x$ onto the passive $NO_x$ adsorber at temperatures at or below 250° C., preferably below 200° C., thermally desorbing $NO_x$ from the passive $NO_x$ adsorber at a temperature above the above stated temperature, and catalytically removing the desorbed $NO_x$ on a catalyst component downstream of the passive $NO_x$ adsorber.

The catalyst component downstream of the passive $NO_x$ adsorber can be an SCR catalyst, a particulate filter, a SCR filter, a $NO_x$ adsorber catalyst, a three-way catalyst, an oxidation catalyst, or combinations thereof.

In an eleventh aspect of the invention, provided is a method of converting methanol to an olefin (MTO) by contacting methanol with an activated H-form molecular sieve comprising an intergrowth of the second aspect of the invention as herein described.

In an eleventh aspect of the invention, provided is a method of converting an oxygenate, such as methanol, to an olefin (MTO) by contacting methanol with an activated molecular sieve of the second aspect of the invention as herein before described. The reaction process for the conversion of an oxygenate to olefin (OTO) is well known in the art. Specifically, in an OTO reaction process, an oxygenate contacts a molecular sieve catalyst composition under conditions effective to convert at least a portion of the oxygenate to light olefins. When methanol is the oxygenate, the process is generally referred to as a methanol to olefin (MTO) reaction process. Methanol is a particularly preferred oxygenate for the synthesis of ethylene and/or propylene.

A process for converting an oxygenate feed to a light olefin product comprises: a) providing an oxygenate feed comprising a majority of methanol; b) providing a catalyst composition comprising an activated molecular sieve and optionally a basic metal oxide co-catalyst; and c) contacting the oxygenate feed with the catalyst composition under conditions sufficient to convert at least a portion of the oxygenate feed to a light olefin product.

An oxygenate feedstock, particularly a mixed alcohol composition containing methanol and ethanol, is a useful feedstock for a variety of catalytic processes, particularly oxygenate to olefin (OTO) reaction processes, in which a catalyst composition, typically containing a primary oxide catalyst having at least two of Al, Si, and P (e.g., an aluminosilicate molecular sieve, preferably a high-silica aluminosilicate molecular sieve) and preferably a basic metal oxide co-catalyst, can be used to convert the oxygenate feedstock into a light olefin product, e.g., containing ethylene and/or propylene, preferably including ethylene. The olefins can then be recovered and used for further processing, e.g., in the manufacture of polyolefins such as polyethylene and/or polypropylene, olefin oligomers, olefin copolymers, mixtures thereof, and/or blends thereof.

One or more additional components can be included in the feedstock that is directed to the OTO reaction system. For example, a feedstock directed to the OTO reaction system can optionally contain, in addition to methanol and ethanol, one or more aliphatic-containing compounds such as alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to 50 carbon atoms, preferably from 1 to 20 carbon atoms, more preferably from 1 to 10 carbon atoms, most preferably from 1 to 4 carbon atoms.

Non-limiting examples of aliphatic-containing compounds include: alcohols such as methanol, ethanol, n-propanol, isopropanol, and the like, alkyl-mercaptans such as methyl mercaptan and ethyl mercaptan, alkyl-sulfides such as methyl sulfide, alkyl amines such as methyl amine, alkyl ethers such as DME, diethyl ether and methyl ethyl ether, alkyl-halides such as methyl chloride and ethyl chloride, alkyl ketones such as dimethyl ketone, alkyl-aldehydes such as formaldehyde and acetaldehyde, and various organic acids such as formic acid and acetic acid.

The various feedstocks discussed above are converted primarily into one or more olefins. The olefins or olefin monomers produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene. Non-limiting examples of olefin monomer(s) include ethylene, propylene, butene-1, pentene-1,4-methyl-pentene-1, hexene-1, octene-1 and decene-1, preferably ethylene, propylene, butene-1, pentene-1,4-methyl-pentene-1, hexene-1, octene-1 and isomers thereof. Other olefin monomers can include, but are not limited to, unsaturated monomers, diolefins having 4 to 18 carbon atoms, conjugated or non-conjugated dienes, polyenes, vinyl monomers, and cyclic olefins.

A catalyst article for converting a low molecular weight oxygen containing species to an olefin rich hydrocarbon stream can comprise an activated molecular sieve, where the activated molecular sieve is disposed on a support and/or within a structure.

A catalyst article for converting a low molecular weight oxygen containing species to an aromatic rich hydrocarbon stream can comprise an activated molecular sieve, where the activated molecular sieve is disposed on a support and/or within a structure.

The catalyst can be incorporated or mixed with other additive materials. Such an admixture is typically referred to as formulated catalyst or as catalyst composition. Preferably, the additive materials are substantially inert to conversion reactions involving dialkyl ethers (e.g., dimethyl ether) and/or alkanols (e.g., methanol, ethanol, and the like).

One or more other materials can be mixed with an activated molecular sieve, particularly a material that is resistant to the temperatures and other conditions employed in organic conversion processes. Such materials can include catalytically active and inactive materials and synthetic or naturally occurring zeolites, as well as inorganic materials such as clays, silica, and/or other metal oxides such as alumina. The latter may be either naturally occurring or in the form of gelatinous precipitates or gels including mixtures of silica and metal oxides. Use of a catalytically active material can tend to change the conversion and/or selectivity of the catalyst in the oxygenate conversion process. Inactive materials suitably can serve as diluents to control the amount of conversion in the process so that products can be obtained in an economic and orderly manner without employing other means for controlling the rate of reaction. These materials can be incorporated into naturally occurring clays, e.g., bentonite and kaolin, to improve the crush strength of the catalyst under commercial operating conditions. The materials (e.g., clays, oxides, etc.) can function as binders for the catalyst. It can be desirable to provide a catalyst having good crush strength, because, in commercial use, it can be desirable to prevent the catalyst from breaking down into powder-like materials.

Naturally occurring clays that can be employed can include, but are not limited to, the montmorillonite and kaolin family, which families include the subbentonites, and the kaolins commonly known as Dixie, McNamee, Georgia and Florida clays, or others in which the main mineral constituent includes halloysite, kaolinite, dickite, nacrite, or anauxite. Such clays can be used in the raw state as originally mined or initially subjected to calcination, acid treatment, or chemical modification. Other useful binders can include, but are not limited to, inorganic oxides such as silica, titania, beryllia, alumina, and mixtures thereof.

In addition to the foregoing materials, an activated molecular sieve can be composited with a porous matrix material such as silica-alumina, silica-magnesia, silica-zirconia, silica-thoria, silica-beryllia and silica-titania as well as ternary compositions such as silica-alumina-thoria, silica-alumina-zirconia, silica-alumina-magnesia and silica-magnesia-zirconia.

The relative proportions of an activated molecular sieve and an inorganic oxide matrix can vary widely. For example, a mixture can include a zeolite content ranging from about 1 to about 90 percent by weight and more usually, particularly when the composite is prepared in the form of beads, in the range from about 2 to about 80 weight percent of the composite.

The invention also relates to C2, C3, C4 and C5 products formed by OTO or MTO application using an activated molecular sieve as a catalyst or co-catalyst.

The following examples demonstrate, but do not limit, aspects of the present invention.

EXAMPLES

Example 1—Synthesis of SDA Containing JMZ-11A with Approximate 54% cha Cavities, 23% aft Cavities and 23% "sfw-GME" Tail 7.27 g of sodium hydroxide (98%) was dissolved in 51.5 g of de-mineralized water in a polypropylene bottle under agitation. To the resulting solution, 27.42 g of a commercial USY powder ($Al_2O_3$=17.44 wt. %, $SiO_2$=55.89 wt. %, $Na_2O$=0.08 wt. %) was added to form a white homogeneous slurry. Next, 26.23 g of N,N-dimethyl-3,5-dimethylpiperidinium hydroxide ($R_4OH$) solution (55.8% aqueous concentration) and then 289.2 g of sodium silicate solution ($Na_2O$ wt. %=9.00 wt. %, $SiO_2$=28.8 wt. %) were sequentially poured into the mixture. The resulting synthesis gel, corresponding to a molar gel formula of $35.0SiO_2$-$1.00Al_2O_3$-$11.0Na_2O$-$1.50R_4OH$-$300H_2O$, was kept for agitation for 30 minutes and then load to a 0.6 L agitated autoclave for crystallization at 120° C. After 68 hours of crystallization, the solid product was recovered and dried in an oven at 120° C. The characteristic XRD data of a sample of Example 1 appears in Table 9 below.

TABLE 9

Powder XRD characteristic lines of SDA containing JMZ-11A hydrated.

| 2-Theta [°] [a] | d-spacing [Å] | Rel. Int. [%] |
|---|---|---|
| 7.7 | 11.47 | 100 |
| 9.6 | 9.17 | 8 |
| 11.8 | 7.51 | 27 |
| 13.1 | 6.74 | 50 |
| 15.2 | 5.84 | 27 |
| 17.6 | 5.04 | 20 |
| 18.0 | 4.92 | 97 |
| 20.0 | 4.44 | 59 |
| 21.0 | 4.23 | 19 |
| 21.9 | 4.06 | 76 |
| 22.6 | 3.93 | 19 |
| 26.2 | 3.40 | 59 |
| 27.3 | 3.27 | 9 |
| 28.1 | 3.18 | 22 |
| 28.7 | 3.11 | 9 |
| 30.3 | 2.95 | 60 |
| 31.0 | 2.89 | 23 |
| 31.6 | 2.83 | 35 |
| 33.7 | 2.66 | 18 |
| 34.8 | 2.58 | 31 |
| 43.7 | 2.07 | 16 |
| 48.0 | 1.89 | 10 |

[a] = ±0.2; Rel. Int. = $I/I_0$ × 100; Peaks with Rel. Int. <5% are not listed.

The as-made powder of Example 1 was directly ion exchanged by applying 4 cycles of contact with ammonium acetate (10 g of solution for gram of zeolite powder, 10% 15 ammonium acetate, 80° C. and 1 hour per ion exchange cycle). After drying in an oven at 120° C., direct ion exchanged product was then calcined to remove the SDA species in a muffler furnace by increasing the temperature to 550° C. with a ramping rate of 1.0° C. per minute. After 6 hours of calcination, the resulting powder was subject to two additional cycles of ion exchange with ammonium acetate to remove residual sodium from the zeolite powder. After removing sodium by ion exchange, the solid product was again dried at 120° C. and calcined at 550° C. with the same procedure. The X-ray diffraction data for the product appears in FIG. 1 and Table 10. The SAR (silica to alumina ratio) of the resulting zeolite was 7.1 as measured by XRF.

TABLE 10

Diffraction peaks of H-JMZ-11A hydrated.

| 2-Theta [°] [a] | d-spacing [Å] | Rel. Int. [%] |
|---|---|---|
| 7.7 | 11.49 | 31 |
| 9.6 | 9.2 | 8 |
| 11.7 | 7.53 | 28 |
| 13.1 | 6.74 | 100 |
| 15.2 | 5.84 | 13 |
| 17.6 | 5.03 | 8 |
| 18.1 | 4.91 | 54 |
| 20 | 4.43 | 33 |
| 20.8 | 4.26 | 11 |
| 21.9 | 4.05 | 34 |
| 22.7 | 3.92 | 7 |
| 26.2 | 3.39 | 38 |
| 27.4 | 3.25 | 6 |
| 28.1 | 3.17 | 10 |
| 28.7 | 3.11 | 7 |

TABLE 10-continued

Diffraction peaks of H-JMZ-11A hydrated.

| 2-Theta [°] [a] | d-spacing [Å] | Rel. Int. [%] |
|---|---|---|
| 30.4 | 2.94 | 24 |
| 31 | 2.88 | 10 |
| 31.6 | 2.83 | 16 |
| 33.8 | 2.65 | 5 |
| 34.9 | 2.57 | 11 |
| 43.9 | 2.06 | 5 |
| 48.1 | 1.89 | 6 |

[a] = ±0.2; Rel. Int. = I/I$_0$ × 100; Peaks with Rel. Int. <5% are not listed.

Example 2—Synthesis of SDA Containing JMZ-11B with Approximate 65% cha Cavities, 5% aft Cavities and 30% "sfw-GME" Tail 13.18 g of sodium hydroxide (98%) was dissolved in 40.0 g of de-mineralized water in a poly propylene bottle under agitation. To the resulting solution, 28.30 g of a commercial USY powder (Al$_2$O$_3$=17.44 wt. %, SiO$_2$=55.89 wt. %, Na$_2$O=0.08 wt. %) was added to form a white homogeneous slurry. Next, 32.9 g of 1,1-Diethyl-2,6-dimethylpiperidinium hydroxide solution (22.0% aqueous concentration) and then 288.5 g of sodium silicate solution (Na$_2$O wt. %=9.00 wt. %, SiO$_2$=28.8 wt. %) were sequentially poured into the mixture. The resulting synthesis gel, corresponding to a molar gel formula of 34.0SiO$_2$-1.00Al$_2$O$_3$-12.0Na$_2$O-0.80R$_C$OH-290H$_2$O, was kept for agitation for 30 minutes and then load to a 0.6 L agitated autoclave for crystallization at 120° C. After 21 hours of crystallization, the solid product was recovered and dried in an oven at 120° C. The XRD data appears in Table 11 below.

TABLE 11

Powder XRD characteristic lines of SDA containing JMZ-11B hydrated.

| 2-Theta [°] [a] | d-spacing [Å] | Rel. Int. [%] |
|---|---|---|
| 7.5 | 11.71 | 42 |
| 10.5 | 8.43 | 9 |
| 12.9 | 6.84 | 55 |
| 15 | 5.9 | 13 |
| 17.8 | 4.98 | 100 |
| 19.8 | 4.47 | 32 |
| 21.3 | 4.17 | 28 |
| 21.9 | 4.05 | 19 |
| 22.5 | 3.96 | 17 |
| 26 | 3.42 | 61 |
| 27.1 | 3.28 | 8 |
| 28 | 3.18 | 6 |
| 30.2 | 2.96 | 44 |
| 31 | 2.88 | 24 |
| 31.6 | 2.83 | 15 |
| 34.6 | 2.59 | 32 |
| 43.5 | 2.08 | 18 |
| 47.8 | 1.9 | 9 |
| 50.8 | 1.8 | 20 |

The as-made powder of Example 2 was ion-exchanged and calcined as described in Example 1. The X-ray diffraction data for the product appears in FIG. 2 and Table 12. The SAR of the resulting zeolite was 6.2 as measured by XRF.

TABLE 12

Diffraction peaks of activated H-JMZ-11B hydrated.

| 2-Theta [°] [a] | d-spacing [Å] | Rel. Int. [%] |
|---|---|---|
| 7.6 | 11.65 | 20 |
| 10.8 | 8.22 | 14 |
| 13 | 6.8 | 100 |
| 15.1 | 5.88 | 9 |
| 17.9 | 4.94 | 53 |
| 19.9 | 4.45 | 23 |
| 21.4 | 4.15 | 16 |
| 22.1 | 4.02 | 12 |
| 22.5 | 3.94 | 8 |
| 26.1 | 3.41 | 31 |
| 27.2 | 3.27 | 4 |
| 28.1 | 3.17 | 4 |
| 30.3 | 2.95 | 18 |
| 31.1 | 2.87 | 11 |
| 31.8 | 2.81 | 9 |
| 34.7 | 2.58 | 9 |
| 43.7 | 2.07 | 4 |
| 48 | 1.9 | 4 |
| 51 | 1.79 | 6 |

Example 3—Synthesis of SDA Containing JMZ-11C with Approximate 39% cha Cavities, 54% aft Cavities and 7% "sfw-GME" Tail 27.35 g of a commercial USY powder (Al$_2$O$_3$=17.44 wt. %, SiO$_2$=55.89 wt. %, Na$_2$O=0.08 wt. %) was combined with 45.77 g of de-mineralized water in a poly propylene bottle under agitation to form a white homogeneous slurry. To the solution, 24.42 g of N,N-Dimethyl-3,5-dimethylpiperidinium hydroxide solution (55.8% aqueous concentration) and 8.29 g of 1,3-bis(1-adamantyl)imidazolium hydroxide (20.0% aqueous concentration) were added. 7.39 g of NaOH (98%) and 288.4 g of sodium silicate solution (Na$_2$O wt. %=9.00 wt. %, SiO$_2$=28.8 wt. %) were sequentially poured into the mixture. The resulting synthesis gel, corresponding to a molar gel formula of 35.0SiO$_2$-1.00Al$_2$O$_3$-11.0Na$_2$O-1.40R$_A$OH-0.10R$_B$OH-300H$_2$O, was kept for agitation for 30 minutes and then loaded to a 0.6 L agitated autoclave for crystallization at 120° C. After 24 hours of crystallization, the solid product was recovered and dried in an oven at 120° C. The XRD data appears in Table 13 below.

TABLE 13

Powder XRD characteristic lines of SDA containing JMZ-11C hydrated.

| 2-Theta [°] [a] | d-spacing [Å] | Rel. Int. [%] |
|---|---|---|
| 7.5 | 11.86 | 7 |
| 8.1 | 10.92 | 6 |
| 9.2 | 9.61 | 12 |
| 11.6 | 7.62 | 32 |
| 12.9 | 6.85 | 100 |
| 17.4 | 5.08 | 7 |
| 17.9 | 4.95 | 50 |
| 19.8 | 4.47 | 11 |
| 20.5 | 4.32 | 14 |
| 21.8 | 4.08 | 25 |
| 22.2 | 4.01 | 6 |
| 26 | 3.42 | 28 |
| 28.1 | 3.18 | 8 |
| 30.2 | 2.95 | 10 |
| 30.6 | 2.92 | 11 |
| 31.5 | 2.84 | 11 |

TABLE 13-continued

Powder XRD characteristic lines of
SDA containing JMZ-11C hydrated.

| 2-Theta [°] (a) | d-spacing [Å] | Rel. Int. [%] |
|---|---|---|
| 31.8 | 2.81 | 6 |
| 34.7 | 2.58 | 9 |

The as-made powder of Example 3 was ion-exchanged and calcined as described in Example 1. The X-ray diffraction data for the product appears in FIG. 4 and Table 14. The SAR of the resulting zeolite was 8.0 as measured by XRF.

TABLE 14

Diffraction peaks of activated H-JMZ-11C hydrated.

| 2-Theta [°] (a) | d-spacing [Å] | Rel. Int. [%] |
|---|---|---|
| 7.5 | 11.75 | 26 |
| 8 | 11.03 | 12 |
| 9.4 | 9.41 | 17 |
| 11.5 | 7.68 | 21 |
| 12.9 | 6.86 | 48 |
| 15 | 5.91 | 18 |
| 15.9 | 5.57 | 14 |
| 17.4 | 5.11 | 24 |
| 17.7 | 5 | 100 |
| 19.8 | 4.48 | 45 |
| 20.6 | 4.32 | 41 |
| 21.7 | 4.09 | 72 |
| 22.5 | 3.96 | 23 |
| 26 | 3.41 | 34 |
| 27.2 | 3.27 | 7 |
| 27.8 | 3.21 | 24 |
| 28.5 | 3.13 | 8 |
| 30.2 | 2.96 | 47 |
| 30.6 | 2.92 | 42 |
| 31.4 | 2.85 | 37 |
| 33.5 | 2.68 | 17 |
| 34.6 | 2.59 | 34 |
| 42.8 | 2.11 | 9 |
| 43.6 | 2.08 | 21 |

Example 4—Synthesis of SDA Containing JMZ-11D with Approximate 65% cha Cavities, 12% aft Cavities and 23% "sfw-GME" Tail 7.27 g of sodium hydroxide (98%) was dissolved in 45.7 g of de-mineralized water in a poly propylene bottle under agitation. To the resulting solution, 27.41 g of a commercial USY powder ($Al_2O_3$=17.44 wt. %, $SiO_2$=55.89 wt. %, $Na_2O$=0.08 wt. %) was added to form a white homogeneous slurry. Next, 26.23 g of N,N-dimethyl-3,5-dimethylpiperidinium hydroxide solution (55.8% aqueous concentration), 5.83 g of trimethyladmandylammonium hydroxide (0.51% aqueous concentration) and then 289.2 g of sodium silicate solution ($Na_2O$ wt. %=9.00 wt. %, $SiO_2$=28.8 wt. %) were sequentially poured into the mixture. The resulting synthesis gel, corresponding to a molar gel formula of $35.0SiO_2$-$1.00Al_2O_3$-$11.0Na_2O$-$1.50R_AOH$-$0.003R_BOH$-$300H_2O$, was kept for agitation for 30 minutes and then load to a 0.6 L agitated autoclave for crystallization at 120° C. After 64 hours of crystallization, the solid product was recovered and dried in an oven at 120° C. The XRD data appears in Table 15 below.

TABLE 15

Powder XRD characteristic lines of
SDA containing JMZ-11D hydrated.

| 2-Theta [°] (a) | d-spacing [Å] | Rel. Int. [%] |
|---|---|---|
| 7.6 | 11.66 | 25 |
| 9.7 | 9.1 | 9 |
| 11.6 | 7.59 | 25 |
| 13 | 6.79 | 100 |
| 15.1 | 5.88 | 12 |
| 17.5 | 5.06 | 7 |
| 17.9 | 4.95 | 50 |
| 19.9 | 4.45 | 27 |
| 20.8 | 4.26 | 9 |
| 21.8 | 4.07 | 26 |
| 22.6 | 3.93 | 6 |
| 26.1 | 3.41 | 33 |
| 28 | 3.19 | 8 |
| 30.3 | 2.95 | 19 |
| 30.9 | 2.89 | 8 |
| 31.6 | 2.83 | 12 |
| 34.8 | 2.58 | 9 |

The as-made powder of Example 4 was ion-exchanged and calcined as described in Example 1. The X-ray diffraction data for the product appears in FIG. 8 and Table 16. The SAR of the resulting zeolite was 7.3 as measured by XRF.

TABLE 16

Diffraction peaks of H-JMZ-11D hydrated.

| 2-Theta [°] (a) | d-spacing [Å] | Rel. Int. [%] |
|---|---|---|
| 7.6 | 11.66 | 25 |
| 9.7 | 9.1 | 9 |
| 11.6 | 7.59 | 25 |
| 13 | 6.79 | 100 |
| 15.1 | 5.88 | 12 |
| 17.5 | 5.06 | 7 |
| 17.9 | 4.95 | 50 |
| 19.9 | 4.45 | 27 |
| 20.8 | 4.26 | 9 |
| 21.8 | 4.07 | 26 |
| 22.2 | 4 | 11 |
| 26.1 | 3.4 | 33 |
| 28 | 3.19 | 8 |
| 30.3 | 2.95 | 19 |
| 30.9 | 2.89 | 8 |
| 31.6 | 2.83 | 12 |
| 31.8 | 2.8 | 8 |
| 34.8 | 2.58 | 9 |

Example 5—Preparation of Cu Catalyst for SCR

Calcined JMZ-11A from Example 1, Example 2, Example 3 and Example 4, respectively, were impregnated with copper at a loading of 3.33 wt. % using the required amount of copper (II) acetate monohydrate (Shepherd) dissolved in de-mineralised water. The impregnated samples were dried overnight at 80° C. and then calcined in air at 550° C. for 4 hours. A reference sample of BEA with SAR 28 was prepared following the same method described above.

Samples of the powdered catalyst were pelletized to provide the fresh catalyst, and a portion of the fresh catalyst is then hydrothermally aged in a flow of 10% $H_2O$ in air using the following procedure: the samples were heated at a rate of 10° C./min to 250° C. in air only. The samples were then heated at a rate of 10° C./min in 10% $H_2O$ in air to 750° C. After being held at a temperature of 750° C. for 80 hours, the samples were cooled in the steam/air mixture until then temperature was <250° C., then air only flowed over the samples until they cooled to about room temperature.

Example 6—Catalyst Testing for Standard NH$_3$ SCR

Pelletized fresh and aged samples of the powder catalyst were tested in an apparatus in which a gas comprising 500 ppm NO$_x$ (NO-only), 500 ppm NH$_3$, 14% O$_2$, 4.6% H$_2$O, 5% CO$_2$, with the remainder being N$_2$ flowed over the catalyst at a space velocity of 90K/h. The samples were heated from room temperature to 150° C. under the above mentioned gas mixture except for NH$_3$. At 150° C., NH$_3$ was added in to the gas mixture and the samples were held under these conditions for 30 min. The temperature was then increased (ramped) from 150 to 500° C. at 5° C./minute.

Figure 26:
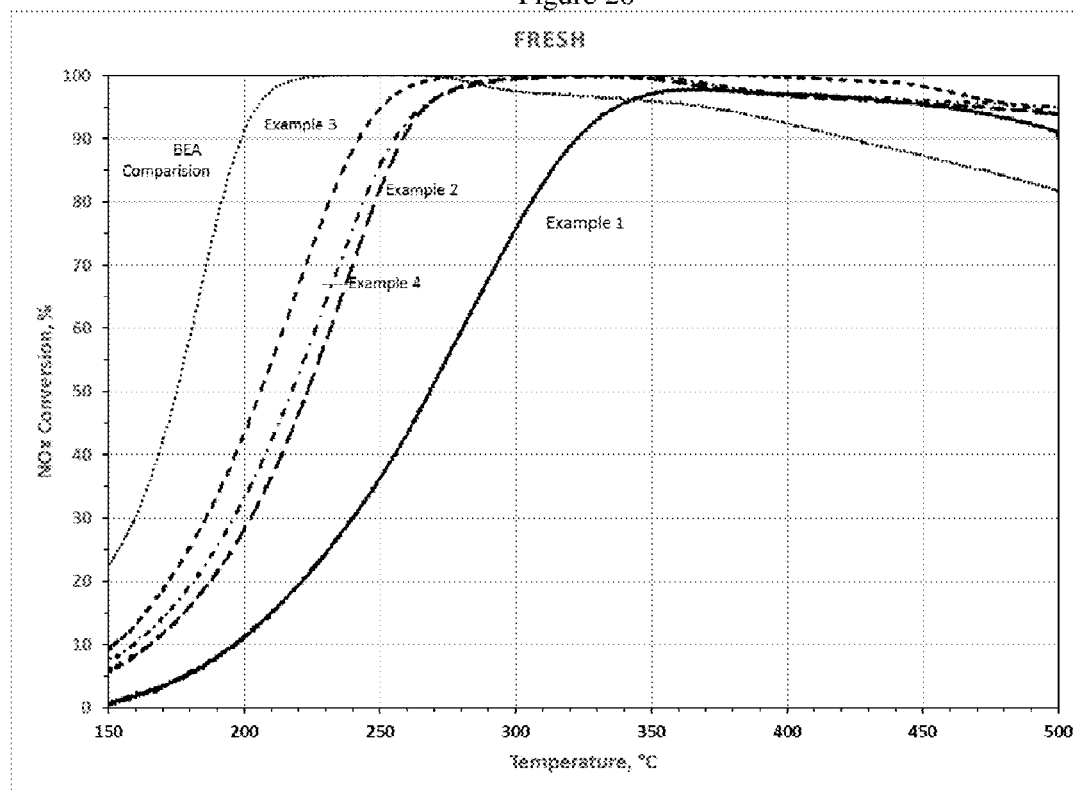
FIG. 26 shows $NO_x$ conversion profiles from fresh JMZ-11 samples impregnated with Cu.
Figure 27:
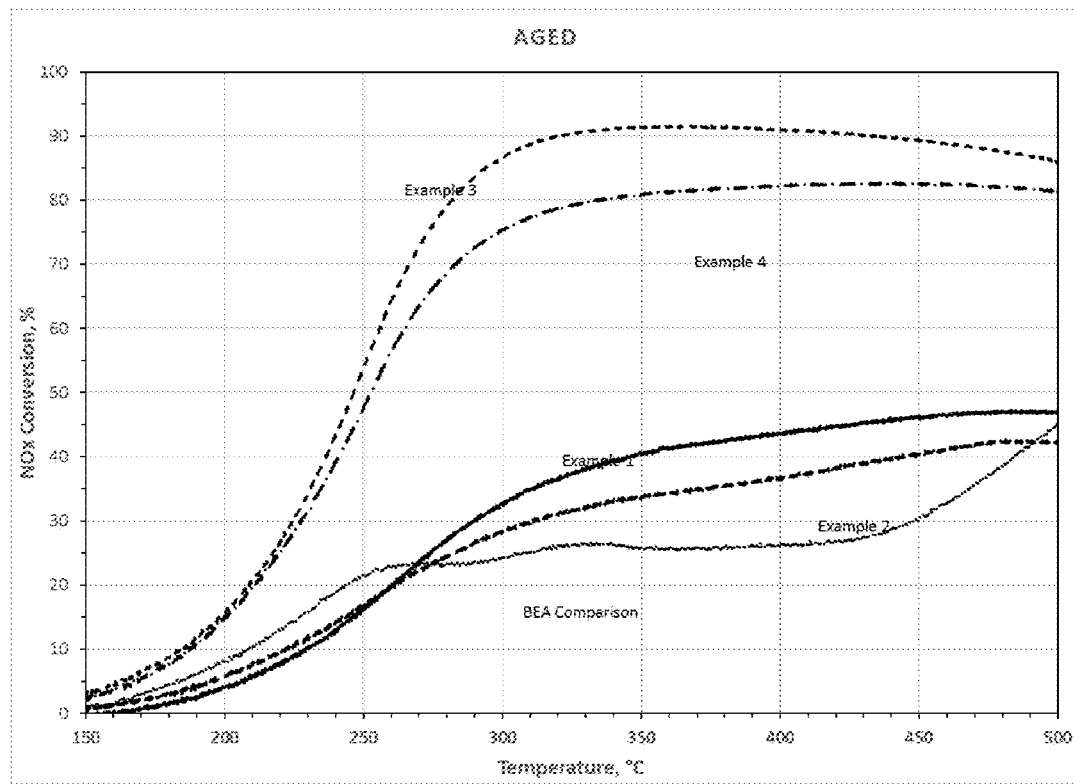
FIG. 27 shows $NO_x$ conversion profiles from aged JMZ-11 samples impregnated with Cu.

NO$_x$ conversion activity profile results are depicted in FIGS. 26 and 27. It has been found that a fresh sample of Example 1 demonstrated NO$_x$ conversion levels of 1%-15% higher than the benchmark BEA.Cu in the temperatures range of 340° C.-550° C. (FIG. 26). Example 2, 3, and 4 all exhibited NO$_x$ conversion levels of 1%-15% higher than the benchmark BEA.Cu in the temperatures range of 275° C.-550° C. After aging, (FIG. 27) Example 3 and 4 showed NO$_x$ conversion levels of 5-65% higher than BEA.Cu across the entire tested temperature range of 150-550° C. After aging, Example 1 and 2 exhibited NO$_x$ conversion levels of 2-20% higher than that of BEA.Cu in the temperature range of 275-450° C. Therefore, it has been demonstrated that Examples 1, 2, 3, and 4 exhibit significant advantages in NO$_x$ conversion when utilized in the optimal operating temperature range.

Figure 28:
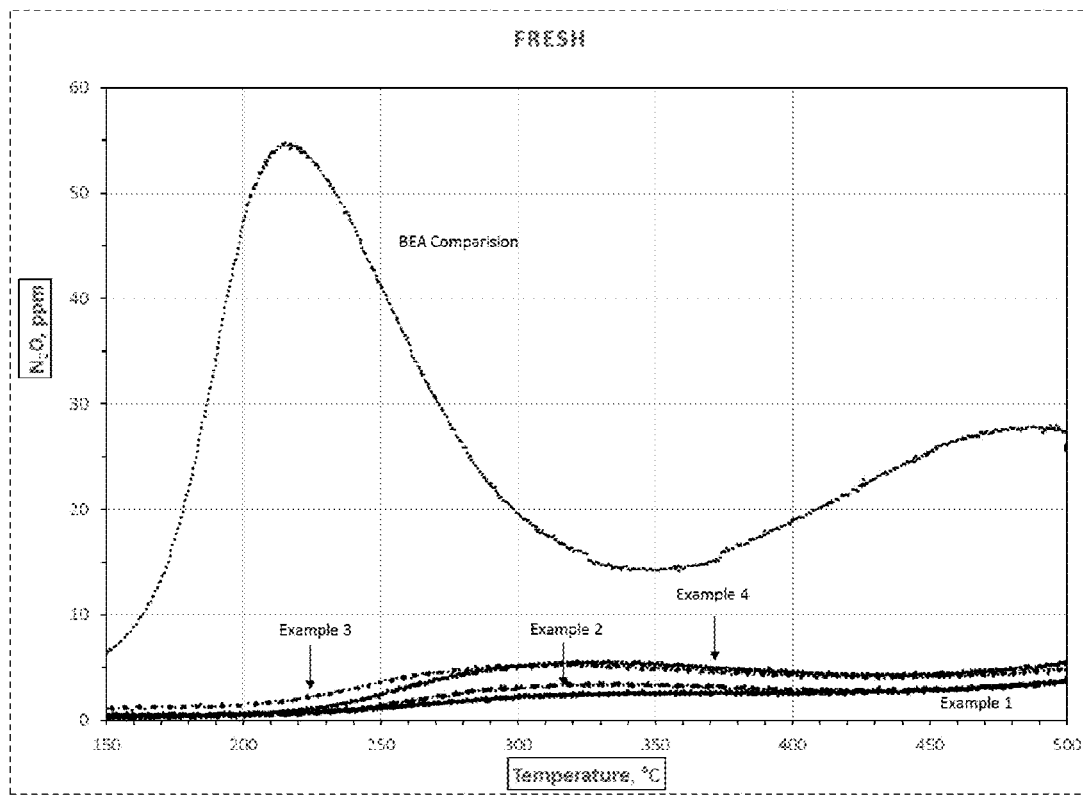
FIG. 28 shows $N_2O$ production profiles from fresh JMZ-11 samples impregnated with Cu.
Figure 29:
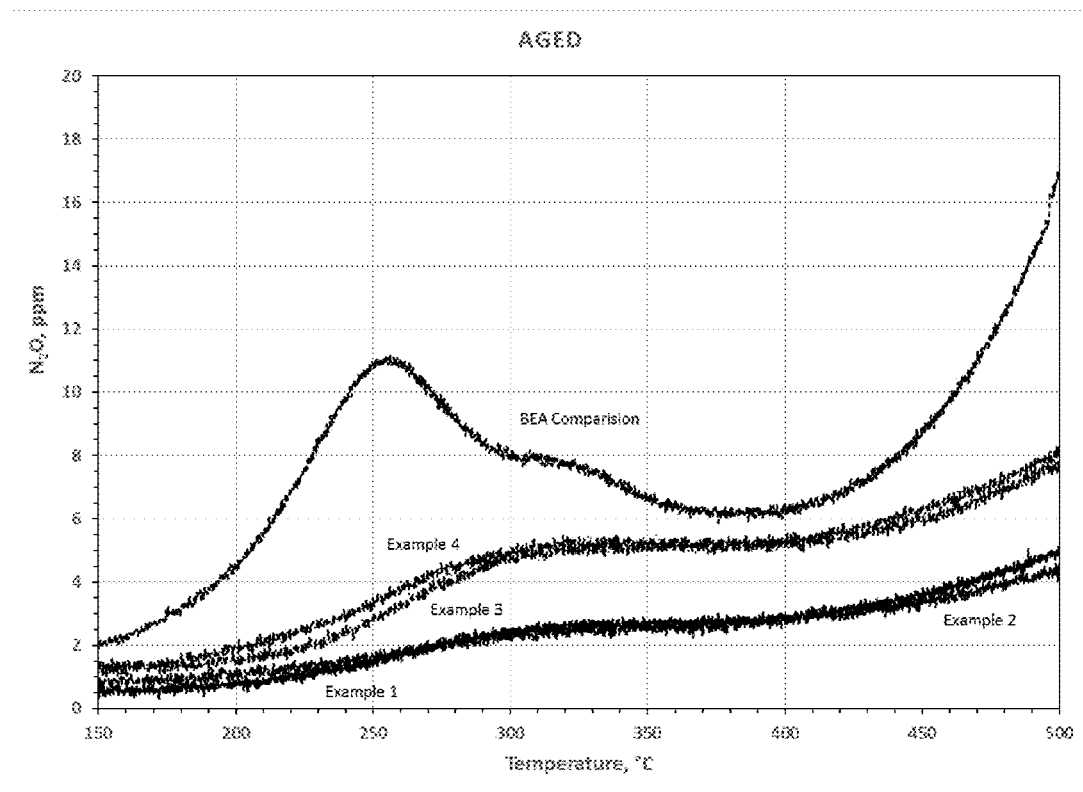
FIG. 29 shows $N_2O$ production profiles from aged JMZ-11 samples impregnated with Cu.

The concentration of N$_2$O in gas passing through fresh and aged catalysts over temperatures from 150° C. to 500° C. are given in FIG. 28. Gas flowing into the apparatus contained 500 ppm NO$_x$ as NO-only. The levels of N$_2$O produced by Examples 1, 2, 3, and 4 were all significantly lower (~5 ppm peak value) than that of BEA (peak values of ~55 ppm and 28 ppm) over the entire temperature range. After aging (FIG. 29), N$_2$O levels produced by BEA significantly decreased over the entire temperature range exhibiting peak values at ~11 ppm and ~18 ppm. However, aged samples of Example 1, 2, 3, and 4 all still produced lower levels of N$_2$O than BEA over the entire temperature range despite the observation that these samples also exhibited higher NO$_x$ conversion over the majority of the temperature range. Thus, Example 1, 2, 3, and 4 all exhibit significant advantages in N$_2$O production over BEA both fresh and aged.

What is claimed is:

1. A molecular sieve comprising a first structure directing agent (SDA-1), cha cavities, aft cavities and an "sfw-GME" tail, wherein SDA-1 comprises an N,N-dimethyl-3,5-dimethylpiperidinium cation or an N,N-diethyl-2,6-dimethylpiperidinium cation, wherein said molecular sieve has a framework, and wherein the sfw-GME tail has a monotonically decreasing distribution of cavity sizes.

2. The molecular sieve of claim 1, wherein SDA-1 comprises an N,N-dimethyl-3,5-dimethylpiperidinium cation, the cha cavities are present at about 45 to about 65% of the cavities in the tail, the aft cavities are present at about 18 to about 28% of the cavities in the tail, and the remaining about 7 to about 37% are present as larger cavities in the "sfw-GME" tail, and wherein the larger cavities compass a range in cavity sizes from that of the sfw cavities to "infinity".

3. The molecular sieve of claim 2, wherein the "sfw-GME" tail accounts for about 35-80% of the volume of the molecular sieve.

4. The molecular sieve of claim 1, wherein the molecular sieve is an aluminosilicate and a powder XRD pattern of the hydrated aluminosilicate has the following characteristic lines with the corresponding intensities:

| 2-Theta [°] (a) | d-spacing [Å] | Rel. Int. [%] |
|---|---|---|
| 7.7 | 11.47 | vs |
| 9.6 | 9.17 | w |
| 11.8 | 7.51 | m |
| 13.1 | 6.74 | s |
| 15.2 | 5.84 | m |
| 17.6 | 5.04 | m |
| 18.0 | 4.92 | vs |
| 20.0 | 4.44 | s |
| 21.0 | 4.23 | w |
| 21.9 | 4.06 | vs |
| 22.6 | 3.93 | w |
| 26.2 | 3.40 | s |
| 27.3 | 3.27 | w |
| 28.1 | 3.18 | m |
| 28.7 | 3.11 | w |
| 30.3 | 2.95 | s |
| 31.0 | 2.89 | m |
| 31.6 | 2.83 | m |
| 33.7 | 2.66 | w |
| 34.8 | 2.58 | m |
| 43.7 | 2.07 | w |
| 48.0 | 1.89 | w |

(a) = ±0.2, Rel. Int. = I/I0 × 100; Peaks with Rel. Int. <5% are not listed wherein "Rel Int" is defined as: w (weak)<20; m (medium) is >20 and <40; s (strong) is >40 and <60; and vs (very strong) is >60, compared to the maximum peak height.

5. The molecular sieve of claim 1, wherein SDA-1 comprises an N,N-diethyl-2,6-dimethylpiperidinium cation, the cha cavities are present at about 55 to about 75 are present as larger cavities in the "sfw-GME" tail, and wherein the larger cavities compass a range in cavity sizes from that of the sfw cavities to "infinity".

6. The molecular sieve of claim 5, wherein the "sfw-GME" tail accounts for about 40-80% of the volume of the molecular sieve and the molecular sieve has a monotonically decreasing distribution of cavity sizes.

7. The molecular sieve of claim 1, wherein the molecular sieve is an aluminosilicate and a powder XRD pattern of the hydrated aluminosilicate has the following characteristic lines with the corresponding intensities:

| 2-Theta [°] (a) | d-spacing [Å] | Rel. Int. [%] |
|---|---|---|
| 7.5 | 11.71 | m-s |
| 10.5 | 8.43 | w |
| 12.9 | 6.84 | s-vs |
| 15.0 | 5.90 | w |
| 17.8 | 4.98 | vs |
| 19.8 | 4.47 | m |
| 21.3 | 4.17 | m |
| 21.9 | 4.05 | w-m |
| 22.5 | 3.96 | w-m |
| 26.0 | 3.42 | s-vs |
| 27.1 | 3.28 | w |
| 28.0 | 3.18 | w |
| 30.2 | 2.96 | m-s |

-continued

| 2-Theta [°] (a) | d-spacing [Å] | Rel. Int. [%] |
|---|---|---|
| 31.0 | 2.88 | m |
| 31.6 | 2.83 | w |
| 34.6 | 2.59 | m |
| 43.5 | 2.08 | w-m |
| 47.8 | 1.90 | w |

(a) = ±0.2, Rel. Int. = I/I0 × 100; Peaks with Rel. Int. <5% are not listed wherein "Rel Int" is defined as: w (weak)<20; m (medium) is >20 and <40; s (strong) is >40 and <60; and vs (very strong) is >60, compared to the maximum peak height.

8. The molecular sieve of claim 1, wherein SDA-1 comprises an N,N-dimethyl-3,5-dimethylpiperidinium cation and the molecular sieve further comprises a 1,3-bis(1-adamantyl)imidazolium cation, wherein the cha cavities are present at about 30 to about 45% of the cavities in the tail, the aft cavities are present at about 45 to about 65% of the cavities in the tail, and the remaining about 2 to about 20% are present as larger cavities in the "sfw-GME" tail, and wherein the larger cavities compass the range in cavity sizes from that of the sfw cavities to "infinity".

9. The molecular sieve of claim 8, wherein the "sfw-GME" tail accounts for about 5-45% of the volume of the molecular sieve.

10. The molecular sieve of claim 1, wherein the molecular sieve is an aluminosilicate and a powder XRD pattern of the hydrated aluminosilicate has the following characteristic lines with the corresponding intensities:

| 2-Theta [°] (a) | d-spacing [Å] | Rel. Int. [%] |
|---|---|---|
| 7.5 | 11.86 | w |
| 8.1 | 10.92 | w |
| 9.2 | 9.61 | w |
| 11.6 | 7.62 | m |
| 12.9 | 6.85 | vs |
| 17.4 | 5.08 | w |
| 17.9 | 4.95 | s |
| 19.8 | 4.47 | w |
| 20.5 | 4.32 | w |
| 21.8 | 4.08 | m |
| 22.2 | 4.01 | w |
| 26.0 | 3.42 | m |
| 28.1 | 3.18 | w |
| 30.2 | 2.95 | w |
| 30.6 | 2.92 | w |
| 31.5 | 2.84 | w |
| 31.8 | 2.81 | w |
| 34.7 | 2.58 | w |

(a) = ±0.2, Rel. Int. = I/I/0 × 100; Peaks with Rel. Int. <5% are not listed wherein "Rel Int" is defined as: w (weak)<20; m (medium) is >20 and <40; s (strong) is >40 and <60; and vs (very strong) is >60, compared to the maximum peak height.

11. The molecular sieve of claim 1, wherein SDA-1 comprises an N,N-dimethyl-3,5-dimethylpiperidinium cation and the molecular sieve further comprises a trimethyl-admandylammonium cation, wherein the cha cavities are present at about 55 to about 75% of the cavities in the tail, the aft cavities are present at about 7 to about 17% of the cavities in the tail, and the remaining about 8 to about 38% are present as larger cavities in the "sfw-GME" tail, and wherein a larger cavities compass the range in cavity sizes from that of the sfw to "infinity".

12. The molecular sieve of claim 11, wherein the "sfw-GME" tail accounts for about 50-90% of the volume of the molecular sieve.

13. The molecular sieve of claim 1, wherein the molecular sieve is an aluminosilicate and a powder XRD pattern of the hydrated aluminosilicate has the following characteristic lines with the corresponding intensities:

| 2-Theta [°] (a) | d-spacing [Å] | Rel. Int. [%] |
|---|---|---|
| 7.6 | 11.66 | m |
| 9.7 | 9.1 | w |
| 11.6 | 7.59 | m |
| 13 | 6.79 | vs |
| 15.1 | 5.88 | w |
| 17.5 | 5.06 | w |
| 17.9 | 4.95 | s |
| 19.9 | 4.45 | m |
| 20.8 | 4.26 | w |
| 21.8 | 4.07 | m |
| 22.6 | 3.93 | w |
| 26.1 | 3.41 | m |
| 28 | 3.19 | w |
| 30.3 | 2.95 | w-m |
| 30.9 | 2.89 | w |
| 31.6 | 2.83 | w |
| 34.8 | 2.58 | w |

(a) = ±0.2, Rel. Int. = I/I0 × 100; Peaks with Rel. Int. <5% are not listed wherein "Rel Int" is defined as: w (weak)<20; m (medium) is >20 and <40; s (strong) is >40 and <60; and vs (very strong) is >60, compared to the maximum peak height.

14. The molecular sieve of claim 1, wherein the molecular sieve has a monotonically decreasing distribution of cavity sizes.

15. An activated molecular sieve comprising cha cavities, aft cavities and an "sfw-GME" tail, wherein the molecular sieve does not comprise an SDA, wherein said molecular sieve has a framework, and wherein the sfw-GME tail has a monotonically decreasing distribution of cavity sizes.

16. The activated molecular sieve of claim 15, wherein the cha cavities are present at about 45 to about 65% of the cavities in the tail, the aft cavities are present at about 18 to about 28% of the cavities in the tail, and the remaining about 7 to about 37% are present as larger cavities in the "sfw-GME" tail, and wherein the larger cavities compass a range in cavity sizes from that of the sfw cavities to "infinity".

17. The activated molecular sieve of claim 16, wherein the "sfw-GME" tail accounts for about 35-80% of the volume of the molecular sieve.

18. The activated molecular sieve of claim 15, wherein the molecular sieve is an aluminosilicate and a powder XRD pattern of the hydrated aluminosilicate has the following characteristic lines with the corresponding intensities:

| 2-Theta [°] (a) | d-spacing [Å] | Rel. Int. [%] |
|---|---|---|
| 7.7 | 11.49 | m |
| 9.6 | 9.20 | w |
| 11.7 | 7.53 | m |
| 13.1 | 6.74 | vs |
| 15.2 | 5.84 | w |
| 17.6 | 5.03 | w |

-continued

| 2-Theta [°] (a) | d-spacing [Å] | Rel. Int. [%] |
|---|---|---|
| 18.1 | 4.91 | s |
| 20.0 | 4.43 | m |
| 20.8 | 4.26 | w |
| 21.9 | 4.05 | m |
| 22.7 | 3.92 | w |
| 26.2 | 3.39 | m |
| 27.4 | 3.25 | w |
| 28.1 | 3.17 | w |
| 28.7 | 3.11 | w |
| 30.4 | 2.94 | m |
| 31.0 | 2.88 | w |
| 31.6 | 2.83 | w |
| 33.8 | 2.65 | w |
| 34.9 | 2.57 | w |
| 43.9 | 2.06 | w |
| 48.1 | 1.89 | w |

(a) = ±0.2, wherein "Rel Int" is defined as: w (weak)<20; m (medium) is >20 and <40; s (strong) is >40 and <60; and vs (very strong) is >60, compared to the maximum peak height.

19. The activated molecular sieve of claim 15, wherein the cha cavities are present at about 55 to about 75% of the cavities in the tail, and the remaining about 15 to about 45% are present as larger cavities in the "sfw-GME" tail, and wherein the larger cavities compass a range in cavity sizes from that of the sfw cavities to "infinity".

20. The activated molecular sieve of claim 19, wherein the "sfw-GME" tail accounts for about 40-80% of the volume of the molecular sieve and the molecular sieve has a monotonically decreasing distribution of cavity sizes.

21. The activated molecular sieve of claim 15, wherein the molecular sieve is an aluminosilicate and a powder XRD pattern of the dehydrated aluminosilicate has the following characteristic lines with the corresponding intensities:

| 2-Theta [°] (a) | d-spacing [Å] | Rel. Int. [%] |
|---|---|---|
| 7.6 | 11.65 | w-m |
| 10.8 | 8.22 | w |
| 13.0 | 6.80 | vs |
| 15.1 | 5.88 | w |
| 17.9 | 4.94 | s |
| 19.9 | 4.45 | w-m |
| 21.4 | 4.15 | w-m |
| 22.1 | 4.02 | w |
| 22.5 | 3.94 | w |
| 26.1 | 3.41 | m |
| 27.2 | 3.27 | w |
| 28.1 | 3.17 | w |
| 30.3 | 2.95 | w-m |
| 31.1 | 2.87 | w |
| 31.8 | 2.81 | w |
| 34.7 | 2.58 | w |
| 43.7 | 2.07 | w |
| 48.0 | 1.90 | w |

(a) = ±0.2, Rel. Int. = I/I0 × 100; Peaks with Rel. Int. <5% are not listed wherein "Rel Int" is defined as: w (weak)<20; m (medium) is >20 and <40; s (strong) is >40 and <60; and vs (very strong) is >60, compared to the maximum peak height.

22. The activated molecular sieve of claim 15, wherein the cha cavities are present at about 30 to about 45% of the cavities in the tail, the aft cavities are present at about 45 to about 65% of the cavities in the tail, and the remaining about 2 to about 20% are present as larger cavities in the "sfw-GME" tail, and wherein the larger cavities compass a range in cavity sizes from that of the sfw to "infinity".

23. The activated molecular sieve of claim 22, wherein the "sfw-GME" tail accounts for about 5-45% of the volume of the molecular sieve.

24. The activated molecular sieve of claim 15, wherein the molecular sieve is an aluminosilicate and a powder XRD pattern of the dehydrated aluminosilicate has the following characteristic lines with the corresponding intensities:

| 2-Theta [°] (a) | d-spacing [Å] | Rel. Int. [%] |
|---|---|---|
| 7.5 | 11.75 | m |
| 8.0 | 11.03 | w |
| 9.4 | 9.41 | w |
| 11.5 | 7.68 | w-m |
| 12.9 | 6.86 | s |
| 15.0 | 5.91 | w-m |
| 15.9 | 5.57 | w |
| 17.4 | 5.11 | m |
| 17.7 | 5.00 | vs |
| 19.8 | 4.48 | s |
| 20.6 | 4.32 | m-s |
| 21.7 | 4.09 | vs |
| 22.5 | 3.96 | w-m |
| 26.0 | 3.41 | m |
| 27.2 | 3.27 | w |
| 27.8 | 3.21 | m |
| 28.5 | 3.13 | w |
| 30.2 | 2.96 | s |
| 30.6 | 2.92 | s |
| 31.4 | 2.85 | m-s |
| 33.5 | 2.68 | w |
| 34.6 | 2.59 | m |
| 42.8 | 2.11 | w |
| 43.6 | 2.08 | w-m |

(a) = ±0.2, Rel. Int. = I/I0 × 100; Peaks with Rel. Int. <5% are not listed wherein "Rel Int" is defined as: w (weak)<20; m (medium) is >20 and <40; s (strong) is >40 and <60; and vs (very strong) is >60, compared to the maximum peak height.

25. The activated molecular sieve of claim 15, wherein the cha cavities are present at about 55 to about 75% of the cavities in the tail, the aft cavities are present at about 7 to about 17% of the cavities in the tail, and the remaining about 8 to about 38% are present as larger cavities in the "sfw-GME" tail, and wherein the larger cavities compass a range in cavity sizes from that of the sfw cavities to "infinity".

26. The activated molecular sieve of claim 25, wherein the "sfw-GME" tail accounts for about 50-90% of the volume of the molecular sieve.

27. The activated molecular sieve of claim 15, wherein the molecular sieve is an aluminosilicate and a powder XRD pattern of the dehydrated aluminosilicate has the following characteristic lines with the corresponding intensities:

| 2-Theta [°] (a) | d-spacing [Å] | Rel. Int. [%] |
|---|---|---|
| 7.6 | 11.66 | m |
| 9.7 | 9.10 | w |
| 11.6 | 7.59 | m |
| 13.0 | 6.79 | vs |
| 15.1 | 5.88 | w |

-continued

| 2-Theta [°] (a) | d-spacing [Å] | Rel. Int. [%] |
|---|---|---|
| 17.5 | 5.06 | w |
| 17.9 | 4.95 | s |
| 19.9 | 4.45 | m |
| 20.8 | 4.26 | w |
| 21.8 | 4.07 | m |
| 22.2 | 4.00 | w |
| 26.1 | 3.40 | m |
| 28.0 | 3.19 | w |
| 30.3 | 2.95 | w-m |
| 30.9 | 2.89 | w |
| 31.6 | 2.83 | w |
| 31.8 | 2.80 | w |
| 34.8 | 2.58 | w |

(a) = ±0.2, Rel. Int. = I/I0 × 100; Peaks with Rel. Int. <5% are not listed wherein "Rel Int" is defined as: w (weak)<20; m (medium) is >20 and <40; s (strong) is >40 and <60; and vs (very strong) is >60, compared to the maximum peak height.

28. The activated molecular sieve of claim 15, wherein the molecular sieve has a monotonically decreasing distribution of cavity sizes.

29. The molecular sieve of claim 1, where the molecular sieve is an aluminosilicate or a metal-substituted aluminosilicate, wherein the metal is substituted into the framework of the molecular sieve.

30. The molecular sieve of claim 1, wherein the molecular sieve is an aluminosilicate having a silica to alumina ratio (SAR) of 20 or less.

31. The molecular sieve of claim 1, where the molecular sieve comprises phosphorus in the framework.

32. The molecular sieve of claim 1, where the molecular sieve comprises at least one metal within the framework where the metal is selected from at least one of the metals of groups IIIA, IB, IIB, VA, VIA, VIIA, and VIIIA of Groups of the Periodic Table and combinations thereof.

33. The activated molecular sieve of claim 15, where the molecular sieve further comprises at least one extra-framework metal selected from the group consisting of Ag, Au, Ce, Co, Cr, Cu, Fe, Ga, In, Jr, Mn, Mo, Ni, Os, Pd, Pt, Re, Rh, Ru, Sn and Zn.

34. The activated molecular sieve of claim 15, where the molecular sieve further comprises at least one extra-framework metal selected from the group consisting of Ag, Au, Jr, Os, Pd, Pt, Rh and Ru.

35. A catalyst comprising the activated molecular sieve of claim 15.

36. The catalyst of claim 35, wherein the activated molecular sieve comprises about 0.1 to about 5 weight percent of at least one extra-framework metal.

37. The catalyst of claim 35, wherein the activated molecular sieve comprises about 0.1 to about 5 weight percent ionic copper.

38. A catalyst article for treating exhaust gas comprising a catalyst of claim 35, where the catalyst is disposed on and/or within a honeycomb structure.

39. A method for treating an exhaust gas comprising contacting a combustion exhaust gas containing $NO_x$ and/or $NH_3$ with the activated molecular sieve according to claim 15 to selectively reduce at least a portion of the $NO_x$ into $N_2$ and $H_2O$ and/or oxidize at least a portion of the $NH_3$.

40. A method for treating an exhaust gas comprising contacting a combustion exhaust gas containing $NO_x$ with a passive NOx absorber comprising the activated molecular sieve of claim 15.

41. A method for treating an exhaust gas comprising contacting a combustion exhaust gas containing $NO_x$ with a passive NOx absorber comprising the activated molecular sieve of claim 15.

42. A method of converting methanol to an olefin (MTO), the method comprising contacting methanol with the activated molecular sieve of claim 15.

* * * * *